(12) United States Patent
Alabugin et al.

(10) Patent No.: US 8,927,778 B2
(45) Date of Patent: Jan. 6, 2015

(54) MODULAR SYNTHESIS OF GRAPHENE NANORIBBONS AND GRAPHENE SUBSTRUCTURES FROM OLIGO-ALKYNES

(71) Applicant: The Florida State University Research Foundation, Inc., Tallahassee, FL (US)

(72) Inventors: Igor Alabugin, Tallahassee, FL (US); Philip M. Byers, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 36 days.

(21) Appl. No.: 13/658,886

(22) Filed: Oct. 24, 2012

(65) Prior Publication Data

US 2013/0109855 A1 May 2, 2013

Related U.S. Application Data

(60) Provisional application No. 61/554,031, filed on Nov. 1, 2011.

(51) Int. Cl.
*C07C 43/205* (2006.01)
*C07C 43/225* (2006.01)
*C07D 311/94* (2006.01)
*C07D 307/79* (2006.01)

(52) U.S. Cl.
CPC ............ *C07D 307/79* (2013.01); *C07D 311/94* (2013.01); *C07C 43/225* (2013.01)
USPC .......................................... 568/659; 568/661

(58) Field of Classification Search
USPC ................................................ 568/661, 659
See application file for complete search history.

(56) References Cited

U.S. PATENT DOCUMENTS

2013/0196985 A1* 8/2013 Ding et al. ................. 514/233.2

OTHER PUBLICATIONS

Frank B. Mallory et al., Phenacenes: a family of graphite ribbons. Part 3: Iterative strategies for the synthesis of large phenacenes, Tetrahedron, 57, © 2001 Elsevier Science Ltd., (2001) pp. 3715-3724.
Jishan Wu et al., Graphenes as Potential Material for Electronics, Chemical Reviews, vol. 107, No. 3, © 2007 American Chemical Society, (2007), pp. 718-747.
Alexander J. Berresheim et al., Polyphenylene Nanostructures, Chemical Reviews, vol. 99, No. 7, © 1999 American Chemical Society, (1999), pp. 1747-1785.
A.K. Geim and K.S Novoselov, The Rise of Graphene, Nature Materials, vol. 6, © 2007 Nature Publishing Group, (Mar. 2007), pp. 183-191.
Yoichiro Kuninobu et al., Synthesis of Functionalized Pentacenes from Isobenzofurans Derived from C—H Bond Activation, Organic Letters, vol. 12, No. 22, © 2010 American Chemical Society, (Oct. 20, 2010), pp. 5287-5289.
Ullrich Scherf, Ladder-type materials, J. Mater. Chem., vol. 9, 1999, pp. 1853-1864.
Matthew J. Allen et al., Honeycomb Carbon: A Review of Graphene, Chemical Reviews, vol. 110, No. 1, © 2010 American Chemical Society, (Jul. 17, 2009), pp. 132-145.
Marc B. Goldfinger and Timothy M. Swager, Fused Polycyclic Aromatics via Electrophile-Induced Cyclization Reactions: Application to the Synthesis of Graphite Ribbons, J. Am. Chem. Soc., vol. 116, No. 17, © 1994 American Chemical Society, (1994), pp. 7895-7896.
Christopher R. Swartz et al., Synthesis and Characterization of Electron-Deficient Pentacenes, Organic Letters, vol. 7, No. 15, © 2005 American Chemical Society, (Jun. 30, 2005), pp. 3163-3166.
Xiaolin Li et al., Chemically Derived, Ultrasmooth Graphene Nanoribbon Semiconductors, Science, vol. 319, © 2008 by the American Association for the Advancement of Science, (Feb. 29, 2008), pp. 1229-1232.

\* cited by examiner

*Primary Examiner* — James O Wilson
*Assistant Examiner* — Cecilia M Jaisle
(74) *Attorney, Agent, or Firm* — Armstrong Teasdale LLP

(57) ABSTRACT

A method for the synthesis of carbon-based structures, particularly graphene substructures and ribbons, from oligo- and poly-alkyne starting materials.

7 Claims, 27 Drawing Sheets

(Only One Combination is Shown)

Scheme 5. Synthesis of Organic Rectifiers.

1. Central Core

2. Methoxy Arm

Tet. Lett. 2004, 45, 803-807

3. Nitrile Arm

*J. Org. Chem.* 2009, 74, 21-25

1. Core Piece

2. Synthesis of Pyridazine Arm

*Tett. Lett.* 2009, *50*, 2682-2684

Mix of Regioisomers

1. Synthesis of Central Core

2. Synthesis of Pyridine Arm

MODULAR SYNTHESIS OF GRAPHENE NANORIBBONS AND GRAPHENE SUBSTRUCTURES FROM OLIGO-ALKYNES

CROSS REFERENCE TO RELATED APPLICATIONS

This application claims priority from U.S. Provisional Application Ser. No. 61/554,031, filed on Nov. 1, 2011, the disclosure of which is incorporated herein as if set forth in its entirety.

STATEMENT REGARDING FEDERALLY SPONSORED RESEARCH & DEVELOPMENT

This invention was made with government support under Grant No. CHE-084686 awarded by the National Science Foundation. The government has certain rights in this invention.

FIELD OF THE INVENTION

The field of the invention generally relates to the synthesis of conjugated, cyclized carbon-based structures from oligo-alkyne starting materials, and more specifically to the synthesis of carbon-rich conjugated polyaromatic nanostructures from oligo-alkyne starting materials via cascade radical cyclizations.

BACKGROUND OF THE INVENTION

The 2010 Nobel Prize illustrates the evolution of graphene from a mere curiosity to the new face of carbon. Graphene is a flat sheet of $sp^2$ carbon atoms arranged into hexagons, giving it the appearance of a honeycomb lattice. See Geim, A. K.; Novoselov, K. S. The Rise of Graphene, *Nature Materials*. 2007, 6, 183-191, which may be accessed at: http://www.nature.com/nmat/journal/v6/n3/abs/nmat1849.html.

Graphite ribbons are predicted to have very interesting electronic properties which combine the relatively small band gap with high switching speeds and carrier mobility. See (A) Li, X.; Wang, X.; Li, Z.; Lee, S. Dai, H. *Science* 2008, 319, 1229; (B) Wu, J.; Pisula, W.; Müllen, K. Graphenes as Potential Material for Electronics, *Chem. Rev.* 2007, 107, 718-747, which may be accessed at http://pubs.acs.org/doi/abs/10.1021/cr068010r; and (C) Allen, M. J.; Tung, V. C.; Kaner, R. B. Honeycomb Carbon: A Review of Graphene, *Chem. Rev.* 2010. 110, 132-145, which may be accessed at http://pubs.acs.org/doi/abs/10.1021/cr900070d.

In order to take the full advantage of graphene as a building block in the new generation of materials, one needs to prepare it in a chemically homogeneous and well-defined state. Subtle variations in structure (zigzag vs. chair arrangement at the edges, size and shape) are known to affect the electronic properties very strongly. This challenge has to be met through the rationally designed chemical approaches to the synthesis of graphene in order to advance the future development of the field of carbon-based nanoelectronics. Not surprisingly, a number of synthetic approaches to such ribbons illustrated on the left have been developed. See Goldfinger, M. B.; Swager, T. M. *J. Am. Chem. Soc.* 1994, 116, 7895. Scherf, U. *J. Mater. Chem.* 1999, 9, 1853; and Berresheim, A. J.; Mueller, M.; Muellen, K. *Chem. Rev.* 1999, 99, 1747. Mallory, F. B.; Butler, K. E.; Berube, A.; Luzik, E. D.; Mallory, C. W.; Brondyke, E. J.; Hiremath, R.; Ngo, P.; Carroll, P. J. *Tetrahedron* 2001, 57, 3715. Several of these prior art syntheses are shown in FIG. 1.

There are both practical and conceptual limitations to the current approaches to the preparation of graphene ribbons. While the current syntheses often provide an elegant solution to the design of a symmetric functionalized graphene pieces, efficient and flexible approaches to non-symmetrically carved and/or substituted graphene substructures are, at best, scarce. See Kuninobu, Y.; Seiki, T.; Kanamaru, S.; Nishina, Y.; Takai, K. Synthesis of functionalized Pentacenes from Isobenzofurans Derived from C—H Bond Activation, *Org. Lett.*, 2010, 12, 5287-5289, which may be accessed at: http://pubs.acs.org/doi/abs/10.1021/ol102349r.

BRIEF DESCRIPTION OF THE INVENTION

Briefly, therefore, the present invention is directed to a compound comprising repeat units having the structure (I):

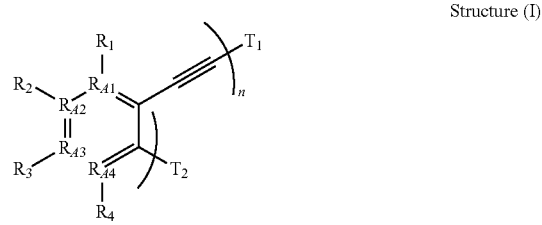

Structure (I)

In the compound of structure (I), n is an integer having a value of at least three; $R_{A1}$, $R_{A2}$, $R_{A3}$, and $R_{A4}$ are each independently carbon or nitrogen; $R_1$, $R_2$, $R_3$, and $R_4$ are each independently hydrogen; an election pair; a substituted or unsubstituted aliphatic moiety; a substituted or unsubstituted aromatic moiety; a substituted or unsubstituted alkoxy moiety; cyano; nitro; sulfinate; sulfonate; amino; or a substituted or unsubstituted alkylamino; or any two of $R_1$, $R_2$, $R_3$, and $R_4$ together with the atoms to which they are bonded may form a fused cycloalkyl, a fused heterocycloalkyl, a fused aromatic ring, or a fused heteroaromatic ring; $T_1$ and $T_2$ are each independently selected from the group consisting of hydrogen, an aliphatic moiety having from about 1 to about 18 carbon atoms; an aromatic moiety having from three to 18 carbon atoms; an alkoxy moiety having from 1 to about 6 carbon atoms; and a cyano moiety.

In the compound of structure (I), at least one of the repeat units comprises an $R_1$ moiety having the structure (II):

Structure (II)

In the context of structure (II), Y comprises a reactive moiety selected from the group consisting of bromine, iodine, xanthate, or a carbonyl compound which can be converted into a radical; and Z comprises a group selected from the group consisting of O, S, S(O), $SO_2$, $CR_7R_8$, or $NR_9$; and $R_7$, $R_8$, and $R_9$ are each independently selected from the group consisting of hydrogen, an aliphatic moiety having from 1 to about 10 carbon atoms; an aromatic moiety having from three to 10 carbon atoms; and an aromatic moiety having from 14 to 20 carbon atoms.

The present invention is further directed to polyaromatic compounds prepared by cyclizing compounds having structure (I).

The present invention is still further directed to a method of cyclizing compounds having structure (I).

DETAILED DESCRIPTION OF THE EMBODIMENT(S) INVENTION

The present invention is directed to the synthesis of conjugated, cyclized carbon-based structures from oligo-alkyne and poly-alkyne starting materials, and more specifically to the synthesis of carbon-rich conjugated polyaromatic nanostructures from oligo-alkyne starting materials via cascade radical cyclizations. In particular, the present invention is directed to a method of preparing substructures of the graphite allotrope. Even more particularly, the method of the present invention is directed to the design of a new organic synthetic route which may open access to a variety of graphene substructures. According to the method of the present invention, ortho oligo-alkyne and ortho poly-alkyne chains of varying sizes, equipped with different functionalities, are built in a modular fashion using well-characterized and reliable Sonogashira coupling chemistry. In the key step, these systems are then "zipped" up via a cascade of fast and selective radical cyclizations. See FIG. 2, which depicts a model synthesis of graphene ribbons and substructures according to the method of the present invention.

Figure 1:
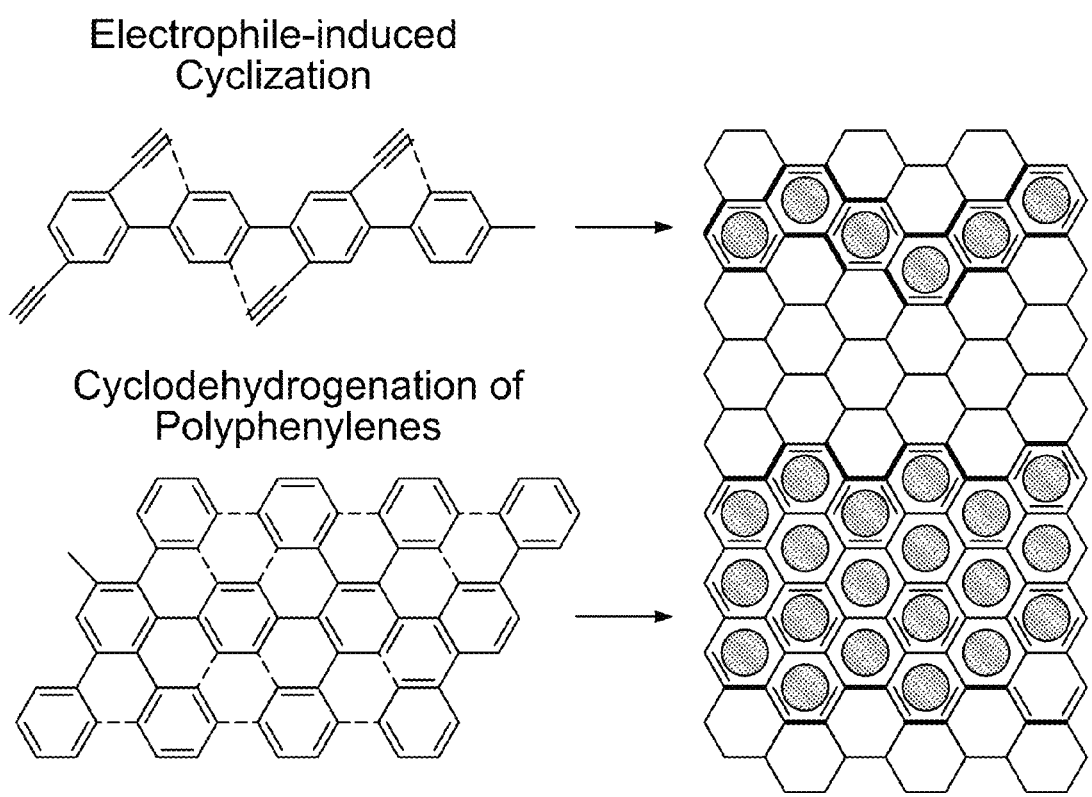
FIG. 1 is a depiction of prior art syntheses of graphene.
Figure 2:
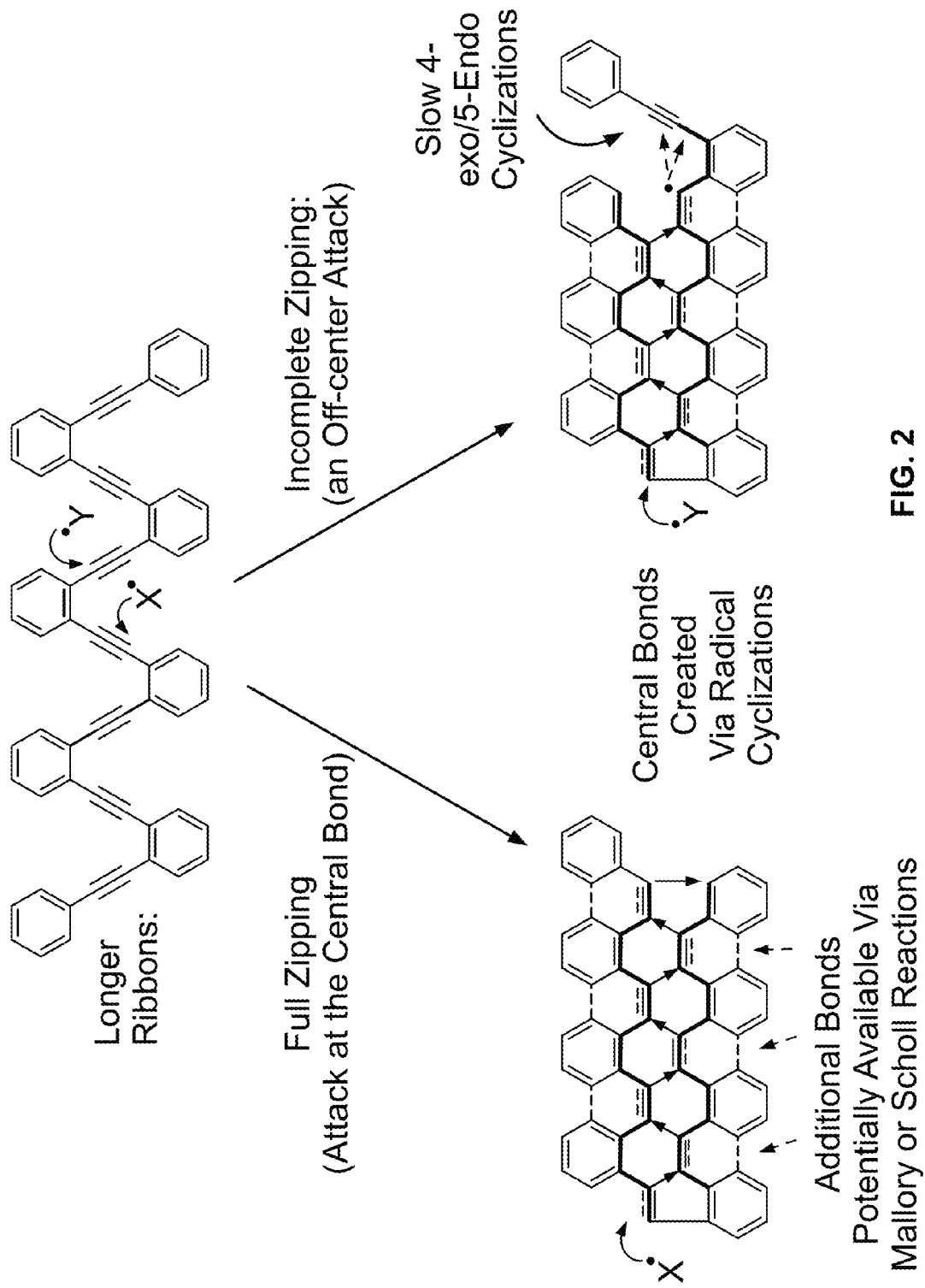
FIG. 2 is a depiction of syntheses of graphene ribbons and substructures according to the present invention.

In general, the ortho oligo- or poly-alkyne chain as depicted in the model synthesis depicted in FIG. 2 may comprise multiple aromatic moieties, each of which may be the same or different.

In some embodiments, an ortho oligo- or poly-alkyne compound for use in the method of the present invention has the following Structure (I) comprising the general aromatic-alkyne repeat unit:

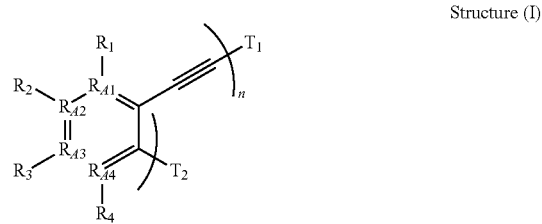

Structure (I)

In the above structure (I), n is an integer having a value of at least three, preferably at least four. The value of n may be between 3 and 25, such as between three and fifteen, such as between about three and about 10, such as between about three and six. In some embodiments, the value of n is at least 4, such as between 4 and about 25, or between four and fifteen, or between four and 10, or even between four and seven. The value of n herein denotes the number of aromatic-alkyne repeat units. The value does not restrict the compound to embodiments wherein each repeat unit is identical. In contrast, the compounds of the present invention comprise at least one aromatic-alkyne repeat unit which may differ from the others by including a moiety at the $R_1$ position, which is useful for initializing the cyclization reaction and which may not be present on the other repeat units. See Structure (II) below. According to the present invention, each repeat unit may be different. The modular synthesis of the present invention enables the synthesis of oligo-alkyne and poly-alkyne chains have a wide variety of structural and functional features.

In the above structure (I), $R_{A1}$, $R_{A2}$, $R_{A3}$, and $R_{A4}$ are each independently carbon or nitrogen. In some embodiments, from 1 to 4 of the $R_{A1}$, $R_{A2}$, $R_{A3}$, and $R_{A4}$ are carbon. In some embodiments, from 1 to 4 of the $R_{A1}$, $R_{A2}$, $R_{A3}$, and $R_{A4}$ are nitrogen. The modular assembly of such compounds, as explained more fully herein, enables the preparation of ortho oligo- or poly-alkyne compounds of the present invention in which each repeat unit has an identical aromatic ring structure. The modular assembly alternatively allows preparation of compounds in which each repeat unit has a different aromatic ring structure. For example, in some embodiments, all of the aromatic rings in the repeat unit may comprise phenyl groups, which may be substituted or unsubstituted. In some embodiments, all of the aromatic rings in the repeat unit may comprise pyridyl rings, which may be substituted or unsubstituted. In still other embodiments, one or more of the at least three, preferably at least four, aromatic rings may comprise a phenyl group and one or more of the at least three, preferably at least four, aromatic rings may comprise a pyridyl group.

Furthermore, each aromatic ring may comprise different substituents. For example, some aromatic rings may be substituted with cyano, while other aromatic rings may be substituted with alkoxy.

In some embodiments of the above structure (I), $R_1$, $R_2$, $R_3$, and $R_4$ are each independently hydrogen; an electron pair (i.e., when the corresponding ring atom is nitrogen); an aliphatic moiety; an aromatic moiety; an alkoxy moiety; cyano; nitro; sulfinyl; sulfonyl; amino; or an alkylamino. Each repeat unit of structure (I) may comprise different substituents at the $R_1$, $R_2$, $R_3$, and $R_4$ positions. The aliphatic moiety (e.g., alkyl, alkenyl, alkynyl, cycloalkyl) may have from 1 to 18 carbon atoms, or from 1 to about 14 carbon atoms, or 1 to about 10 carbon atoms, such as 1 to about 6 carbon atoms. The aromatic moiety having from three to 18 carbon atoms, such as from three to 10 carbon atoms, or three to six carbon atoms. The alkoxy moiety having from 1 to about 6 carbon atoms, such as from 1 to about 3 carbon atoms. The alkylamino may have from 1 to 18 carbon atoms, or from 1 to about 14 carbon atoms, or 1 to about 10 carbon atoms, such as 1 to about 6 carbon atoms. The aliphatic moiety, aromatic moiety, alkoxy, or alkyl amino moiety may be substituted or unsubstituted. Substituents include halogen (e.g., chlorine, bromine, or iodine), amino, xanthyl, or cyano.

In some embodiments of the above structure (I), any two of $R_1$, $R_2$, $R_3$, and $R_4$ of one or more repeat units together with the atoms (carbon, nitrogen, sulfur, or oxygen) to which they are bonded may form a fused cycloalkyl (which may be homocycloalkyl or heterocycloalkyl) or aromatic ring (which may be homoaromatic, such as phenyl, or heteroaromatic) or multiple fused aromatic rings. Fused heterocycloalkyl and heteroaromatic moieties may comprise nitrogen (e.g., pyridyl, pyridazinyl, triazinyl), sulfur (e.g., thiophenyl, thiophene, benzothiophene), or oxygen (e.g., furanyl, tetrahydrofuranyl).

In some preferred embodiments of Structure (I), each of $R_1$, $R_2$, $R_3$, $R_4$ on each repeat unit is hydrogen, other than one repeat unit, which comprises a moiety having structure (II) below at the $R_1$ substituent position. In some preferred embodiments, at least one of $R_1$, $R_2$, $R_3$, $R_4$ on each repeat unit is cyano. Again, one repeat unit comprises a moiety having structure (II) below at the $R_1$ substituent position. In some preferred embodiments, both $R_2$ and $R_3$ together from a tetrahydrofuran.

The above structure (I) comprises a chain of aromatic-alkyne repeat units comprising at least three alkyne moieties, such as at least four alkyne moieties, each of which is bonded to an aromatic ring. At least one of the aromatic rings among the three or more comprises a moiety having the structure (II) below at the $R_1$ moiety position:

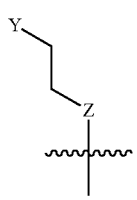

Structure (II)

In the above structure (II), Y comprises a reactive moiety, such as bromine, iodine, xanthyl, or a carbonyl compound which can be converted into a radical. The xanthyl is generally bonded through the sulfur atom. Xanthates include xanthic acid and esters of xanthic acid, such as alkyl esters having from 1 to about 6 carbon atoms, including methyl xanthate, ethyl xanthate, propyl xanthates. This compound may be prepared as shown in Scheme 1 (see FIG. 3) by employing ethynyltrimethylsilane as the group and deprotecting the compound via base-mediated (for example, potassium carbonate or tetrabutylammonium fluoride) protodesilylation in methanol/tetrahydrofuran.

In the above structure (II), Z comprises a group selected from among O, S, S(O), $SO_2$, $CR_7R_8$, or $NR_9$. $R_7$, $R_8$, and $R_9$ may be hydrogen, an aliphatic moiety (e.g., alkyl, alkenyl, alkynyl, cycloalkyl) having from 1 to about 10 carbon atoms, such as 1 to about 6 carbon atoms; an aromatic moiety having from three to 10 carbon atoms (e.g., toluene, naphthyl, para-methoxyphenyl), or six carbon atoms (e.g., phenyl, para-fluorophenyl), or 14 to 20 carbon atoms (anthracene, phenanthrene, alkylanthracene, alkylphenanthrene).

In some preferred embodiments, Z comprises an oxygen atom. In some preferred embodiments, Z comprises an oxygen atom and Y comprises bromine. In some preferred embodiments, Z comprises an oxygen atom and Y comprises iodine. In some preferred embodiments, Z comprises an oxygen atom and Y comprises a xanthate.

Preferably, the repeat unit comprising the above $R_1$ group substituent having structure (II) is located centrally in the ortho oligo- or poly-alkyne chain such that the compound is essentially symmetrical, i.e., having substantially an equal number (i.e., within 1) of alkyne moieties on either side of the aromatic ring of the repeat unit having the above $R_1$ group substituent. More specifically, if the oligo- or poly-alkyne chain comprises an even number of repeat units, the $R_1$ group substituent having structure (II) is located on the aromatic ring of a repeat unit at the n/2 position or the n/2+1 position. For example, if the oligo-alkyne of structure (I) comprises six repeat units, the $R_1$ group substituent having structure (II) is located on the aromatic ring of the third or fourth repeat unit. If the oligo-alkyne of structure (I) comprises an odd number of repeat units, the $R_1$ group substituent having structure (II) is located on the aromatic ring at the n/2+0.5 position. For example, if the oligo-alkyne of structure (I) has five repeat units, the $R_1$ group substituent having structure (II) is located on the aromatic ring of the third repeat unit. This embodiment is preferred since the cyclization reactions can proceed essentially symmetrically from the central aromatic ring.

The ortho oligo- or poly-alkyne chain of structure (I) may be terminated (represented by groups $T_1$ and $T_2$) with a group selected from among hydrogen, an aliphatic moiety (e.g., alkyl, alkenyl, alkynyl, cycloalkyl, such as tetrahydrofuranyl) having from about 1 to about 18 carbon atoms, from 1 to about 14 carbon atoms, or 1 to about 10 carbon atoms, such as 1 to about 6 carbon atoms; an aromatic moiety having from three to 18 carbon atoms, such as from three to 10 carbon atoms (e.g., toluene, naphthyl, para-methoxyphenyl, thiophenyl, furanyl), or six carbon atoms (e.g., phenyl, para-fluorophenyl), or 14 to 20 carbon atoms (anthracene, phenanthrene, alkylanthracene, alkylphenanthrene); an alkoxy moiety having from 1 to about 6 carbon atoms; or a cyano moiety.

In some embodiments, each of $R_{A1}$, $R_{A2}$, $R_{A3}$, and $R_{A4}$ are carbon, and the ortho oligo- or poly-alkyne compound for use in the method of the present invention has the following Structure (III) comprising the general aromatic-alkyne repeat unit:

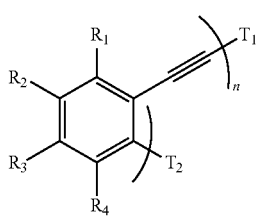

Structure (III)

In the above structure (III), n, $R_1$, $R_2$, $R_3$, $R_4$, $T_1$, and $T_2$ have the same definitions as provided in connection with structure (I).

In structure (III), at least one of the aromatic rings among the three or more comprises an $R_1$ moiety having the structure (II):

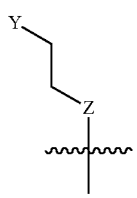

Structure (II)

wherein Y and Z have been previously defined.

In some preferred embodiments of Structure (III), each of $R_1$, $R_2$, $R_3$, $R_4$ of each repeat unit are hydrogen, other than the repeat unit comprising a moiety having structure (II) at the $R_1$ substituent position. In some preferred embodiments, at least one of $R_1$, $R_2$, $R_3$, $R_4$ on each repeat unit is cyano. Again, one repeat unit comprises a moiety having structure (II) below at the $R_1$ substituent position. In some preferred embodiments, both $R_2$ and $R_3$ together from a tetrahydrofuran.

In order for the cascade to proceed fully without any unreacted alkyne units remaining after the reaction, initiation proceeds at the central alkyne. See FIG. 2. Because intermolecular activation does not proceed with the sufficient selectivity for the substrates with more than three alkynes, the method of the present invention employs intramolecular activation via introduction of a "weak link," a chemically different functionality which can be activated selectively in the presence of multiple alkynes.

In order to prepare ortho-poly-alkyne chains that can be zipped up to prepare highly cyclized materials, an ortho-alkyne starting material is prepared comprising a moiety representing a "weak link." Within the context of the present invention, "weak link" is terminology for a functional group which will eventually be employed to initiate radical cyclization.

Oligo- and poly-alkynes of general structure (I) and of the specific structures shown in structure (IV) may be prepared by modular synthesis using a wide variety of aryl-alkyne building blocks. Modular synthesis enables the preparation of oligo-alkynes and poly-alkynes having four alkyne moieties as shown in Structure (IV) or more, such as five, six, seven, eight, nine, or ten alkynes, or even more such as 11, 12, 13 alkynes and so on. According to some embodiments of the present invention, a bis-alkyne model compound having a moiety representing the "weak link" and particularly suitable for preparing oligo-alkyne chains having an even number of alkyne moieties may have the following general structure (IV):

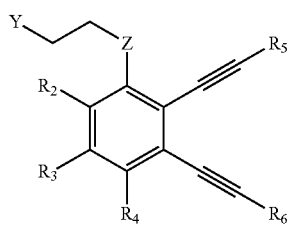

Structure (IV)

In the context of Structure (IV), $R_2$, $R_3$, and $R_4$ have the same definitions as provided in connection with Structure (I). Further, Y and Z have the same definitions as provided in connection with Structure (II).

In the above structure (IV), $R_5$ and $R_6$ may be selected from among hydrogen, an aliphatic moiety (e.g., alkyl, alkenyl, alkynyl, cycloalkyl) having from about 1 to about 18 carbon atoms, from 1 to about 14 carbon atoms, or 1 to about 10 carbon atoms, such as 1 to about 6 carbon atoms; an aromatic moiety having from three to 18 carbon atoms, such as from three to 10 carbon atoms (e.g., toluene, naphthyl, para-methoxyphenyl), or six carbon atoms (e.g., phenyl, para-fluorophenyl), or 14 to 20 carbon atoms (anthracene, phenanthrene, alkylanthracene, alkylphenanthrene); an alkoxy moiety having from 1 to about 6 carbon atoms; or a cyano moiety.

Examples of model compounds having structure (IV) are provided below:

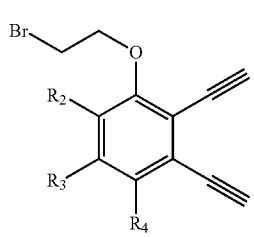

Structure (IVa)

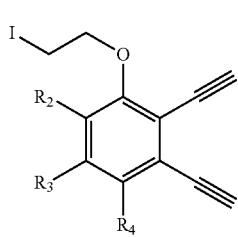

Structure (IVb)

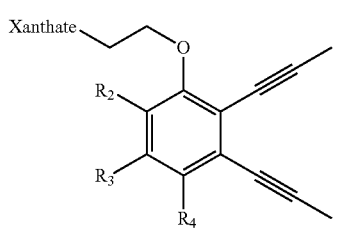

Structure (IVc)

Figure 3:
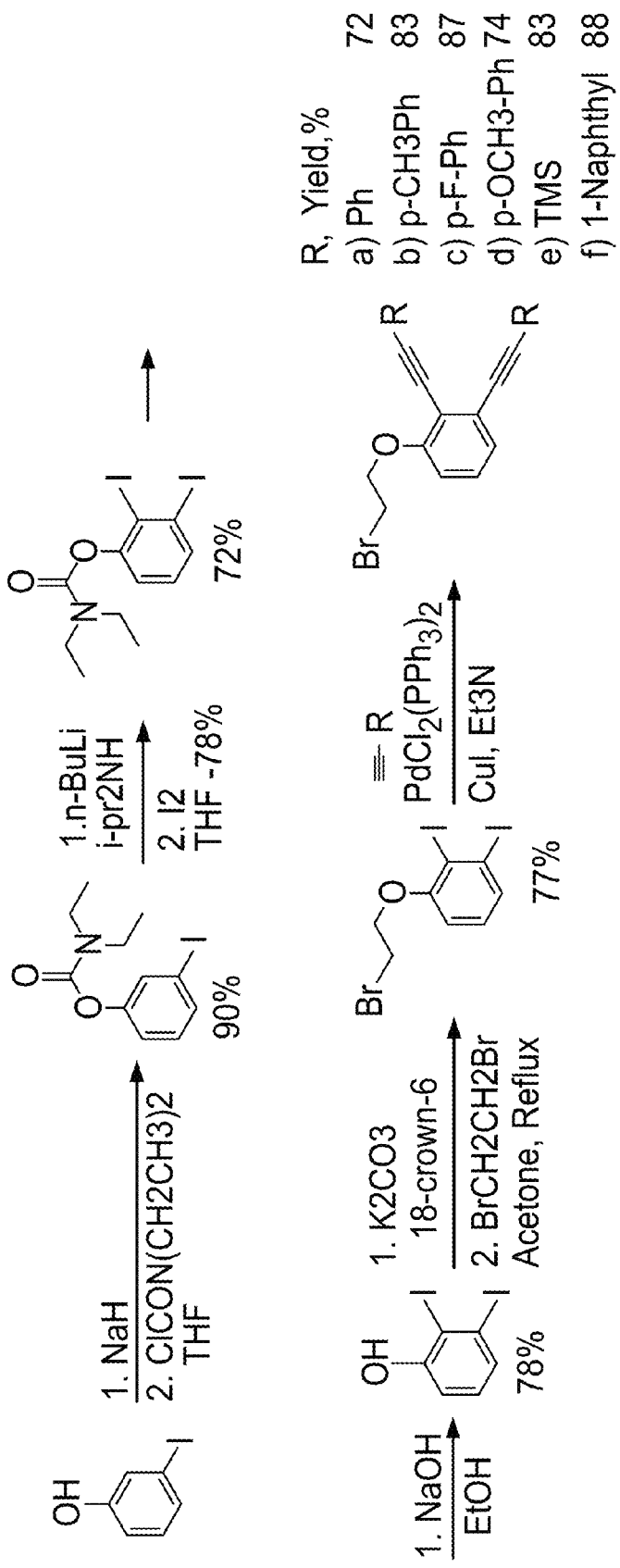
FIG. 3 depicts Scheme 1, which is a sequence of reactions for preparing bis-alkyne model compounds having a moiety representing the "weak link" starting from 3-iodophenol.

Scheme 1 (as depicted in FIG. 3) is a sequence of reactions for preparing bis-alkyne model compounds having a moiety representing the "weak link" starting from 3-iodophenol. The bis-alkyne model compound shown in FIG. 3 having a moiety representing the "weak link" is combined with additional aromatic building blocks to thereby prepare an ortho-poly-alkyne compound having multiple ortho-alkyne moieties, such as at least three ortho-alkyne moieties, preferably at least four alkyne moieties that may be zipped up according to the present invention to thereby prepare graphene ribbons.

According to some embodiments of the present invention, a bis-alkyne model compound having a moiety representing the "weak link" and particularly suitable for preparing oligo-alkyne chains having an odd number of alkyne moieties may have the following general structures (Va) and (vb):

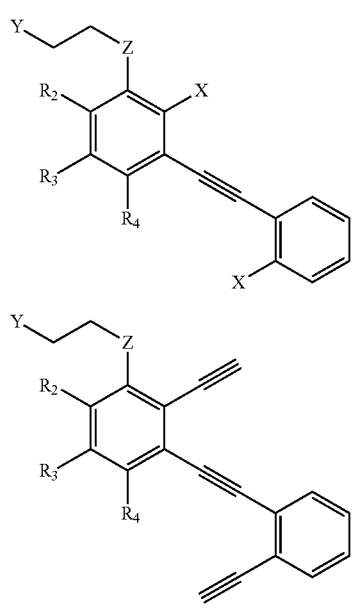

Structure (Va)

Structure (Vb)

In the context of Structures (Va) and (Vb), $R_2$, $R_3$, and $R_4$ have the same definitions as provided in connection with Structure (I). Further, Y and Z have the same definitions as provided in connection with Structure (II).

In the above structure, X comprises a leaving group, such as bromine, iodine, or triflate.

In some embodiments, the aromatic building blocks that may be reacted with the bis-alkyne model compounds having structures (IV) or (V) having a moiety representing the "weak link" may be represented more generally by the following structure (VI):

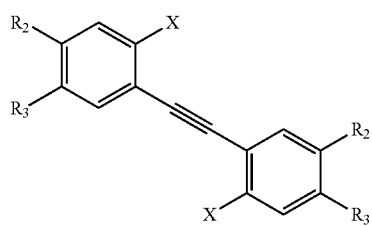

Structure (VI)

In the context of Structure (VI), $R_2$ and $R_3$ have the same definitions as provided in connection with Structure (I). In some embodiments of the above structure (VI), each X independently comprises a leaving group, such as bromine, iodine, or triflate. In some embodiments of structure (VI), each X may independently be an alkyne or a leaving group, such as bromine, iodine, or triflate. In still other embodiments of structure (VI), one X may be hydrogen while the other X may be an alkyne or a leaving group, such as bromine, iodine, or triflate.

Specific examples of building blocks having structure (VI) are shown below as structures (VIa) through (VIe):

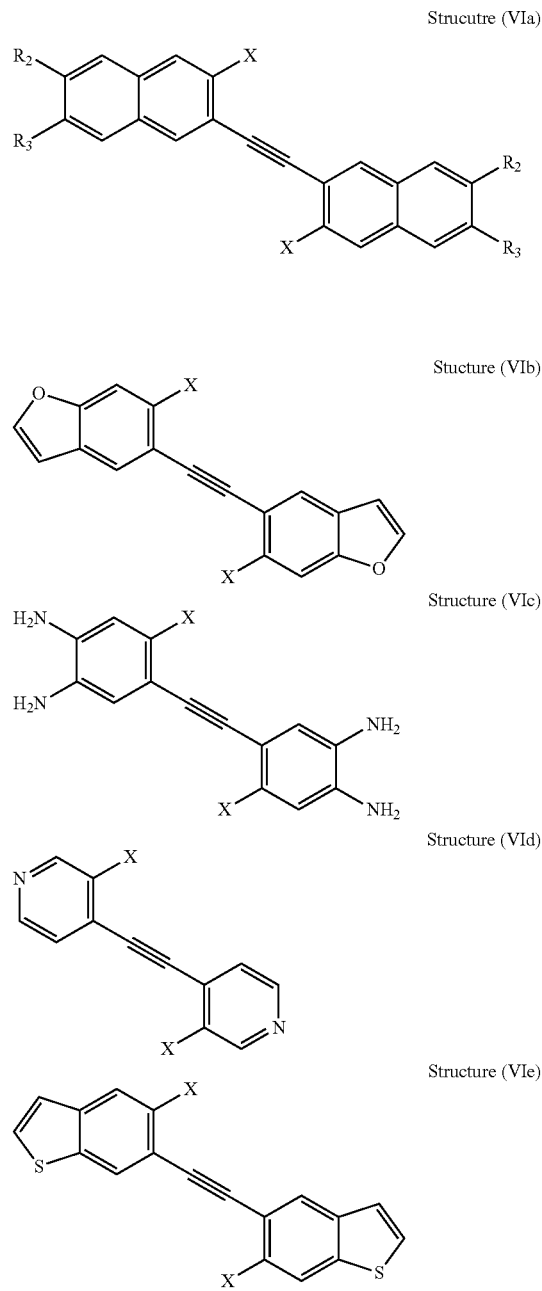

In some embodiments, larger building blocks, e.g., ortho- and poly-alkynes having six, seven, eight, nine, ten or more repeat units when combined e.g., with a model compound having either of structures (IV) or (V), may be built analogously, e.g., by employing building blocks having the following structure (VII):

Structure (VII)

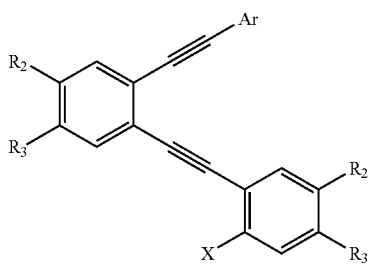

In the context of Structure (VII), $R_2$ and $R_3$ have the same definitions as provided in connection with Structure (I). In the above structure (VII), X comprises a leaving group, such as bromine, iodine, or triflate. X may also be an alkyne. In the above structure (VII), Ar comprises an aromatic group, such as an additional leaving group substituted phenyl group or a toluene. Specific Ar groups include phenyl, para-methylphenyl, para-fluorophenyl, para-methoxyphenyl, and TMS.

Specific examples of building blocks having structure (VII) are shown as below structures (VIIa) through (VIIe):

Structure (VIIa)

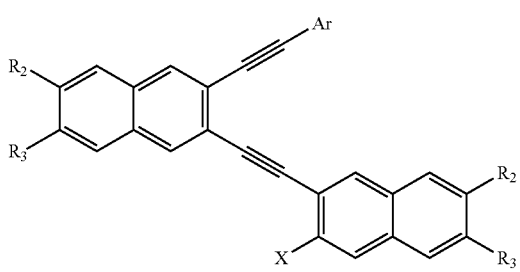

Structure (VIIb)

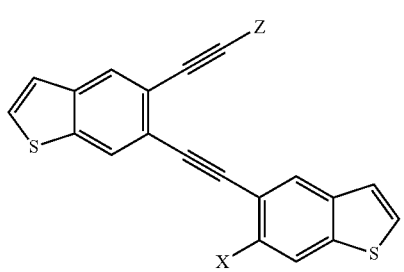

Structure (VIIc)

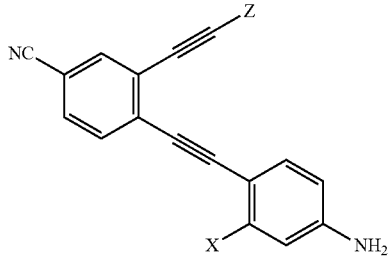

Structure (VIId)

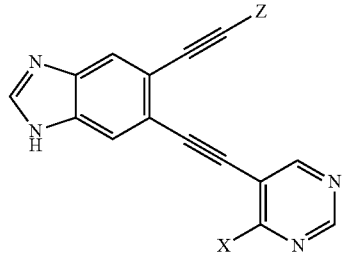

Structure (VIIe)

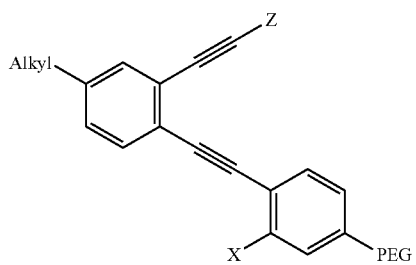

Figure 4:
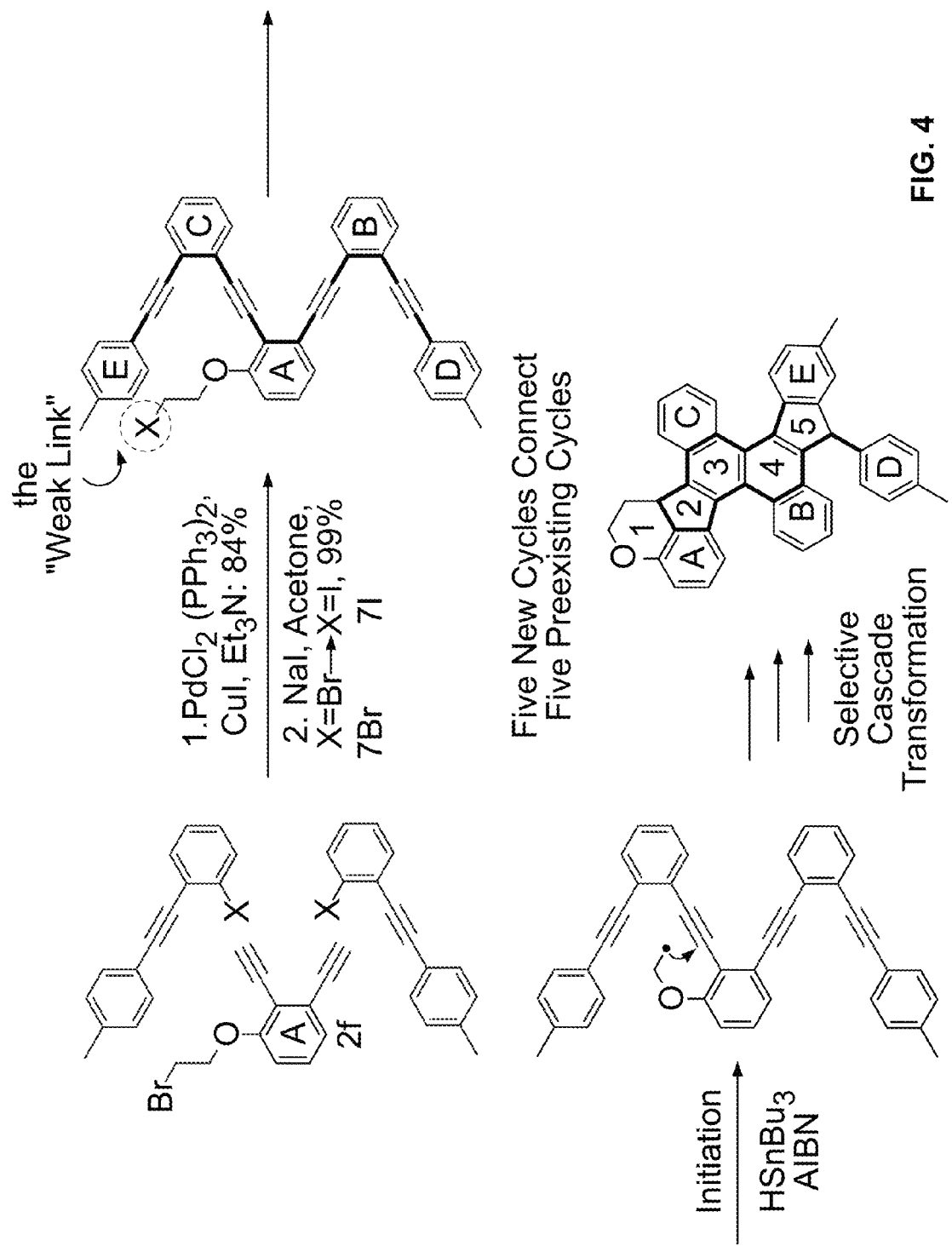
FIG. 4 depicts a sequence of reactions for the modular assembly of bis-alkyne model compounds of the type prepared according to the sequence depicted in FIG. 3 with additional aromatic building blocks to thereby prepare an ortho-poly-alkyne compound having multiple ortho-alkyne moieties.

The above building blocks depicted in structures (IV) through (VII) (and exemplified in specific structures) may be used in the modular assembly of oligo-alkyne and poly-alkynes of the invention. See FIG. 4, which is a sequence of reactions depicting the modular assembly of bis-alkyne model compounds of the type prepared according to the sequence depicted in FIG. 3 with additional aromatic building blocks to thereby prepare an ortho-poly-alkyne compound having multiple ortho-alkyne moieties. In the embodiment depicted in FIG. 4, the oligo-alkyne compound comprises four alkyne moieties. A general structure of an oligo-alkyne compound comprising four alkyne moieties is shown in the following structure (VIII):

Structure (VIII)

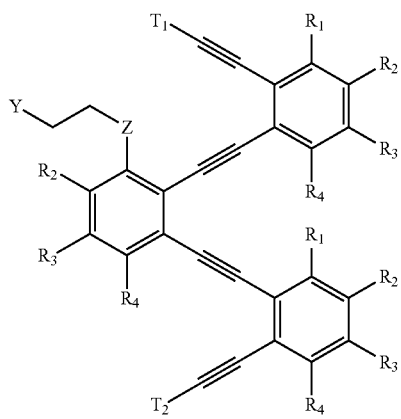

In the context of Structure (VIII), $R_1$, $R_2$, $R_3$, $R_4$, $T_1$, and $T_2$ have the same definitions as provided in connection with Structure (I). Further, Y and Z have the same definitions as provided in connection with Structure (II).

In some embodiments of Structure (VIII), the $T_1$ and $T_2$ moieties may comprise aromatic groups, which may be substituted or unsubstituted. Exemplary aromatic groups include phenyl, toluene, thiophenyl, furanyl, imidazole, and pyridyl, among others. In some embodiments, the $T_1$ and $T_2$ moieties may comprise substituted phenyl groups having the structures:

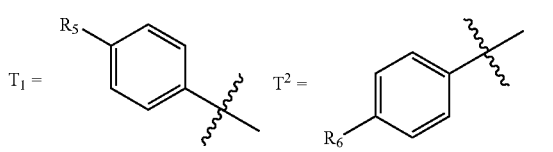

In the above terminating structures, $R_5$ and $R_6$ may be selected from among hydrogen, an aliphatic moiety (e.g., alkyl, alkenyl, alkynyl, cycloalkyl) having from about 1 to about 18 carbon atoms, from 1 to about 14 carbon atoms, or 1 to about 10 carbon atoms, such as 1 to about 6 carbon atoms; an aromatic moiety having from three to 18 carbon atoms, such as from three to 10 carbon atoms (e.g., toluene, naphthyl, para-methoxyphenyl), or six carbon atoms (e.g., phenyl, para-fluorophenyl), or 14 to 20 carbon atoms (anthracene, phenanthrene, alkylanthracene, alkylphenanthrene); an alkoxy moiety having from 1 to about 6 carbon atoms; or a cyano moiety.

Specific examples of oligo-alkynes within the scope of general structure (VIII) are shown below as structures (VIIIa) through (VIIId):

Structure (VIIIa)
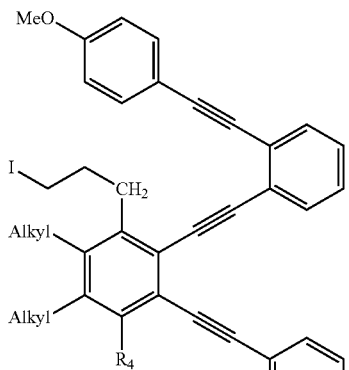

Structure (VIIIb)
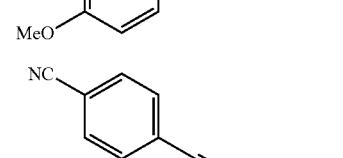
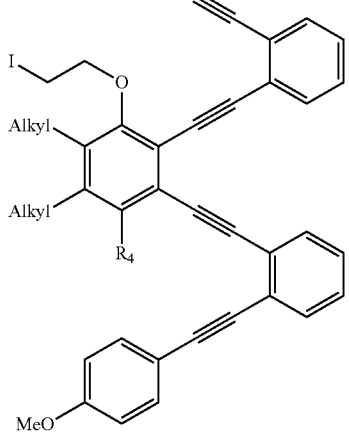

Structure (VIIIc)
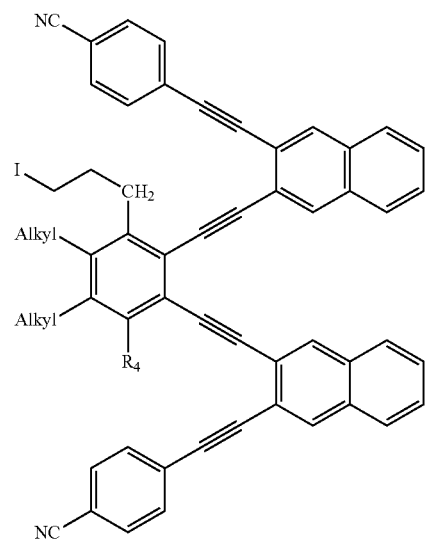

Structure (VIIId)
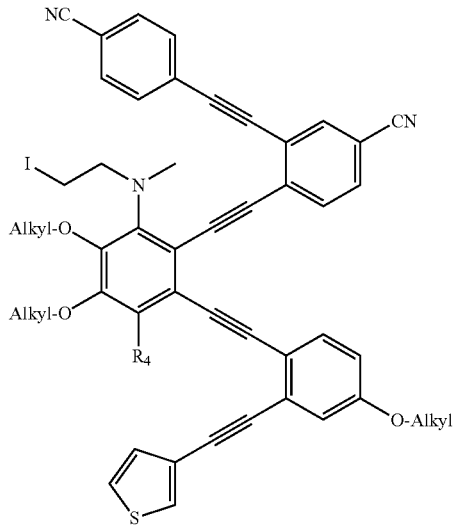

In each of structure (VIIIa), structure (VIIIb), structure (VIIIc), and structure (VIIId), the alkyl moiety may comprise from 1 to 18 carbon atoms, such as from 1 to 12 carbon atoms, from 1 to 6 carbon atoms, or from 1 to 4 carbon atoms, such as methyl, ethyl, n-propyl, isopropyl, n-butyl, isobutyl, tert-butyl, and so on.

The model compounds, e.g., the bis-alkyne model compound having structure (IV) based on the starting moiety representing the "weak link" and modularly built with additional aromatic building blocks, e.g., having structure (VII), shown above may be depicted in the below ortho poly-alkyne chain structure (IX) having at least six alkynes:

Structure (IX)

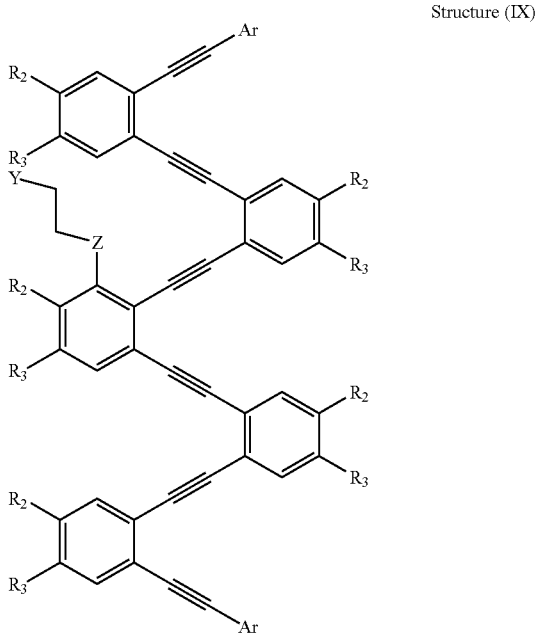

In the context of Structures (IX), $R_2$ and $R_3$ have the same definitions as provided in connection with Structure (I). Further, Y and Z have the same definitions as provided in connection with Structure (II). In the above structure, Ar comprises an aromatic group, such as an additional leaving group substituted phenyl group or a toluene.

Larger structures may be built in the same modular fashion, having, e.g., a chain of eight alkyne moieties, a chain of 10 alkyne moieties, a chain twelve alkyne moieties, or still larger, such as 14, 16, 18, 20, 22, or 24 alkyne moieties. In some embodiments, the structures may comprise oligo-alkynes having odd numbers of alkynes, such as three alkyne moieties, five alkyne moieties, seven alkyne moieties, nine alkyne moieties, or still larger, such as 11, 13, 15, 17, 19, 21 or 23 alkyne moieties. These modularly built ortho-poly-alkyne structures comprising a central "weak link" moiety may be subjected to radical cyclizations to thereby prepare highly cyclized compounds. In preferred embodiments, the cyclization is carried out using Sonogashira coupling. The Sonogashira reaction is a palladium catalysed carbon-carbon bond forming reaction between an aryl halide (e.g. Br, I) and a terminal alkyne moiety (e.g. HCCR). A general procedure involves a suspension of aryl halide, $PdCl_2(PPh_3)_2$, Cu(I) iodide in a amine solvent (triethylamine or diisopropy-lamine). The solvent is degassed to remove the majority of oxygen possibly in the solution which can catalyze a non desirable Hay homocoupling side reaction. Once the solution is degassed, alkyne is added and the reaction is initiated.

Figure 5:
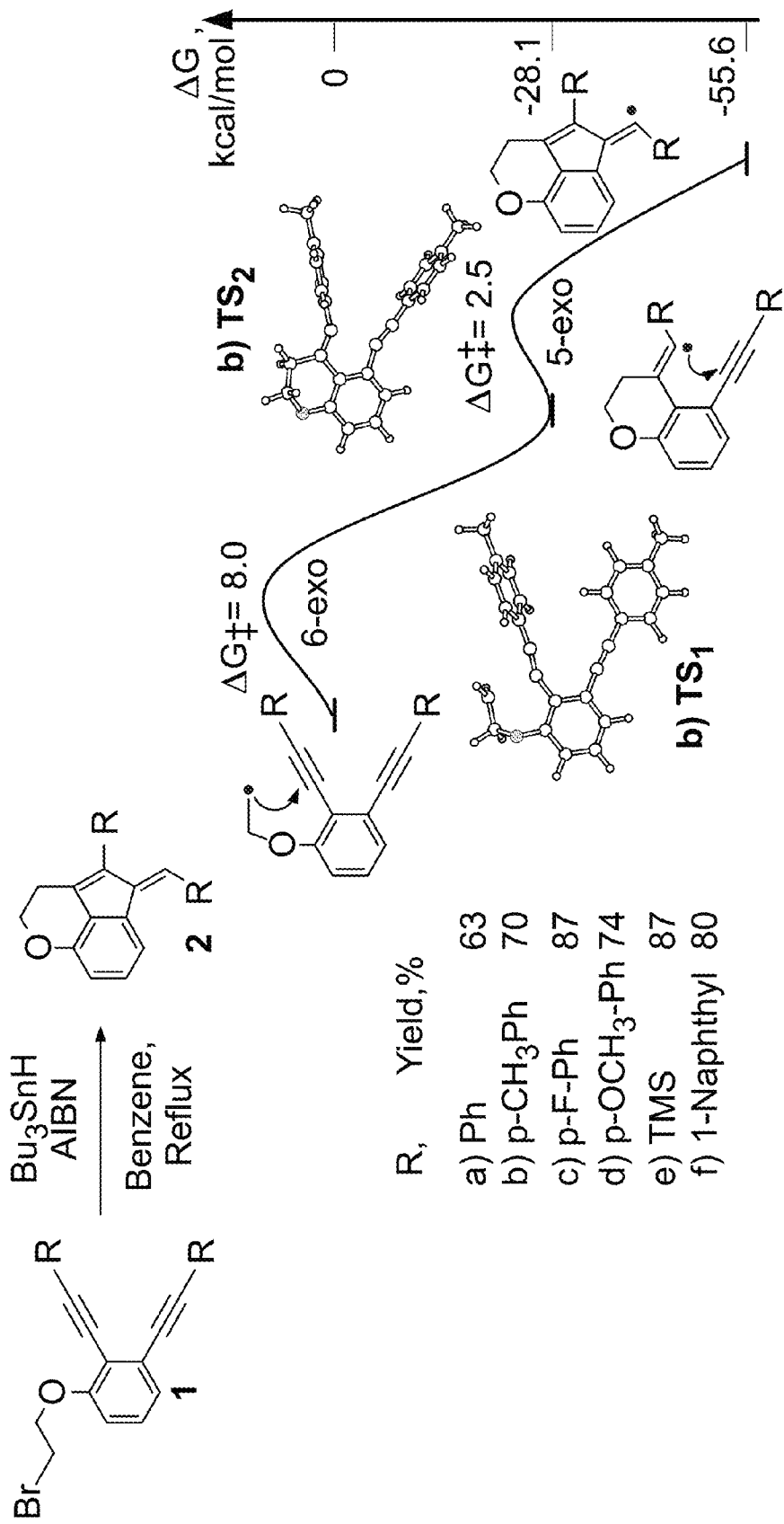
FIG. 5 depicts the Scheme 2 sequence of cascade cyclization of substituted enediynes and PES for the transformation of enediyne 2b (B3LYP/6-31+(d,p), kcal/mol).

Initial cyclization efforts using the bis-alkyne model compounds having a moiety representing the "weak link" using silane-mediated processes ($Et_3SiH$ and TTMSS) led to the products of the desired cascade transformation. However, the reactions were sluggish and the yields were low (21-25%). A dramatic increase in efficiency was observed when the $Bu_3SnH$/AIBN system was used for the chemoselective cascade initiation. The chemoselective radical attack at the alkyl halide in the presence of two alkynes is remarkable considering that alkynes are also reactive under these conditions. See Scheme 2, which is depicted in FIG. 5. Scheme 2 depicts cascade cyclization of substituted enediynes and Potential Energy Surface (PES) for the transformation of enediyne 2b (B3LYP/6-31+(d,p), kcal/mol).

Figure 6:
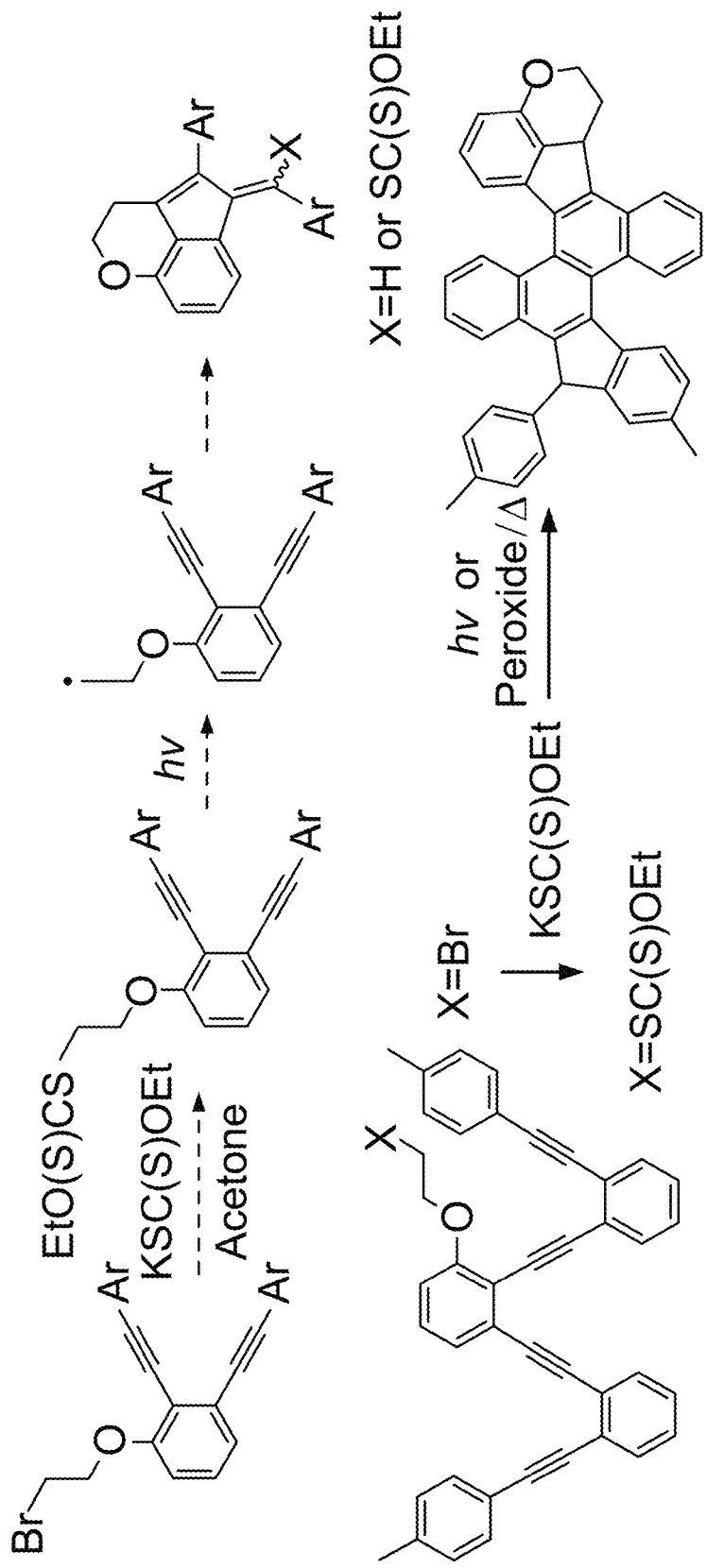
FIG. 6 depicts Scheme 3, which is a sequence of selective radical initiation through the use of xanthate as the weak link in a tetra-alkyne reactant.

In view of these results, a one-pot cyclization of the tetra-alkyne 11 was developed as shown in Scheme 3 (FIG. 6). The transformation proceeded as expected and formed the fully "zipped" cascade product. Although the yield was low for X=Br (26%), the bromide can be quantitatively exchanged to form the iodo tetraalkyne 12 which is transformed in the fully closed nanoribbon 13 in a much higher yield (52% overall, ~93% per step).

Figure 7:
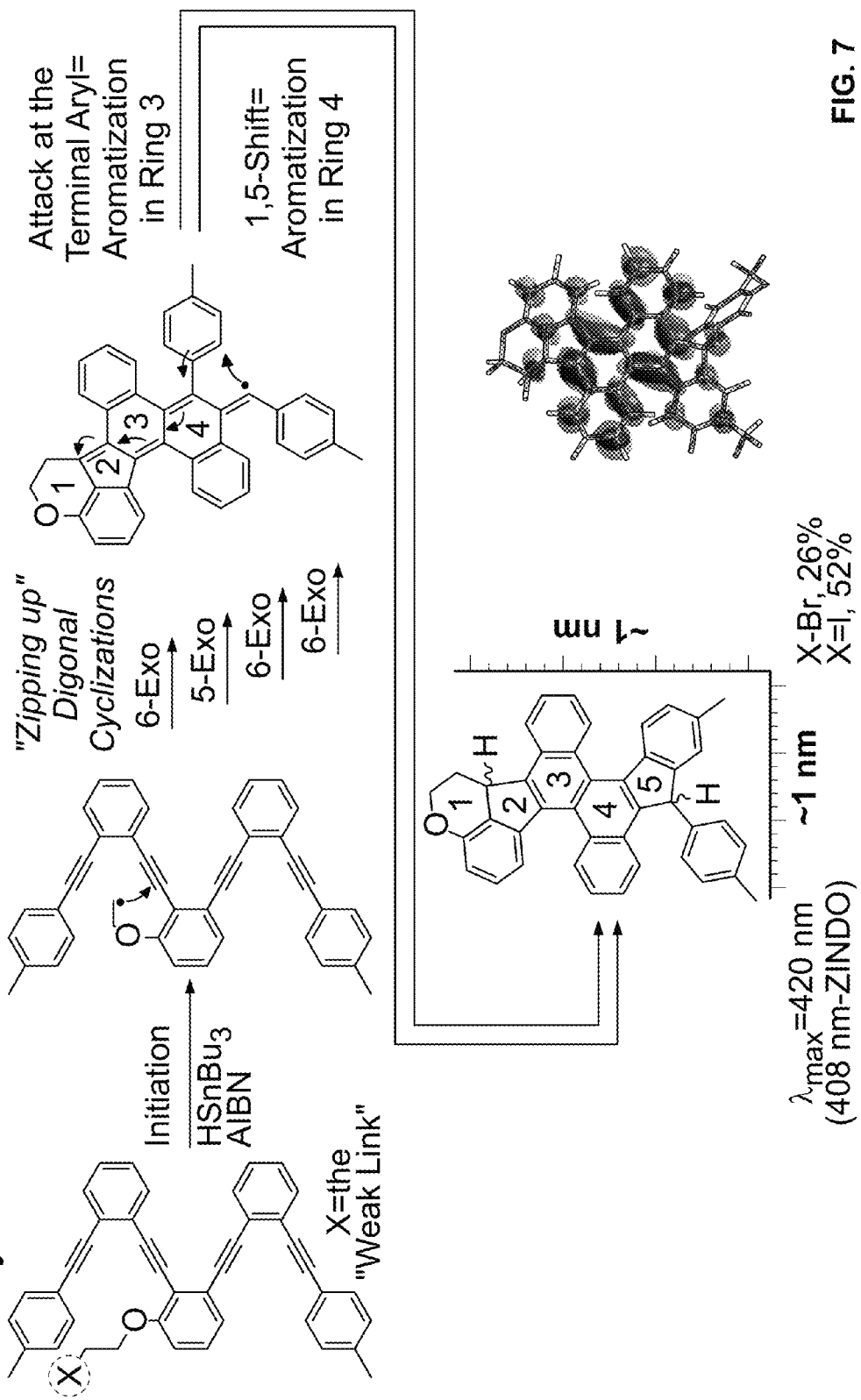
FIG. 7 depicts Scheme 4, which is a sequence of reactions for the synthesis of o-aryleneethynylene tetramer, the mechanism of cascade cyclization, and the highest occupied molecular orbital (HOMO) of the product.

Once selective activation of the "weak link" in the presence of four alkynes is accomplished, a cascade of four sequential exo-dig alkyne cyclizations occurs. Only after all four alkynes are consumed by the radical cascade does the vinyl radical attack the terminal aryl ring. This attack transiently disrupts aromaticity in this ring and is only observed when three or more alkynes are present in the starting material. For these longer oligomers, this transient loss of aromaticity is partially compensated by the aromatization in one of the previously formed rings (i.e., ring 3, Scheme 4 (depicted in FIG. 7)). The 1,5 H-shift is also favorable because it is assisted by rearomatization. The final H-abstraction step has low stereoselectivity because of near planarity of the sterically unencumbered radical center.

The noticeable increase in the efficiency of the iodo-substituted tetrayne ring closure (Br: 26%, I: 52%) suggests that the initiation step plays a key role in the success of the overall cascade. Selectivity may be further improved as the number of alkynes increase or when new functional groups are introduced via the optimization of the "weak link." In aspect, a promising alternative to the choice of the "weak link" is provided by xanthates. In view thereof, the bromide or iodide moiety in the weak link structure may be replaced with a xanthate structure, as shown in Scheme 3 (FIG. 6), prior to cyclization. Xanthates can be selectively activated in the presence of alkyne using either light or lauroyl peroxide/thermal initiation. Photochemical activation is particularly appealing because it is chemically orthogonal to the radical processes discussed above and has the potential to be more selective.

Figure 8:
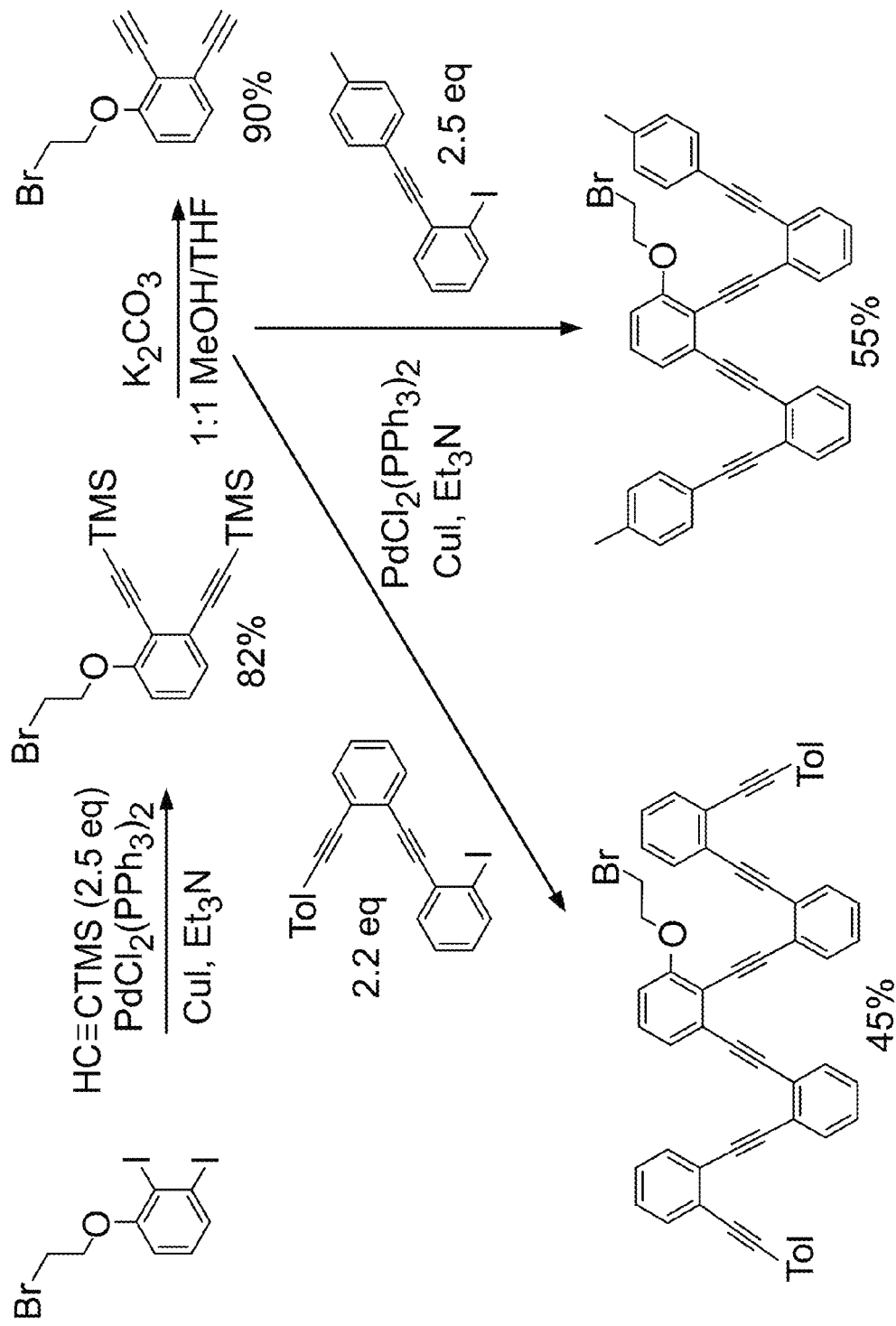
FIG. 8 depicts synthesis of oligo-alkynes with an even number of alkyne moieties using a "linchpin" with two alkynes
Figure 9:
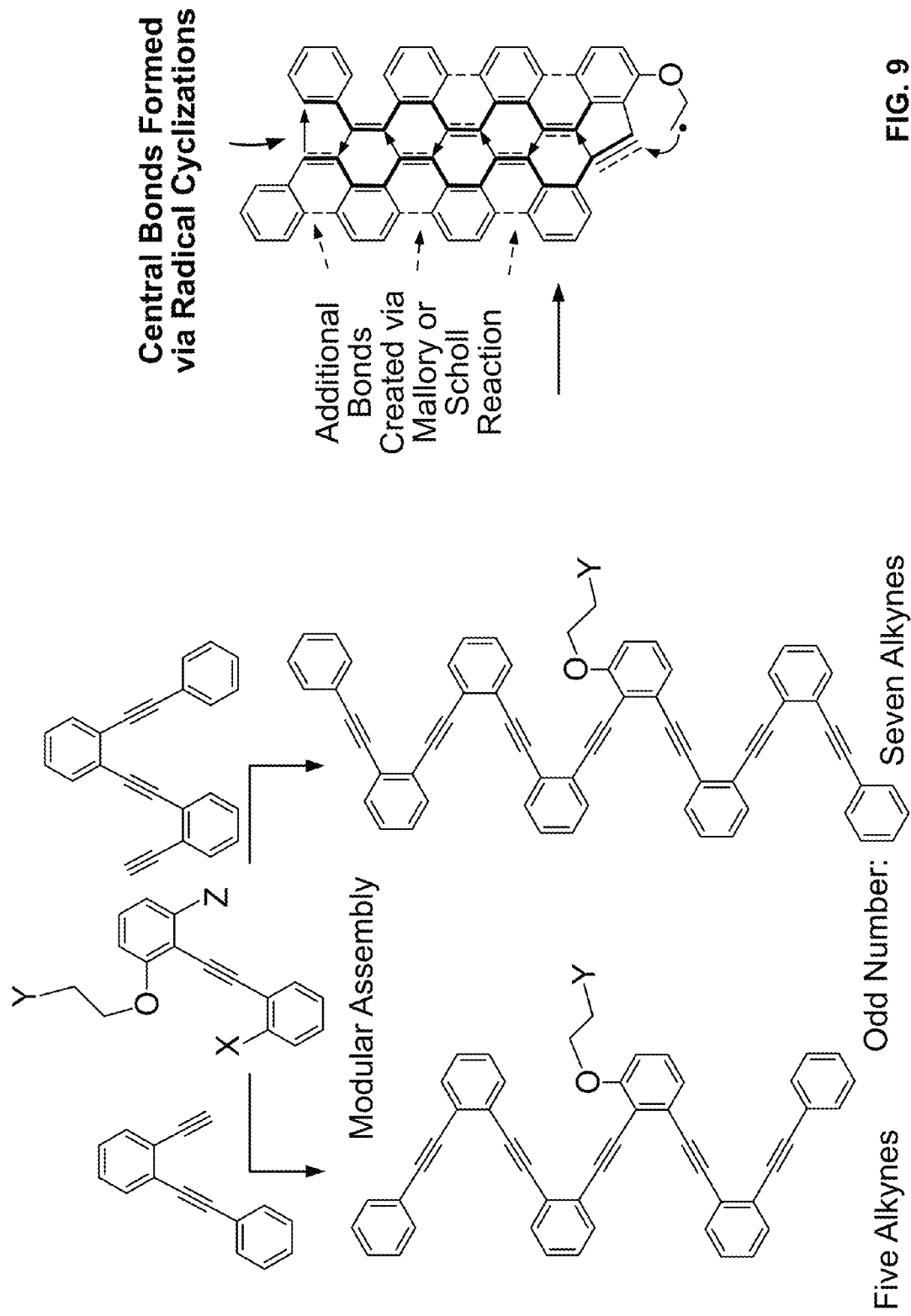
FIG. 9 depicts synthesis of oligo-alkynes with an odd number of alkyne moieties using a monoalkyne "linchpin" (or any other core molecule with an odd number of alkynes).

The synthesis of longer and wider ribbons leads towards the synthesis of nanoribbon pieces with a number of materials applications. Assembly of symmetric alkynes is particularly fast and is further facilitated using a library of the most common building blocks. A "linchpin" with two alkynes provides poly-alkynes with an even number of alkyne moieties. See FIG. 8. Starting with a monoalkyne "linchpin" (or any other core molecule with an odd number of alkynes) provides symmetric molecules with an odd number of alkyne moieties. See FIG. 9. However, all oligo-alkynes, independent on having an odd or an even number of the triple bonds, can be fully converted to a polyaromatic molecules as long as the initiating step occurs at the central alkyne.

Figure 10:
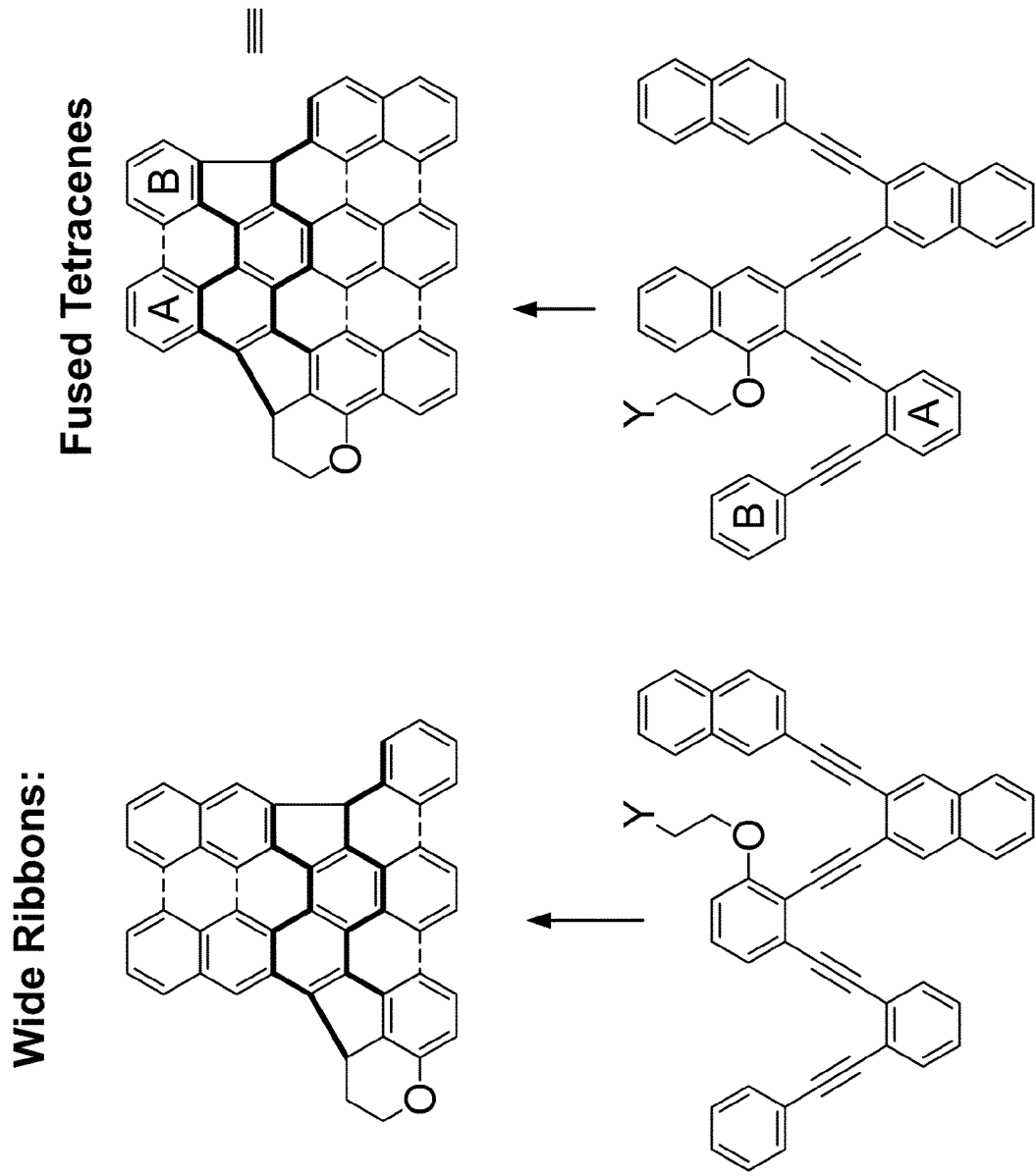
FIGS. 10 and 11 depict the modular approach to the synthesis of wider graphene ribbons when naphthalenes or anthracenes are used instead of preexisting benzene rings in the reactants.
Figure 11:
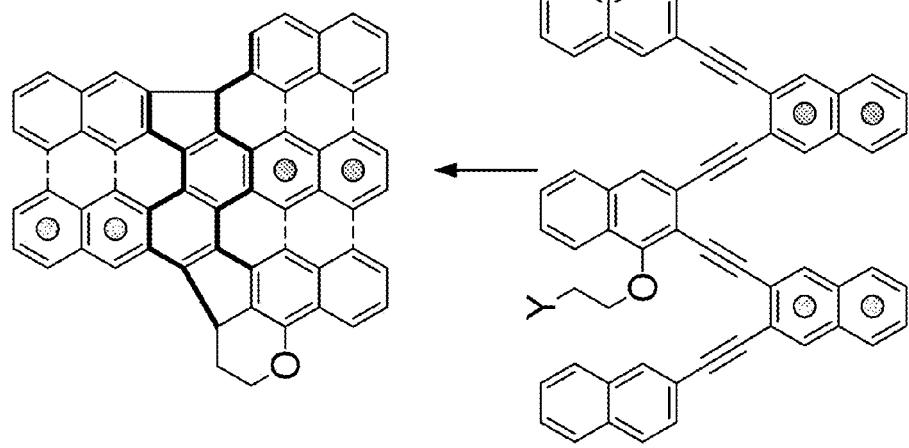
Figure 11:
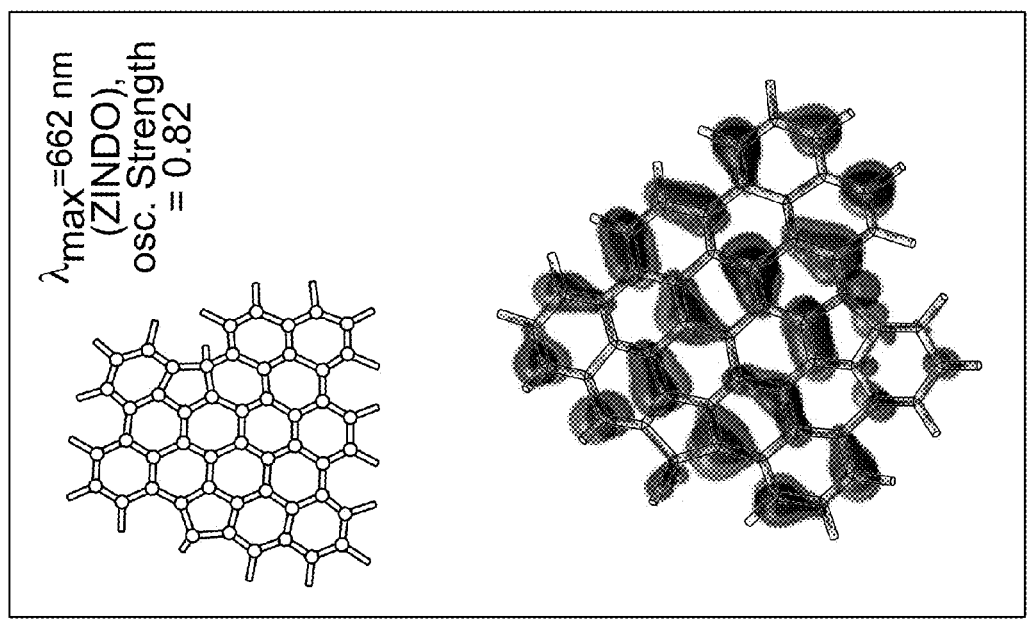

In some embodiments, the alternative for increasing molecular dimensions in the 2D space is to make the ribbons wider. Wider ribbons are available when naphthalenes or anthracenes are used instead of preexisting benzene rings in the reactants. See FIGS. 10 and 11. In some embodiments, wider ribbons are possible by cyclizing oligo-alkynes having the general structure (X):

Structure (X)

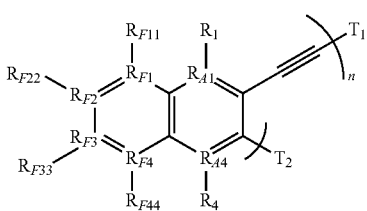

$R_1$, $R_4$, $R_{A1}$, $R_{A4}$, $T_1$, $T_2$, and n are as defined in connection with the definitions of each provided in Structure (I).

$R_{F1}$, $R_{F2}$, $R_{F3}$, $R_{F4}$ are each independently carbon Or nitrogen. In some embodiments, $R_{F1}$, $R_{F2}$, $R_{F3}$, $R_{F4}$ comprises from 1 to four carbon atoms. In some embodiments, $R_{F1}$, $R_{F2}$, $R_{F3}$, $R_{F4}$ comprises from 1 to four nitrogen atoms. Accordingly, the aromatic moiety within structure (IX) may be any of naphthalene, quinolone, isoquinoline, quinoxaline, benzo[d][1,2,3]triazine, benzo[e][1,2,4]triazine, 1,5-naphthyridine, 1,6-naphthyridine, 1,7-naphthyridine, 1,8-naphthyridine, phthalazine, pyrido[2,3-d]pyridazine, pyrido[3,4-d]pyridazine, among others. The modular assembly of such compounds enables the preparation of ortho oligo- or poly-alkyne compounds of the present invention in which each repeat unit has an identical aromatic ring structure. The modular assembly alternatively allows preparation of compounds in which each repeat unit has a different aromatic ring structure. For example, in some embodiments, all of the aromatic rings in the repeat unit may comprise naphthalene groups, which may be substituted or unsubstituted. In some embodiments, all of the aromatic rings in the repeat unit may comprise, e.g., quinolone or phthalazine rings, which may be substituted or unsubstituted. In still other embodiments, combinations of these groups are possible. Furthermore, each aromatic ring may comprise different substituents. For example, some aromatic rings may be substituted with cyano, while other aromatic rings may be substituted with alkoxy.

In some embodiments of the above structure (X), $RF_{11}$, $RF_{22}$, $RF_{33}$, $RF_{44}$ are each independently hydrogen; an election pair (i.e., when the corresponding ring atom is nitrogen); an aliphatic moiety; an aromatic moiety; an alkoxy moiety; cyano; nitro; sulfonyl; sulfonyl; amino; or an alkylamino. Each repeat unit of structure (I) may comprise different substituents at the $R_1$, $R_2$, $R_3$, and $R_4$ positions. The aliphatic moiety (e.g., alkyl, alkenyl, alkynyl, cycloalkyl) may have from 1 to 18 carbon atoms, or from 1 to about 14 carbon atoms, or 1 to about 10 carbon atoms, such as 1 to about 6 carbon atoms. The aromatic moiety having from three to 18 carbon atoms, such as from three to 10 carbon atoms, or three to six carbon atoms. The alkoxy moiety having from 1 to about 6 carbon atoms, such as from 1 to about 3 carbon atoms. The alkylamino may have from 1 to 18 carbon atoms, or from 1 to about 14 carbon atoms, or 1 to about 10 carbon atoms, such as 1 to about 6 carbon atoms. The aliphatic moiety, aromatic moiety, alkoxy, or alkyl amino moiety may be substituted or unsubstituted. Substituents include halogen (e.g., chlorine, bromine, or iodine), amino, xanthyl, or cyano.

In some embodiments of the above structure (X), the $R_{F11}$, $R_{F22}$, $R_{F33}$, $R_{F44}$ together with the atoms to which they are bonded may form a fused cycloalkyl (which may be homocycloalkyl or heterocycloalkyl) or aromatic ring (which may be homoaromatic, such as phenyl, or heteroaromatic) or multiple fused aromatic rings. Fused heterocycloalkyl and heteroaromatic moieties may comprise nitrogen (e.g., pyridyl, pyridazinyl, triazinyl), sulfur (e.g., thiophenyl, thiophene, benzothiophene), or oxygen (e.g., furanyl, tetrahydrofuranyl).

An exemplary embodiment which may be used to prepare wide ribbons is shown in the following structure (Xa):

Structure (Xa)

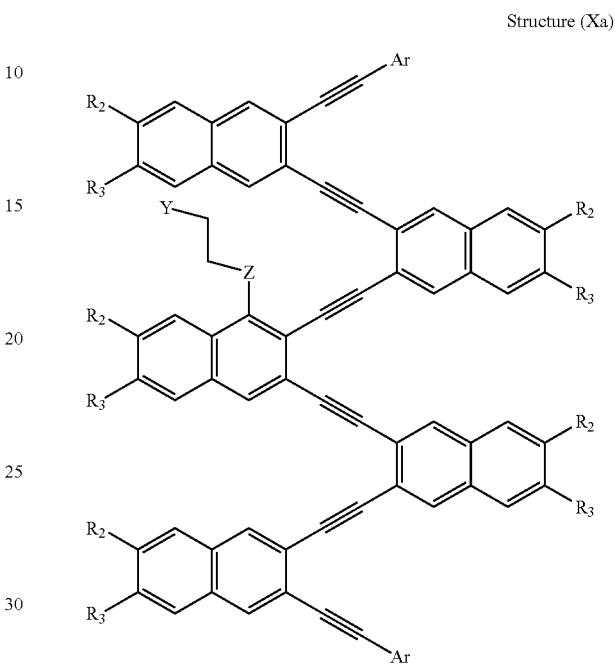

$R_1$, $R_2$, $R_3$, $R_4$, $T_1$, $T_2$, Y, and Z are as defined above in connection with structures (I) and (II).

The modular approach to the construction of poly-alkynes should allow significant flexibility. Use of naphthalenes allows preparation of either anthracene/naphthalene fusions (naphthalenes on one side of the ribbon=one extra layer hexagons) or anthracene/anthracene fusions (naphthalenes on both sides of the ribbon=two extra layers of pentagons). The prepared ortho-poly-alkyne chains may be cyclized and dehydrogenated (vide infra) in order to use these processes to provide fused tetracenes and pentacenes. In principle, fused pentacenes can be also prepared from antracene containing oligoynes (not shown). Pentacene itself is an organic semiconductor and valuable electronic material.

Because a variety of acetylenic building blocks can be introduced in the poly-alkyne precursor via the robust Pd-catalyzed cross-coupling approach and because the efficiency of exo-dig cyclizations is not affected strongly by the nature of the aromatic substituents, the chemistry lends itself for introducing and fine-tuning a variety of electronic effects in graphene nanoribbons and graphene substructures. Functionalization on the outside of the graphene core will change its electronic properties and will open up new opportunities for the incorporation of these functionalities into supramolecular assemblies. An additional possibility for introducing substituents is to replace terminal aryl group by the needed functionality.

Figure 12A:
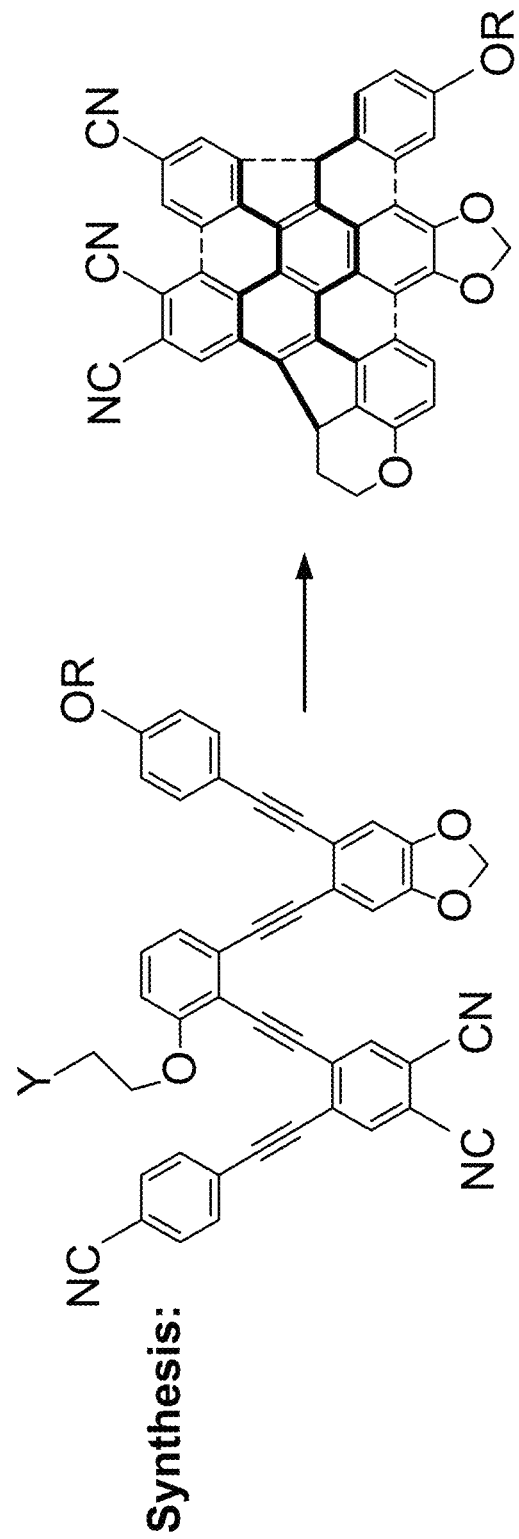
FIGS. 12A through 12E depict Scheme 5, which provides a sequence of reactions for preparing highly cyclized structures with both cyano and alkoxy (methoxy and 1,3-dioxolane) functionality.
Figure 12B:
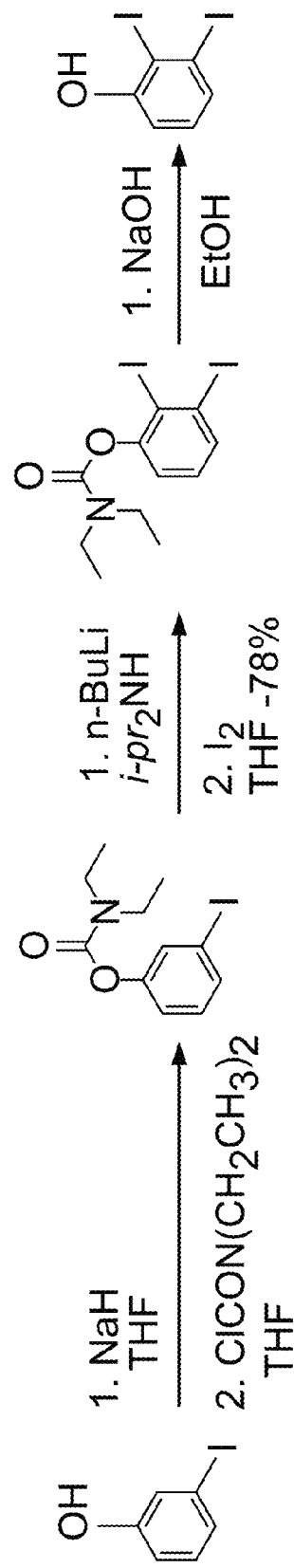
Figure 12B:
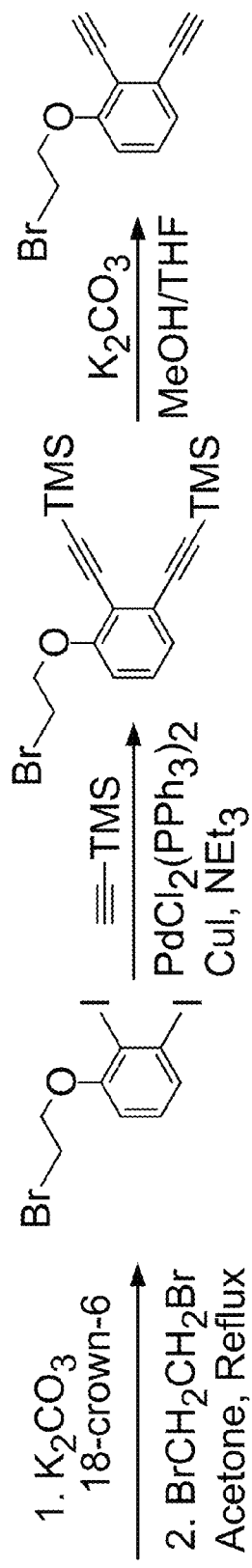
Figure 12C:
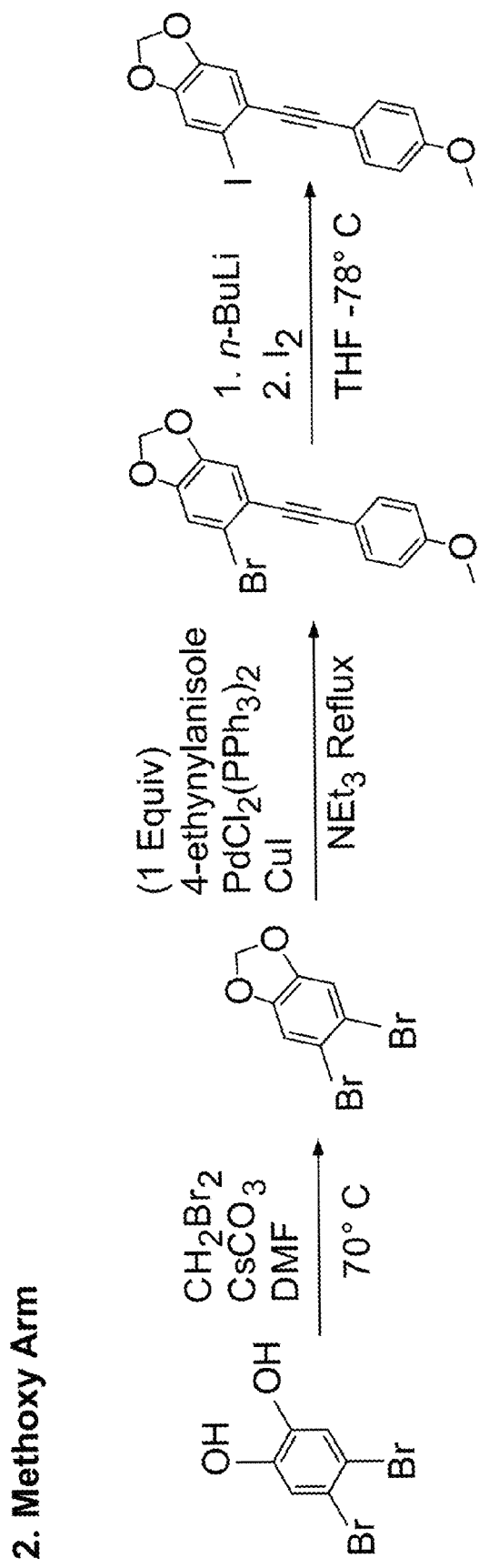
Figure 12D:
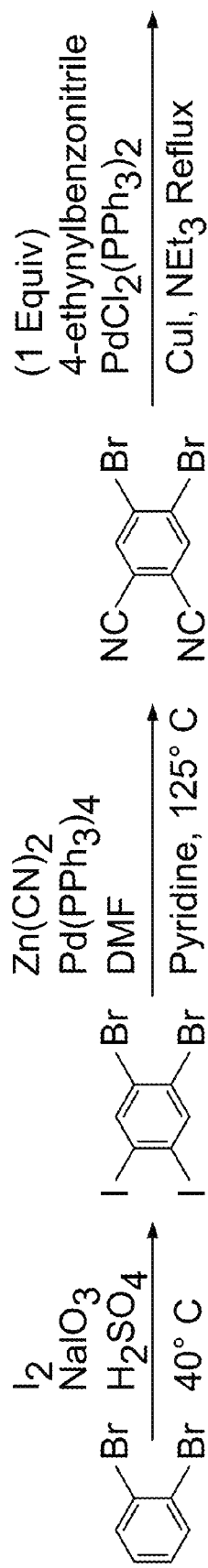
Figure 12D:
Figure 12E:
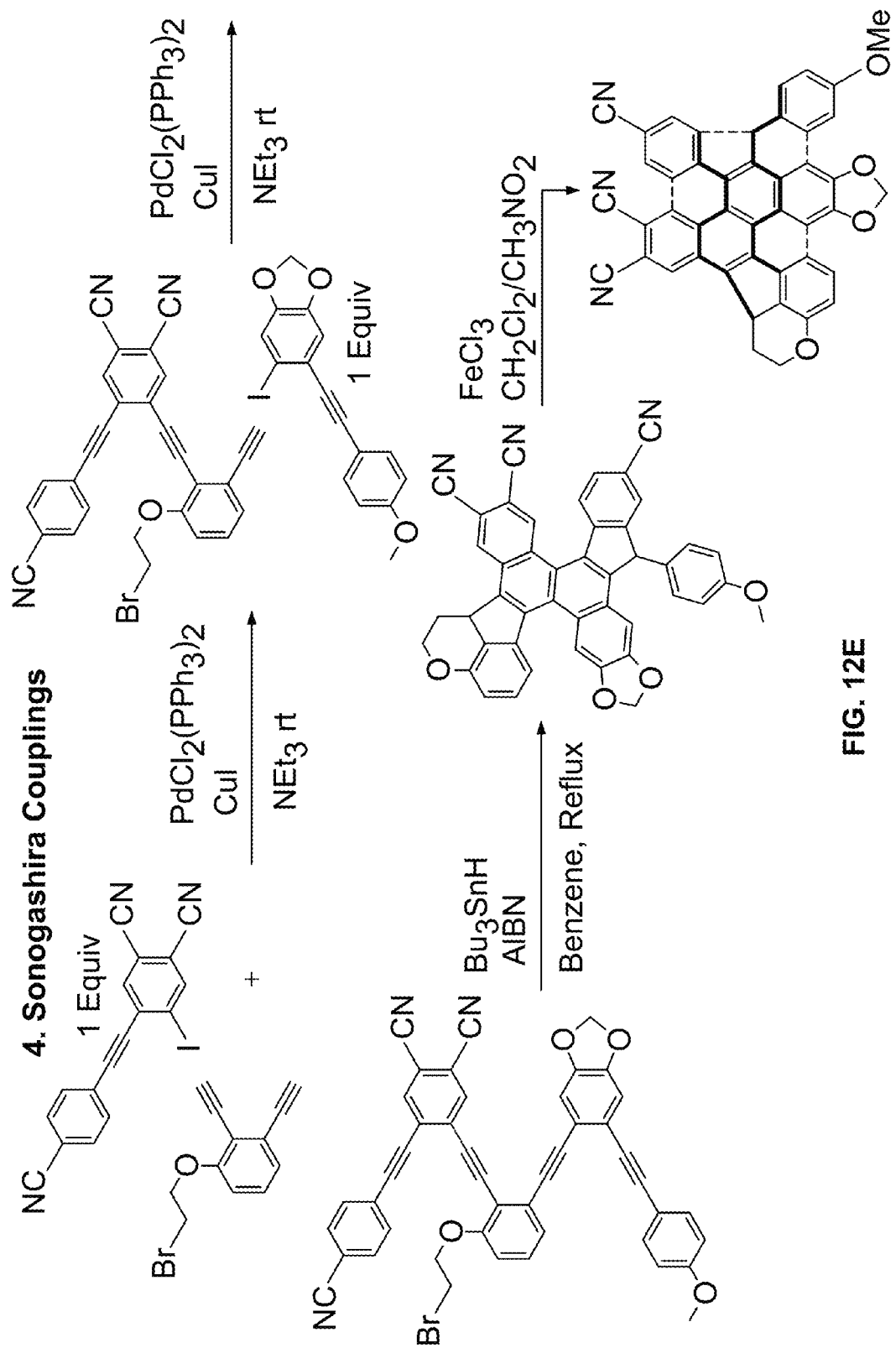

Cyclizations of bis-alkynes (enediynes) show that both the cyano and the alkoxy groups are fully compatible with the radical cascade conditions. See FIGS. 12A through 12E (Scheme 5). FIG. 12A depicts the final oligo-cyclization for preparing a highly cyclized structure with both cyano and alkoxy (methoxy) functionality. The synthesis of the component parts of the compound are provided in FIGS. 12B through 12D. The Songashira coupling reactions are provided in FIG. 12E, including the conditions for cyclization of the assembled compound.

In some embodiments, the present invention is directed to the cyclization of heteroaromatic assemblies. For example, the present invention is directed to the synthesis of heteroaromtic assemblies, followed by cyclization to thereby prepare highly cyclized conjugated polyheteroaromatic nanostructures. Building block assemblies, according to these embodiments of the present invention, may be based on heteroaromatic compounds including pyridine, pyrazine, pyrimidine, pyridazine, triazines, and tetrazines.

In some embodiments, the oligo-alkyne of the present invention may comprise repeat units having the following general structures (XI) or (XII):

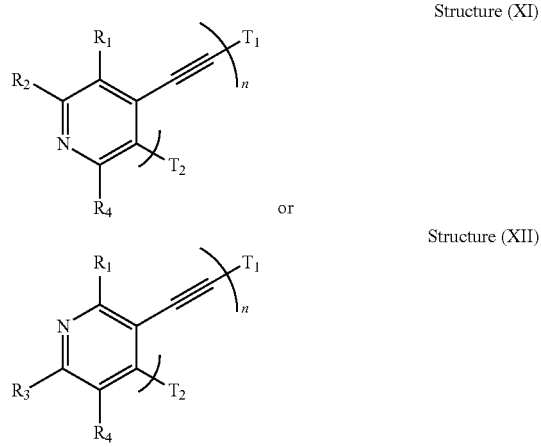

Structure (XI)

or

Structure (XII)

In the above structures, $R_1$, $R_2$, $R_3$, $R_4$, $T_1$, $T_2$, and n are as defined in connection with Structure (I). Modular assembly enables the preparation of oligo-alkynes combining the repeat units of both Structures (XI) and (XII). Still further, the oligo-alkynes may be prepared using the repeat units shown in Structures (III), (X), (XI), and (XII).

In another embodiment, the oligo-alkyne of the present invention may have the following general structure (XIII):

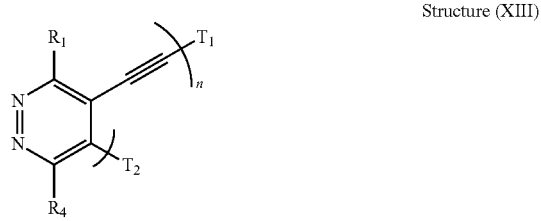

Structure (XIII)

In the above structures, $R_1$, $R_4$, $T_1$, $T_2$, and n are as defined in connection with Structure (I). Modular assembly enables the preparation of oligo-alkynes combining any of the repeat units of Structures (XI), (XII), and (XIII). Still further, the oligo-alkynes may be prepared using the repeat units shown in Structures (III), (X), (XI), (XII), and (XIII).

Figure 13:
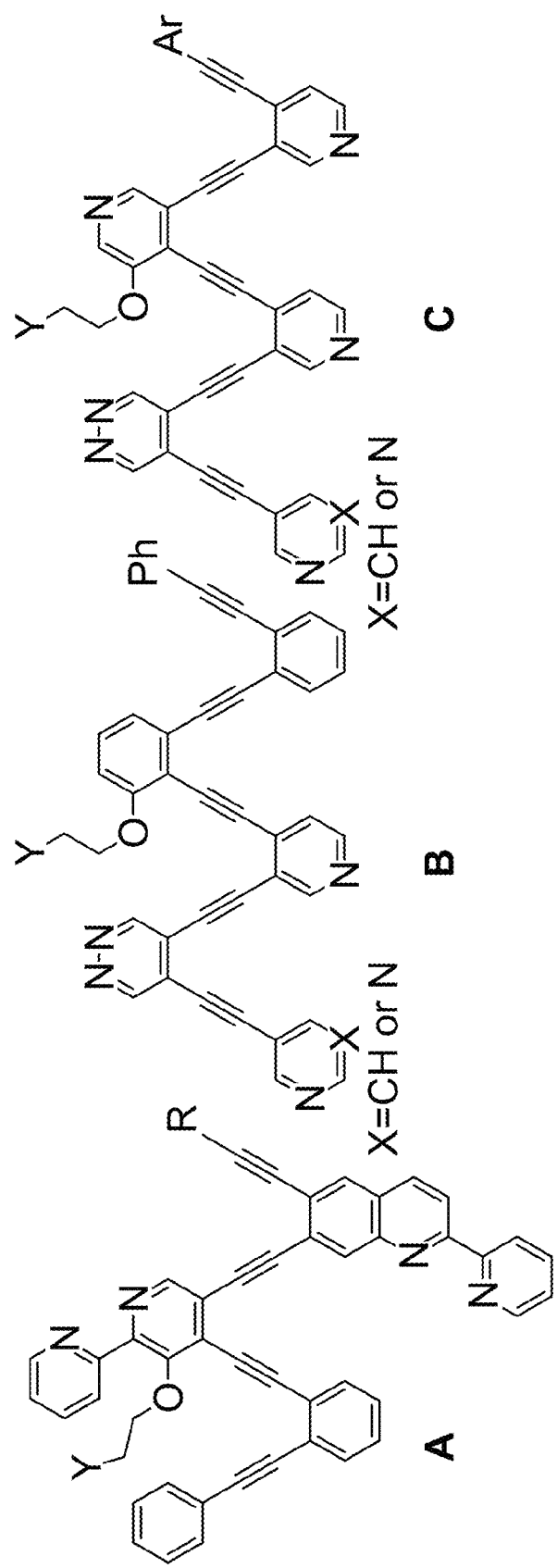
FIG. 13 depicts oligo-alkyne compounds based on heteroaromatic building blocks
Figure 14A:
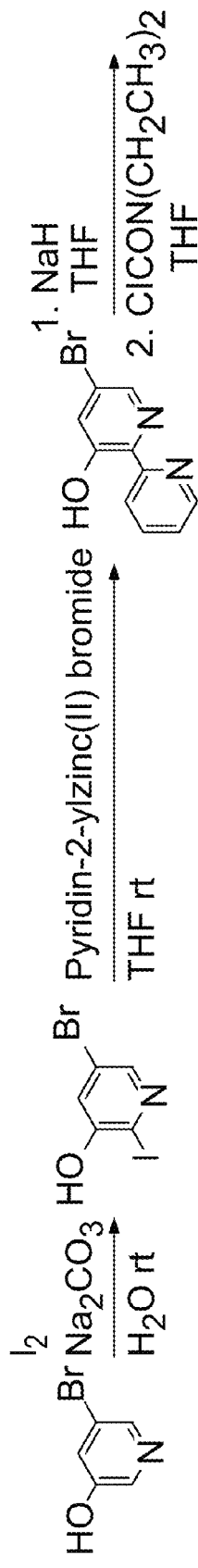
FIGS. 14A through 14D depict the synthetic scheme for the preparation of oligo-alkyne of compound A of FIG. 13.
Figure 14A:
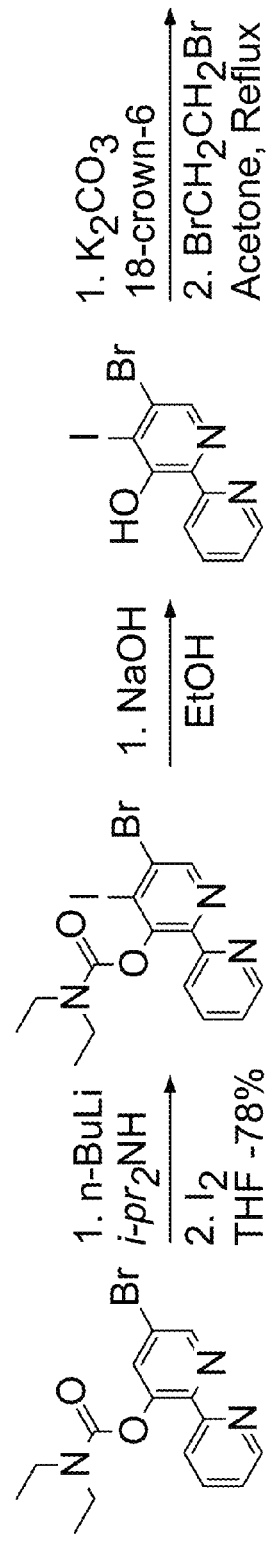
Figure 14A:
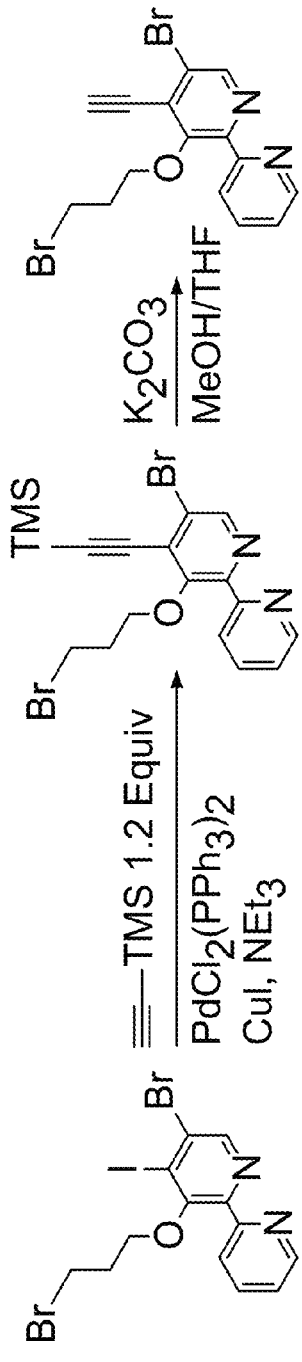
Figure 14B:
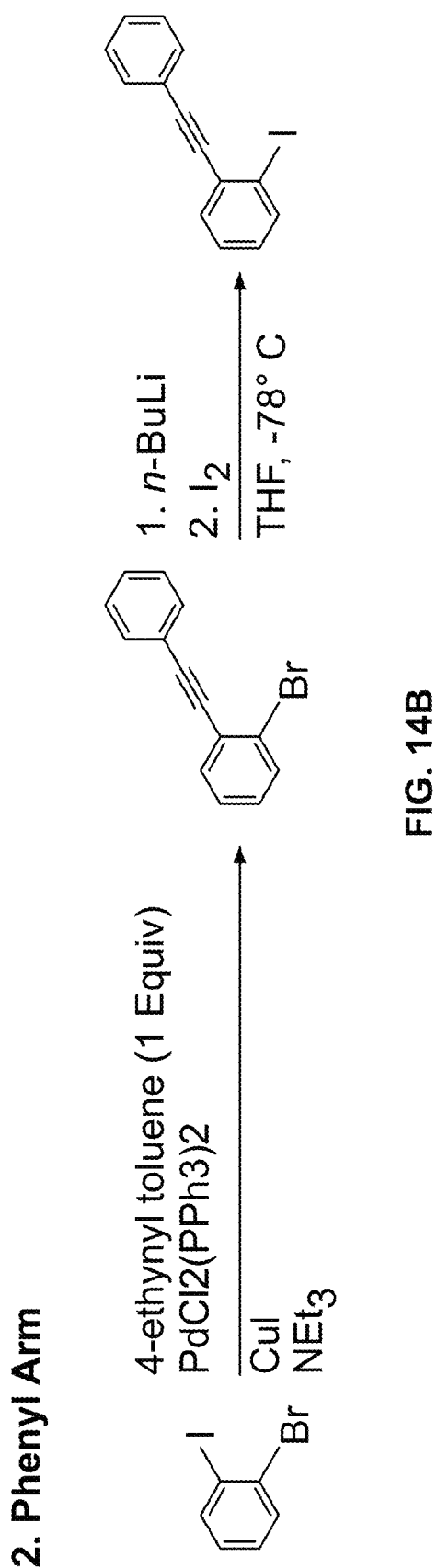
Figure 14C:
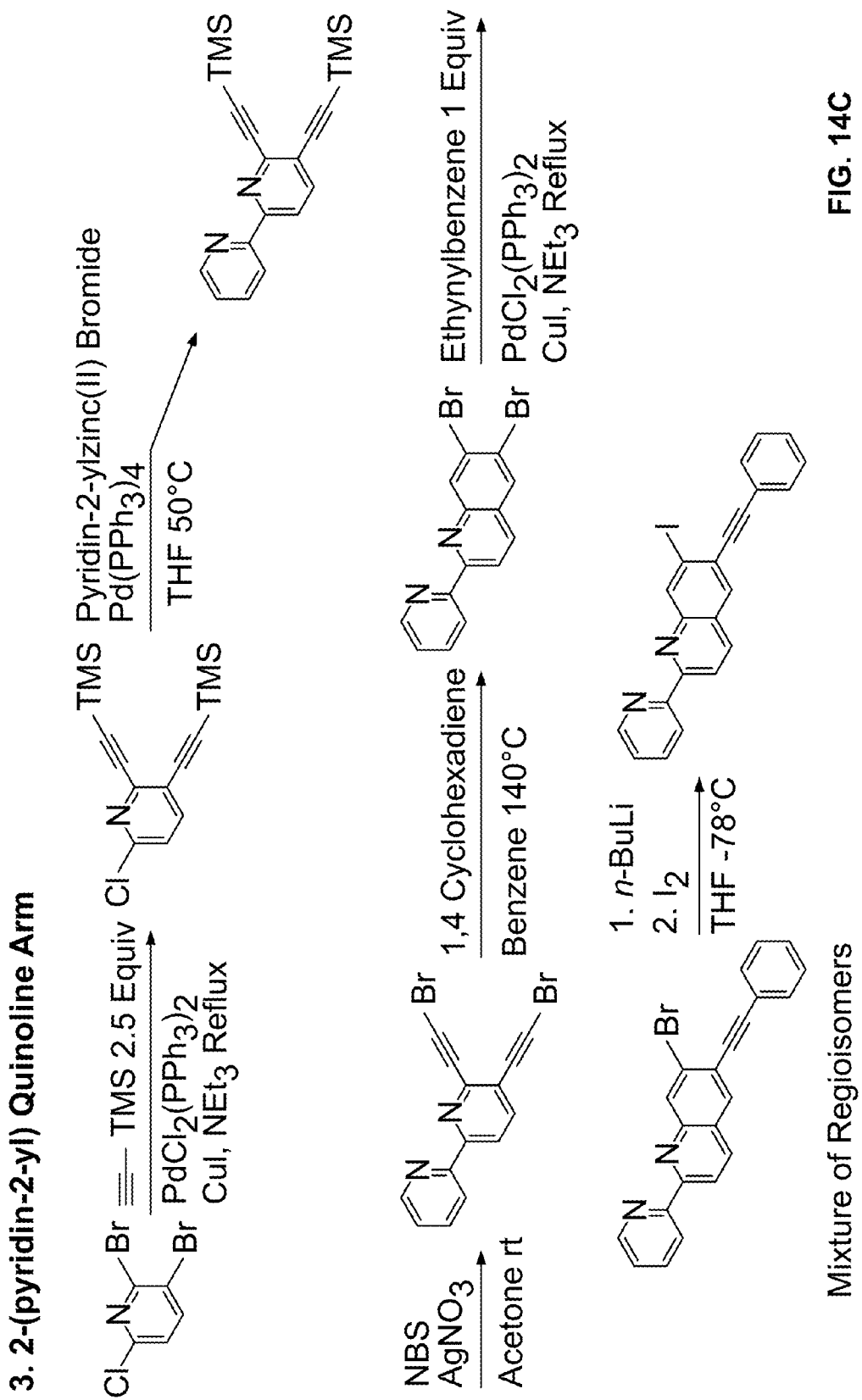
Figure 14D:
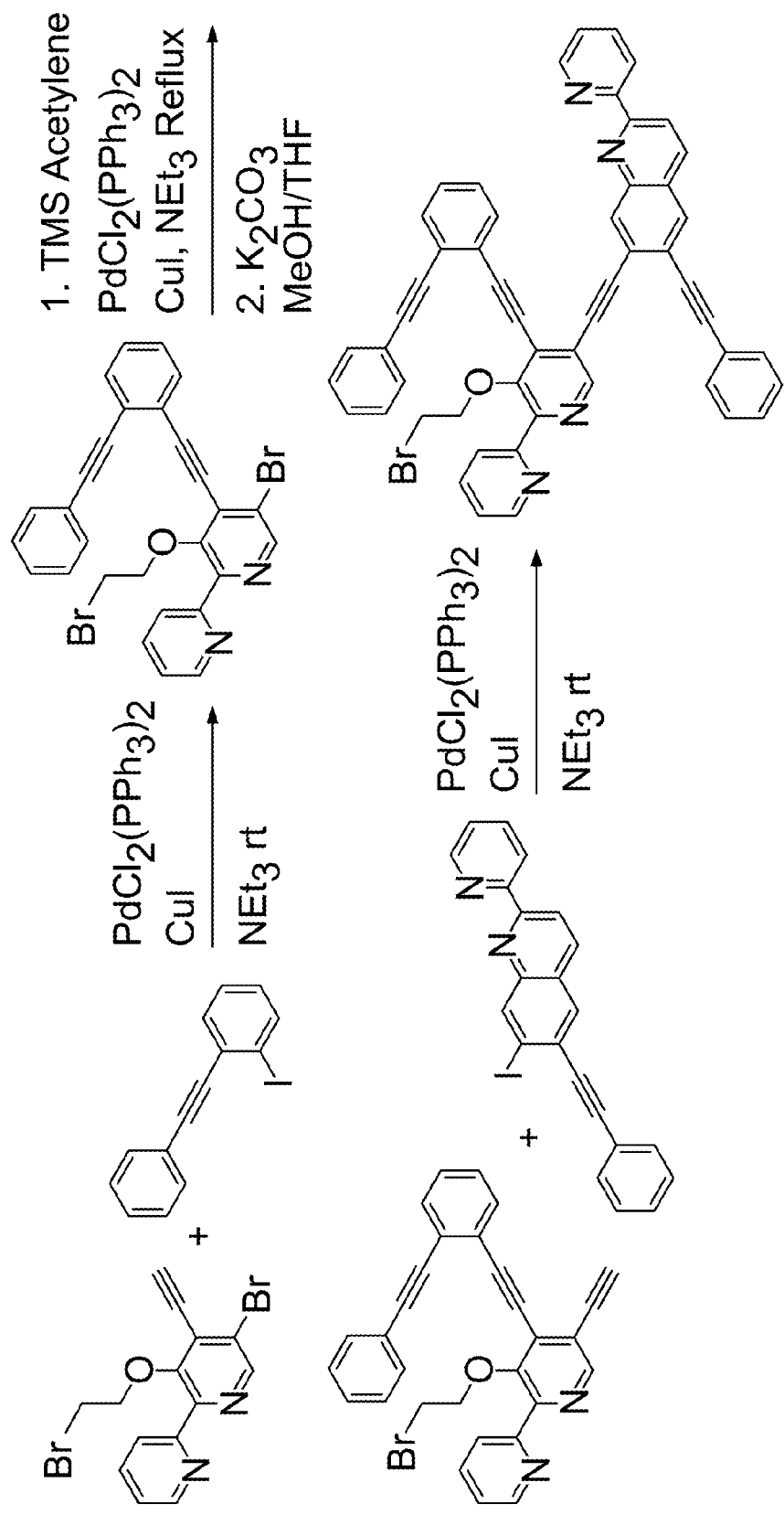
Figure 15A:
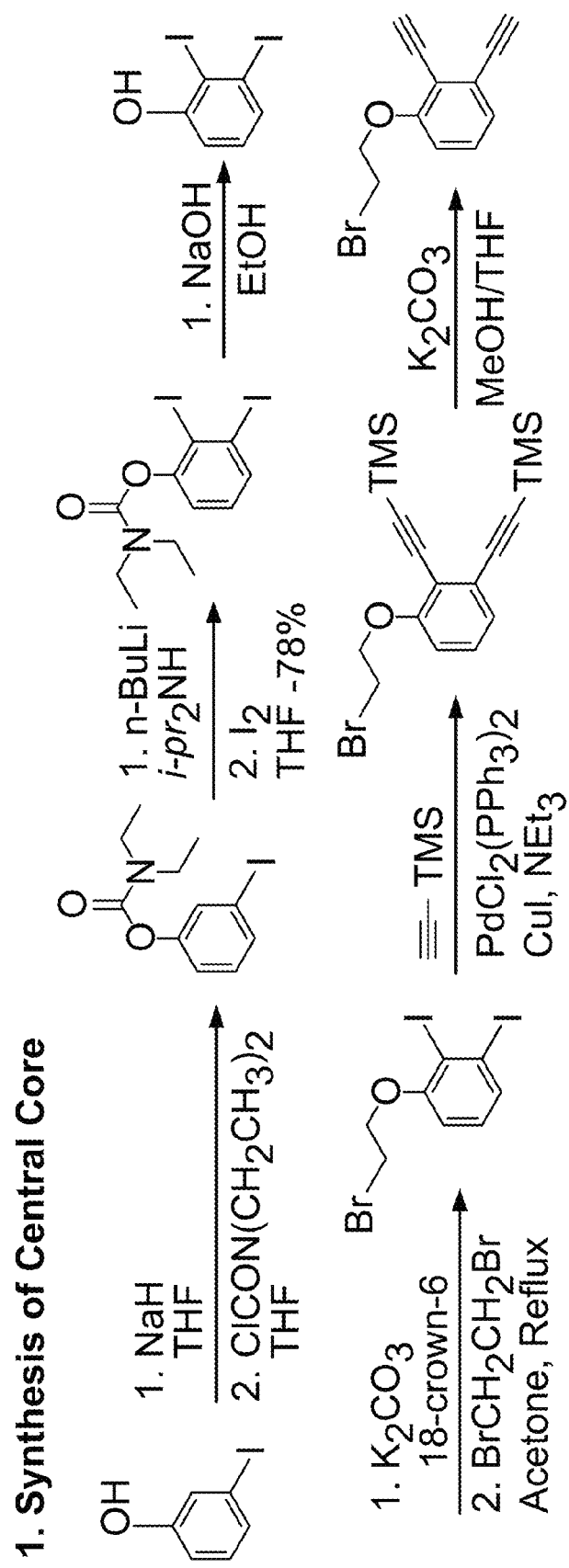
FIGS. 15A through 15C depict the synthetic scheme for the preparation of oligo-alkyne of compound B of FIG. 13.
Figure 15B:
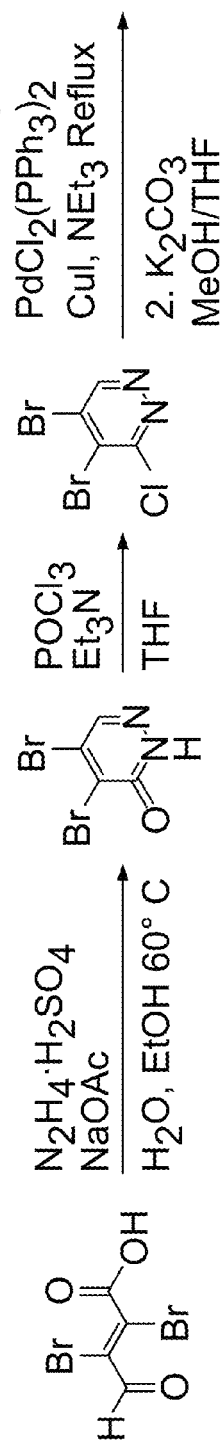
Figure 15B:
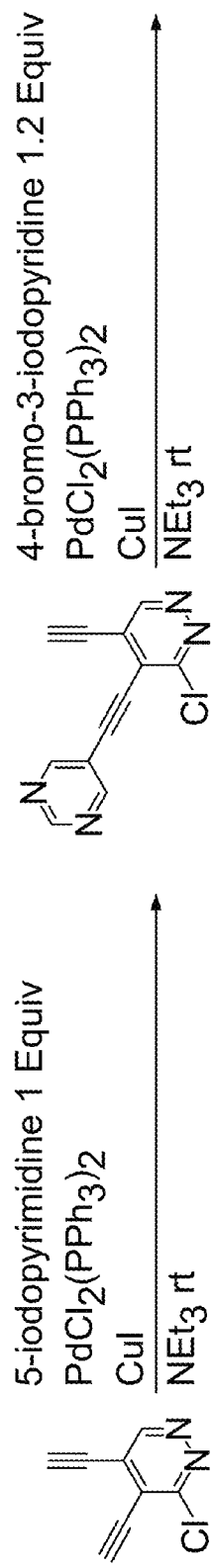
Figure 15B:
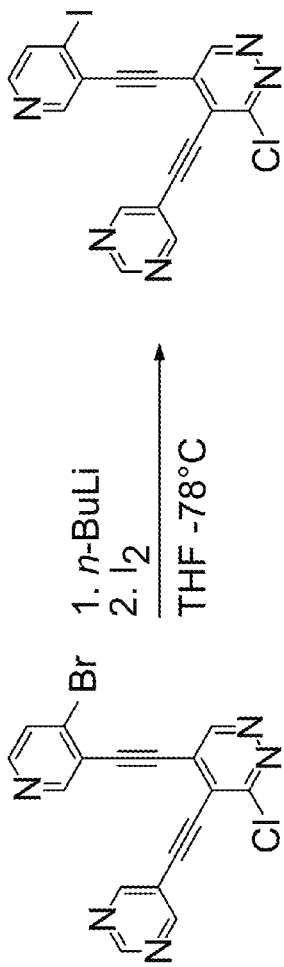
Figure 15C:
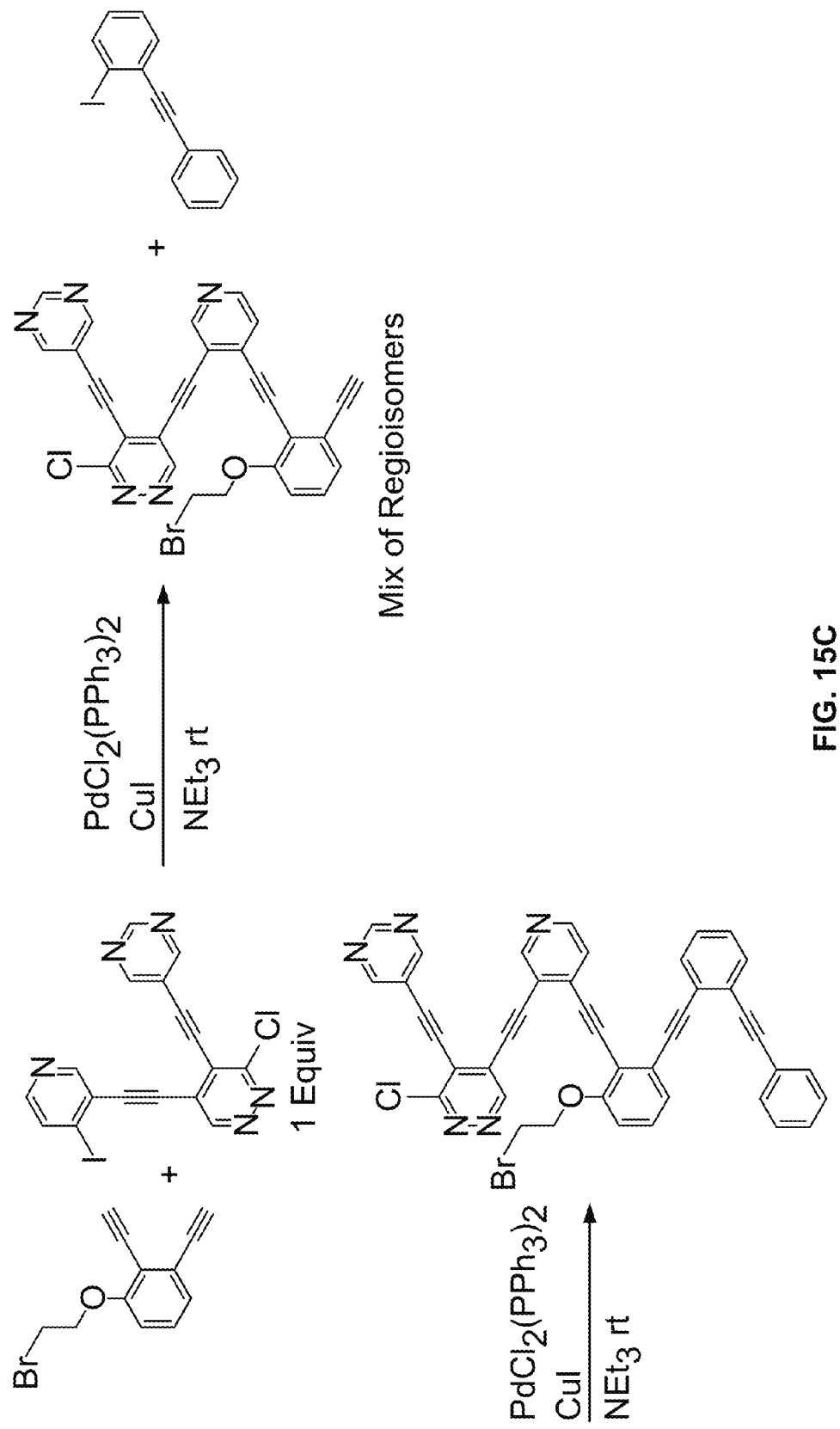
Figure 16A:
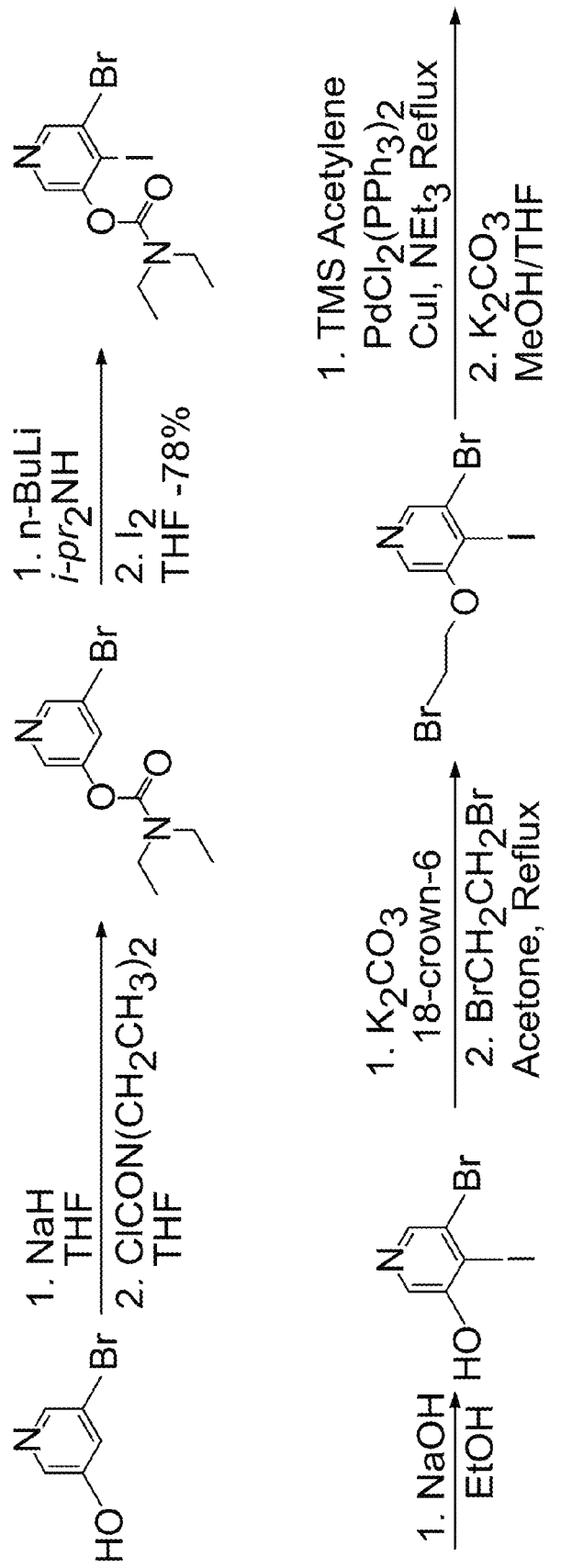
FIGS. 16A through 16C depict the synthetic scheme for the preparation of oligo-alkyne of compound C of FIG. 13.
Figure 16B:
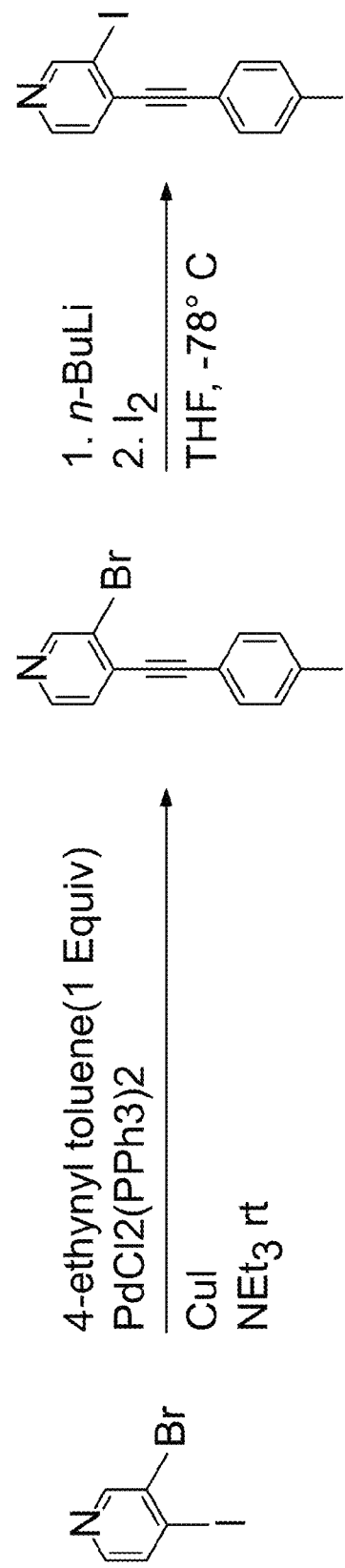
Figure 16C:
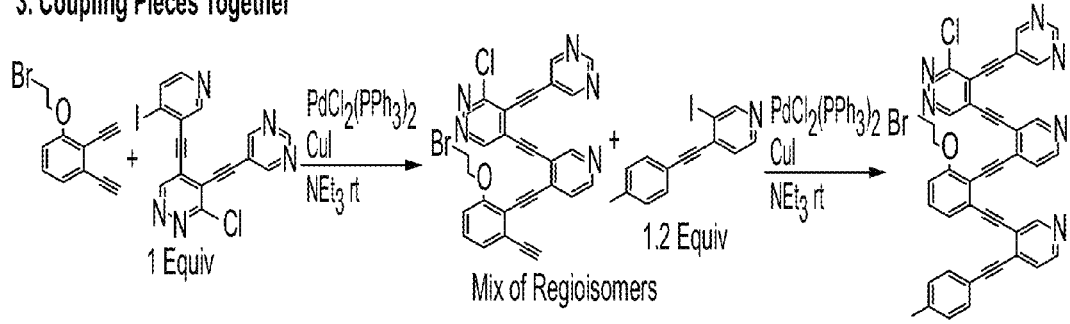
Figure 16C:
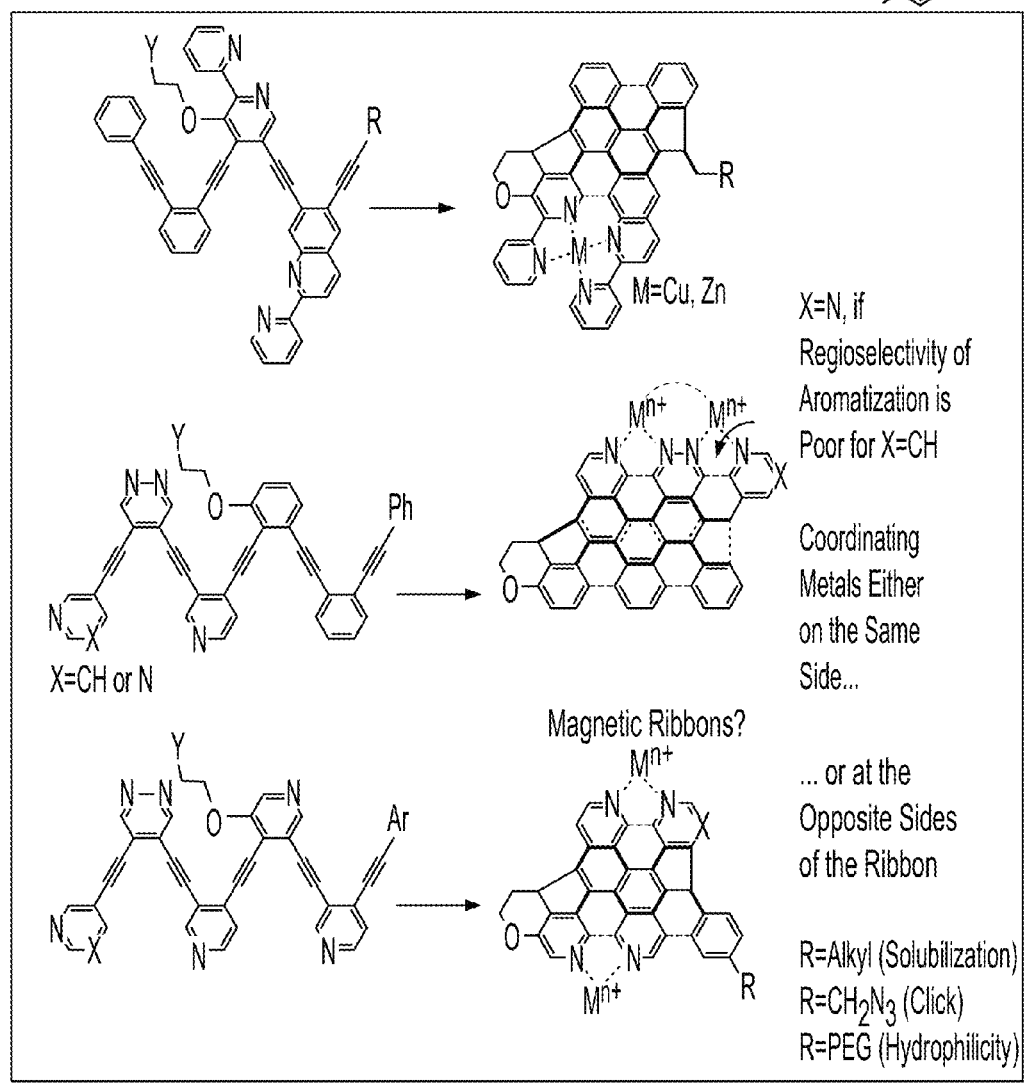

Because nitrogen-containing heterocycles are compatible with these cascades, we can prepare a variety of new polycyclic ligands for different metals with multiple potential applications in molecular electronics. The examples shown in FIG. 13 illustrate the flexibility of this molecular design and the variety of molecular architectures available via structural modifications in the initial oligo-alkyne. For example, the top example imposes a planar square geometry on the metal binding site whereas the bottom designs offer more flexibility and can be used to fine tune exchange coupling of various 3d transition metal ions, in particular the classic $Fe^{2+/3+}$ and $R^{2+/3+}$ mixed-valence systems. The synthetic schemes for preparing each of Compound A, B, and C are provided in FIGS. 14, 15, and 16, respectively.

In any of the oligo-alkyne structures according to the present invention, modular assembly allows the linkage of any two or more aromatic-alkyne groups having different structures from each other. The present invention advantageously utilizes cascade transformations to prepare graphene nanoribbons and graphene substructures of nearly any design. Current organic synthesis has a lot to offer this new field of graphene chemistry by providing access to differentially-substituted graphene pieces that could have a number of electronic applications. The accomplishment of the design and synthesis of nano-sized electronics could revolutionize current nano-electronics as there is always the constant push in the computer industry to make electronics smaller and more efficient.

The following non-limiting examples are provided to further illustrate the present invention.

EXAMPLES

Example 1

Synthesis of Model Enediynes

The following reaction sequence illustrates the general technique for synthesizing the model compound and for the addition of aromatic-alkyne building blocks to the model compound.

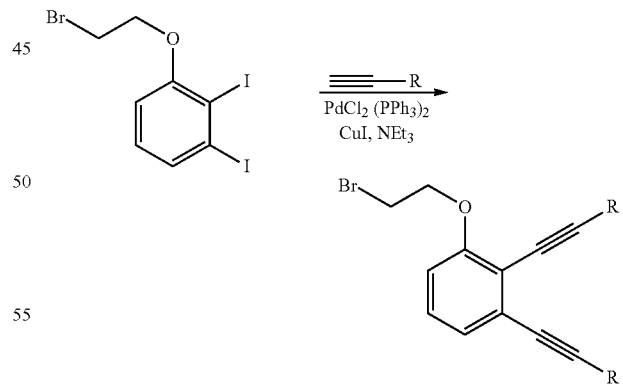

1, R =
a) Ph (72%)
b) p-MePh (83%)
c) p-FPh (87%)
d) p-OMePh (74%)
e) TMS (83%)

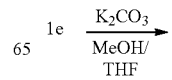

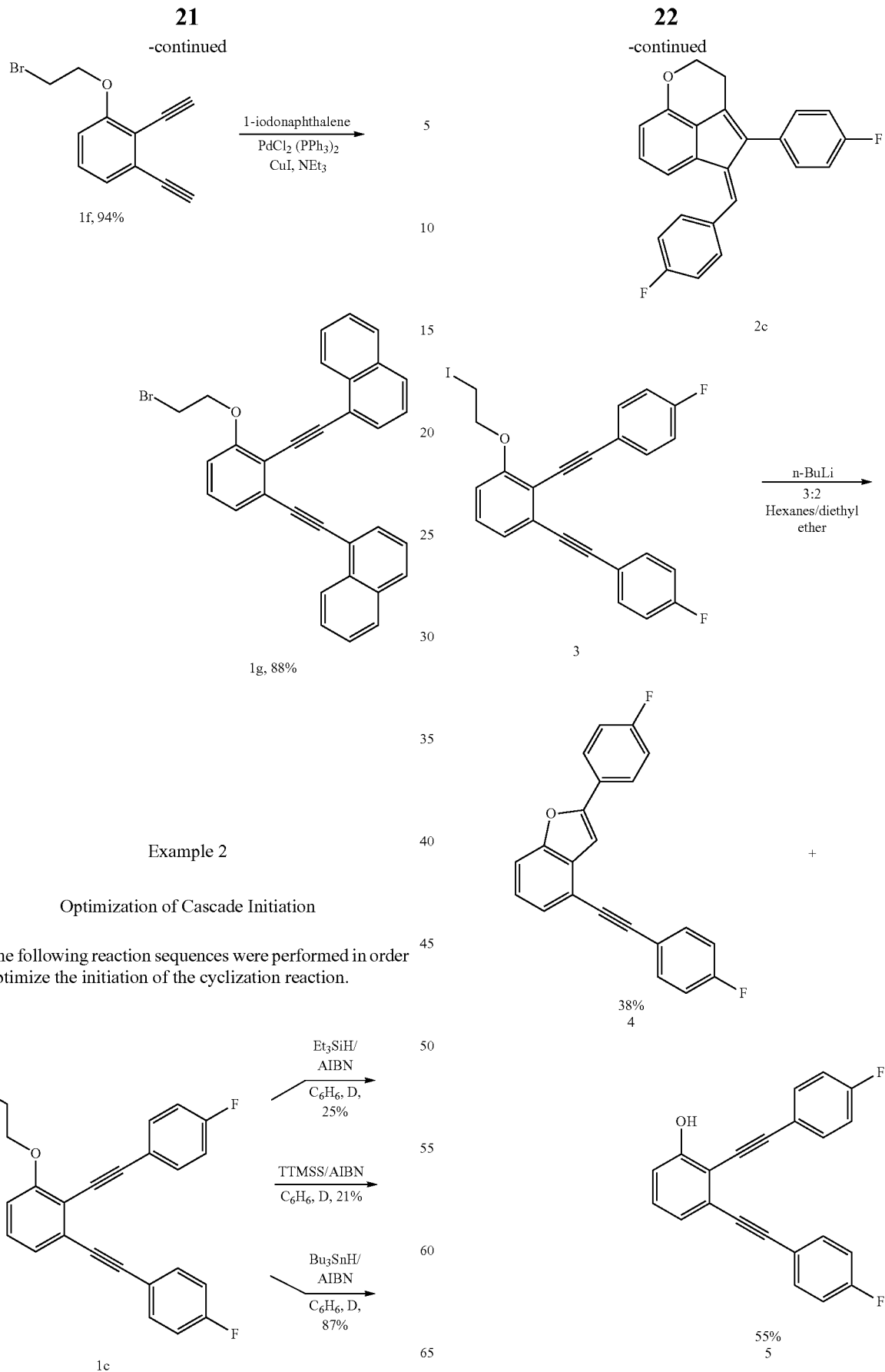
Example 2
Optimization of Cascade Initiation
The following reaction sequences were performed in order to optimize the initiation of the cyclization reaction.

Example 3

Mechanism of Cascade Initiation

The following reaction sequence demonstrates the mechanism of cascade initiation of the cyclization reaction.

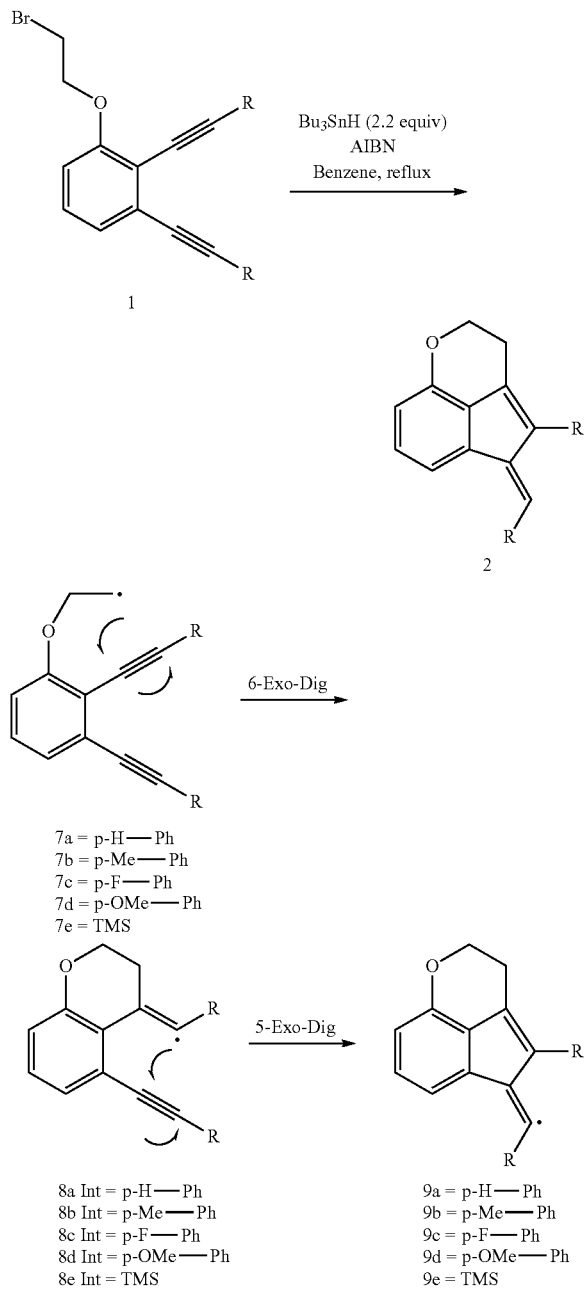

Example 4

General Procedure for Synthesis Compounds According to the Present Invention THF and hexanes used for reactions were dried over sodium and distilled. Hexanes used for column chromatography were distilled prior to use. All other solvents were used as purchased. Column Chromatography was performed using silica gel (60 Å). Unless otherwise noted, all $^1$H NMRs were run on 400 MHz and 600 MHz spectrometer in CDCl$_3$ and CD$_3$CN and all $^{13}$C NMR were run on 100 MHz and 150 MHz spectrometer in CDCl$_3$ and CD$_3$CN. Proton chemical shifts are given relative to the residual proton signals of the deuterated solvent CDCl$_3$ (7.26 ppm), CD$_3$CN (1.94 ppm). Carbon chemical shifts were internally referenced to the deuterated solvent signals in CDCl$_3$ (77.00 ppm), CD$_3$CN (1.4, 118.7). All J-coupling values are reported in Hertz (Hz).

Example 5

General Procedure for Protection of 2,3 Iodophenol with "Weak Link" Group (a)

A suspension of 2,3 iodophenol (0.77 mmol), K$_2$CO$_3$ (1.69 mmol) and 18-crown-6 (0.04 mmol) in 18 mL of acetone was brought to reflux. Through top of condenser 1,2 dibromoethane (3.06 mmol) was added drop wise. Reaction was monitored by TLC. At completion of reaction, usual aqueous workup was performed. The reaction mixture was purified by flash chromatography on silica gel, (eluent: hexane/EtOAc) on silica gel to afford compound a.

Example 6

Procedure for Synthesis of 3-Iodophenyl Diethylcarbamate (b)

To a stirred suspension of NaH (1.09 g, 45.47 mmol), in THF (23 mL), a solution of 3-iodophenol (5.00 g, 22.73 mmol), in THF (5.70 mL) was drop wise added at room temperature. After stirring the reaction mixture for 2 h. N,N-diethylcarbamoyl chloride (6.17 g, 45.47 mmol) in THF (8 mL) was added. Stirring was continued for another 8 h. Usual aqueous work up gave the crude carbamate which was purified by column chromatography (eluent: hexane/EtOAc) on silica gel to afford compound b.

Example 7

Procedure for Synthesis of 2,3-Diiodophenyl Diethylcarbamate (c)

n-BuLi (14.95 mL of a 1.6M sol. in hexane, 23.91 mmol) was added to solution of i-Pr2NH (3.38 mL, 23.91 mmol) in THF (50 mL) at 0° C. After 30 min at 0° C. the LDA solution was cooled to −78° C. and the c (21.74 mmol) was added. The resulting solution was stirred for 30 min at −78° C. and then iodine (6.62 g, 26.09 mmol) in THF (15 mL) was added. After 30 min at low temperature the reaction mixture was allowed to warm to room temperature, H$_2$O was added and THF evaporated under reduced pressure. The aqueous phase was extracted with EtOAc (3×25 mL) and the combined organic layers were washed with 1M HCl, dried over anhydrous Na$_2$SO$_4$, and evaporated under reduced pressure. The crude mixture was purified by column chromatography (eluent: hexane/EtOAc) on silica gel to afford compound c.

Example 8

Procedure for Synthesis of 2,3-Diiodophenol (d)

To a solution of the carbamate 3 (10.07 mmol) in EtOH (130 mL) a large excess of NaOH (4.03 g, 0.10 mol) was added. The mixture was refluxed for 5-8 h. After cooling to room temperature most of the EtOH was evaporated under reduced pressure, the residue was diluted with diethyl ether and the excess of NaOH was neutralized at 0° C. using a 1M solution of HCL. The aqueous solution was extracted with diethyl ether (3×20 mL) and the combined organic phase was washed with brine, dried with $Na_2SO_4$, and evaporated under reduced pressure. The crude was purified by column chromatography (eluent: hexane/EtOAc) on silica gel to afford compound d.

Example 9

General Procedure for Sonogashira Cross Coupling of 6 with Different Substituted Acetylenes (1)

A suspension of aryl dihalide (0.59 mmol), $PdCl_2 (PPh_3)_2$ (29.70 μmol), Cu(I) iodide (29.70 μmol) in 15 mL of triethylamine was degassed three times with freeze/pump/thaw technique in a flame dried round bottom flask. 2.5 equiv. of 4-ethynyl-anisole (1.49 mmol) was added using a syringe once solution thawed and allowed to react for 8 hours. The reaction was monitored by TLC. After total consumption of the aryl halide, the reaction mixture was filtered through celite and washed with methylene chloride (3×30 mL). The organic layer was washed with a saturated solution of ammonium chloride (2×30 mL), water (2×30 mL) and dried over anhydrous $Na_2SO_4$. Solvent was removed in vacuo. The reaction mixture was purified by flash chromatography on silica gel, (eluent: hexane/EtOAc) on silica gel to afford compound 1.

Example 10

General Procedure for Radical Cascade of (2)

To three separate round-bottom flasks were added 40.00 mg of bis-methylbenzene (1) in 6 mL of benzene, 59.70 mg $Bu_3SnH$ in 2 mL of benzene, and 1.53 mg AIBN in 2 mL benzene. Nitrogen was bubbled in flasks for 20 min to degas solution. $Bu_3SnH$ and AIBN were added by syringe pump through the top of a condenser over the course of 6 hours to a refluxing solution of bis-methylbenzene. The reaction was monitored by TLC. After conversion of all starting material, the reaction mixture was concentrated and purified by preparatory TLC, (eluent: hexane/EtOAc) on silica gel to afford compound 2.

Example 11

General Procedure for Finkelstein reaction of (3) and (13)

Sodium iodide was added in one portion in to a stirred solution of (1c)(55 mg, 0.13 mmol) in 10 mL of acetone. The mixture was heated to 50° C. under nitrogen atmosphere for 8 h. Upon completion then solvent was removed under vacuum. The resulting solid was dissolved in $CH_2Cl_2$ and washed with saturated $Na_2S_2O_3$, water, brine and dried over anhydrous $Na_2SO_4$. Solvent was removed in vacuo giving compound (3) in quantitative yield as a light yellow oil.

Example 12

Procedure for Anionic Cascade Reaction (4) and (5)

A 0.1 M solution of (3) (61 mg, 0.17 mmol) in 15 mL 3:2 hexane/$Et_2O$ was deoxygenated by bubbling $N_2$ for 5 minutes. The mixture was cooled to −78° C. A solution of n-BuLi (0.16 mL of a 1.6 M sol. in hexane, 0.25 mmol) was added drop wise. The solution was stirred for 10 more minutes at −78° C. and then the cooling bath was removed. The reaction mixture was stirred 2.5 h at room temp in order for the cyclization to occur. The cyclized solution was cooled back down to −78° C. and an excess of MeOH (30.5 μL, 0.77 mmol) was added. After the addition the cooling bath was removed and the reaction was stirred for 3 h. To the reaction mixture was added deionized water. The mixture was extracted with $CH_2Cl_2$ and washed with ammonium chloride and brine solution 2 times and dried over $Na_2SO_4$. Solvent was removed in vacuo and purified by flash chromatography on silica gel, (eluent: hexane/EtOAc) on silica gel to afford compounds (4) and (5).

Example 13

Procedure for Deprotection of TMS Protecting Groups (2f)

To a solution of ((3-(2-bromoethoxy)-1,2-phenylene)bis(ethyne-2,1-diyl))bis(trimethylsilane) 6e (225 mg, 0.57 mmol), in 1:1 mixture of MeOH/THF (18 mL) was added $K_2CO_3$ (30 mg, 0.21 mmol). The solution was stirred at room temperature for 8 h under nitrogen. Water was added to quench the reaction and usual aqueous work up was performed. The reaction mixture was purified by flash chromatography on silica gel, (eluent: hexane/EtOAc) on silica gel to afford compound 2f.

Example 14

1-(2-bromoethoxy)-2,3-diiodobenzene (a)

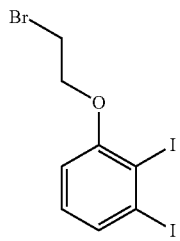 [SMILES: BrCCOc1cccc(I)c1I]

Chromatographic purification (10% ethyl acetate in hexanes) afforded compound a (77%) as a white solid. $R_f$=0.6 (20% ethyl acetate in hexanes); $^1H$ NMR (400 MHz, $CDCl_3$): δ 7.52 (dd, J=1.1, 7.9 Hz, 1H), 7.02 (t, J=8.0 Hz, 1H), 6.70 (dd, J=3.0, 0.8 Hz, 1H), 4.28 (t, J=6.3 Hz, 2H), 3.67 (t, J=6.3 Hz, 2H); $^{13}C$ NMR (150 MHz, $CDCl_3$): δ 158.1, 132.6, 130.5, 111.2, 110.0, 101.5, 69.7, 28.3; HRMS (EI): calcd for $C_8H_7OBrI_2$ [M]+ 451.7770, found 451.7760.

Example 15

((3-(2-bromoethoxy)-1,2-phenylene)bis(ethyne-2,1-diyl))dibenzene (1a)

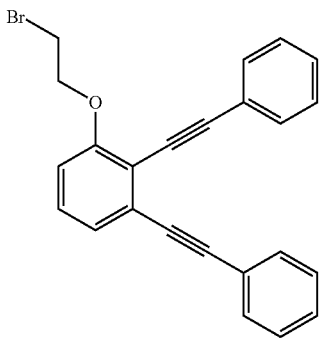 [SMILES: BrCCOc1cccc(C#Cc2ccccc2)c1C#Cc1ccccc1]

Chromatographic purification (10% ethyl acetate in hexanes) afforded compound 1a (72%) as a light yellow oil. $R_f$=0.5 (10% ethyl acetate in hexanes); $^1$H NMR (600 MHz, CDCl$_3$): δ 7.64 (d, J=6.5 Hz, 2H), 7.61 (dd, J=5.7, 2.3 Hz, 2H), 7.37 (m, 6H), 7.24 (s, 1H), 7.23 (d, J=2.0 Hz, 1H), 6.86 (t, J=4.6 Hz, 1H), 4.38 (t, J=6.2, 2H), 3.71 (t, J=6.3, 2H); $^{13}$C NMR (150 MHz, CDCl$_3$): δ 158.6, 131.6, 131.6, 131.5, 128.8, 128.4, 128.3, 128.3, 127.4, 125.0, 123.6, 123.1, 116.2, 112.9, 98.3, 93.8, 88.1, 84.4, 69.0, 28.9; HRMS (EI): calcd for C$_{24}$H$_{17}$OBr [M]+ 400.04628, found 400.04552.

Example 16

4,4'-((3-(2-bromoethoxy)-1,2-phenylene)bis(ethyne-2,1-diyl))bis(methylbenzene) (1b)

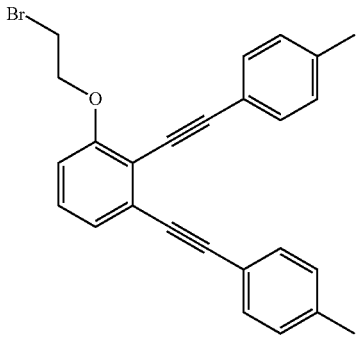 [SMILES: Cc1ccc(C#Cc2cccc(OCCBr)c2C#Cc2ccc(C)cc2)cc1]

Chromatographic purification (10% ethyl acetate in hexanes) afforded compound 1b (83%) as a light yellow oil. $R_f$=0.5 (10% ethyl acetate in hexanes); $^1$H NMR (600 MHz, CDCl$_3$): δ 7.49 (dd, J=12.8, 8.0 Hz, 4H), 7.22 (d, J=3.8 Hz, 1H), 7.21 (s, 1H), 7.16 (dt, J=7.93, 0.7 Hz, 4H), 6.86 (dd, J=6.5, 2.8 Hz, 1H), 4.39 (t, J=6.4 Hz, 2H), 3.72 (t, J=6.4 Hz, 2H), 2.38 (s, 6H); $^{13}$C NMR (150 MHz, CDCl$_3$): δ 158.6, 138.6, 138.4, 131.6, 131.5, 129.1, 129.1, 128.6, 127.6, 125.1, 120.6, 120.2, 116.5, 113.0, 98.5, 94.0, 87.6, 83.8, 69.1, 28.8, 21.5; HRMS (EI): calcd for C$_{26}$H$_{21}$OBr [M]+ 428.07758, found 428.07769.

Example 17

4,4'-((3-(2-bromoethoxy)-1,2-phenylene)bis(ethyne-2,1-diyl))bis(fluorobenzene) (1c)

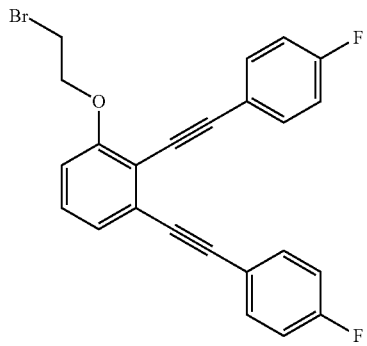 [SMILES: Fc1ccc(C#Cc2cccc(OCCBr)c2C#Cc2ccc(F)cc2)cc1]

Chromatographic purification (15% ethyl acetate in hexanes) afforded compound 1c (87%) as a light red oil. $R_f$=0.4 (10% ethyl acetate in hexanes); $^1$H NMR (600 MHz, CDCl$_3$): δ 7.55 (m, 4H), 7.24 (t, J=8.0 Hz, 1H), 7.20 (dd, J=7.7, 1.1 Hz, 1H), 7.05 (td, J=8.7, 1.6 Hz, 4H), 6.87 (dd, J=8.1, 1.1 Hz, 1H), 4.39 (t, J=6.3 Hz, 2H), 3.72 (t, J=6.3 Hz, 2H); $^{13}$C NMR (150 MHz, CDCl$_3$): δ 163.4 (d, J=13.1 Hz), 161.8 (d, J=13.1 Hz), 158.6, 133.54, 133.48, 133.47, 133.41, 128.9, 127.2, 125.0, 119.7 (d, J=3.5 Hz), 119.3 (d, J=3.3 Hz), 116.0, 112.9, 97.1, 92.7, 87.7, 84.1, 68.9, 28.8; HRMS (EI): calcd for C$_{24}$H$_{15}$OBrF$_2$ [M]+ 436.02744, found 436.02660.

Example 18

4,4'-((3-(2-bromoethoxy)-1,2-phenylene)bis(ethyne-2,1-diyl))bis(methoxybenzene) (1d)

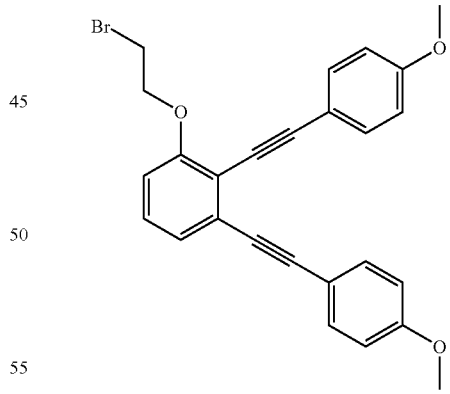

Chromatographic purification (10% ethyl acetate in hexanes) afforded compound 1d (74%) as a red oil. $R_f$=0.5 (10% ethyl acetate in hexanes); $^1$H NMR (600 MHz, CDCl$_3$): δ 7.53 (dd, J=14.3, 8.9 Hz, 4H), 7.20 (d, J=2.9 Hz, 1H), 7.19 (s, 1H), 6.88 (d, J=8.5 Hz, 4H), 6.84 (dd, J=6.1, 3.2 Hz, 1H), 4.38 (t, J=6.4 Hz, 2H), 3.83 (s, 6H), 3.71 (t, J=6.4 Hz, 2H); $^{13}$C NMR (150 MHz, CDCl$_3$): δ 159.8, 159.7, 158.4, 133.13, 133.06, 128.4, 127.5, 125.0, 116.5, 115.8, 115.4, 114.0, 113.98, 112.8, 98.3, 93.8, 87.0, 83.2, 69.1, 55.3, 28.9; HRMS (EI): calcd for C$_{26}$H$_{21}$O$_3$Br [M]+ 460.06741, found 460.06803.

Example 19

((3-(2-bromoethoxy)-1,2-phenylene)bis(ethyne-2,1-diyl))bis(trimethylsilane) (1e)

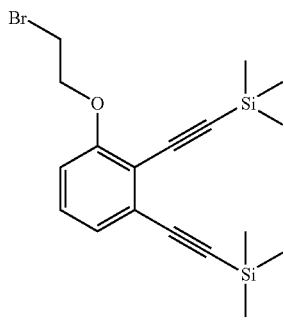 [SMILES: C[Si](C)(C)C#Cc1cccc(OCCBr)c1C#C[Si](C)(C)C]

Chromatographic purification (10% ethyl acetate in hexanes) afforded compound 1e (83%) as a tan oil. $R_f$=0.5 (15% ethyl acetate in hexanes); $^1$H NMR (600 MHz, CDCl$_3$): δ 7.16 (t, J=8.0 Hz, 1H), 7.11 (dd, J=7.7, 1.0 Hz, 1H), 6.8 (dd, J=8.2, 0.9 Hz, 1H), 4.31 (t, J=6.5 Hz, 2H), 3.64 (t, J=6.4 Hz, 2H), 0.28 (s, 9H), 0.27 (s, 9H); $^{13}$C NMR (150 MHz, CDCl$_3$): δ 159.2, 128.9, 127.5, 125.7, 116.5, 113.7, 103.8, 102.9, 98.8, 69.2, 28.6, 0.05, 0.02; HRMS (EI): calcd for C$_{18}$H$_{25}$OBrSi$_2$ [M]+ 392.06274, found 392.06123.

Example 20

1-(2-bromoethoxy)-2,3-diethynylbenzene (1f)

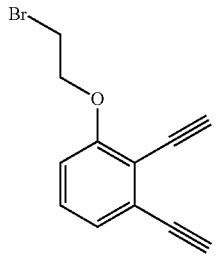

Chromatographic purification (5% ethyl acetate in hexanes) afforded compound 1f (94%) as a brown solid. $R_f$=0.6 (10% ethyl acetate in hexanes); $^1$H NMR (600 MHz, CDCl$_3$): δ 7.23 (t, J=8.0 Hz, 1H), 7.15 (d, J=7.7 Hz, 1H), 6.87 (d, J=8.3 Hz, 1H), 4.33 (t, J=6.6 Hz, 2H), 3.56 (s, 1H), 3.34 (s, 1H); $^{13}$C NMR (150 MHz, CDCl$_3$): δ 159.4, 129.5, 127.1, 125.9, 115.5, 113.5, 86.0, 81.7, 81.6, 77.8, 69.1, 28.5; HRMS (EI): calcd for C$_{12}$H$_9$OBr [M]+ 247.9837, found 247.9838.

Example 21

1,1'-((3-(2-bromoethoxy)-1,2-phenylene)bis(ethyne-2,1-diyl))dinaphthalene (1g)

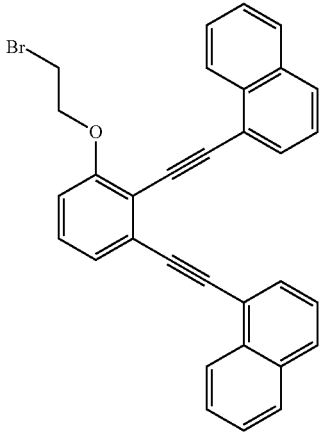 [SMILES: BrCCOc1cccc(C#Cc2cccc3ccccc23)c1C#Cc1cccc2ccccc12]

Chromatographic purification (10% ethyl acetate in hexanes) afforded compound 1g (88%) as a light brown oil. $R_f$=0.4 (15% ethyl acetate in hexanes); $^1$H NMR (600 MHz, CDCl$_3$): δ 8.68 (dd, J=8.4, 0.7 Hz, 1H), 8.59 (dd, J=8.4, 0.7 Hz, 1H), 7.86 (m, 5H), 7.79 (dd, J=7.1, 1.1 Hz, 1H), 7.47 (m, 2H), 7.44 (m, 1H), 7.40 (m, 2H), 7.33 (t, J=16.0 Hz, 1H), 7.23 (m, 2H), 6.94 (d, J=8.2 Hz, 1H), 4.47 (t, J=6.2 Hz, 2H), 3.80 (t, J=6.3 Hz, 2H); $^{13}$C NMR (150 MHz, CDCl$_3$): δ 158.9, 133.4, 133.3, 133.14, 133.11, 130.9, 130.8, 128.9, 128.8, 128.1, 128.0, 127.4, 127.0, 126.8, 126.7, 126.6, 126.4, 126.3, 125.4, 125.18, 125.17, 121.2, 120.8, 116.1, 112.4, 96.6, 93.0, 92.0, 89.4, 69.0, 28.8; HRMS (EI): calcd for C$_{32}$H$_{21}$OBr [M]+ 500.07758, found 500.07750.

Example 22

4,4'-((3-(2-iodoethoxy)-1,2-phenylene)bis(ethyne-2,1-diyl))bis(fluorobenzene) (3)

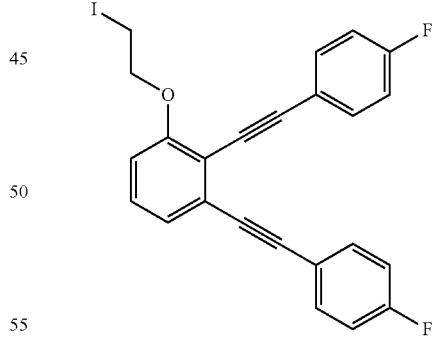

Washes with Na$_2$S$_2$O$_3$, water, brine afforded the compound 3 (>99%) as a light yellow oil. $R_f$=0.5; $^1$H NMR (600 MHz, CDCl$_3$): δ 7.57 (m, 2H), 7.53 (m, 2H), 7.23 (t, J=8.0 Hz, 1H), 7.19 (dd, J=2.9, 1.1 Hz, 1H), 7.05 (t, J=8.6 Hz, 4H), 6.85 (dd, J=3.0, 0.9 Hz, 1H), 4.34 (t, J=13.6 Hz, 2H), 3.50 (t, J=13.6 Hz, 2H); $^{13}$C NMR (150 MHz, CDCl$_3$): δ 163.4 (d, J=13.2 Hz), 161.8 (d, J=13.2 Hz), 158.4, 133.5 (d, J=6.8 Hz), 133.4 (d, J=6.7 Hz), 128.9, 127.2, 124.9, 119.7 (d, J=3.2 Hz), 119.2 (d, J=3.3 Hz), 115.9, 115.7 (d, J=22.2 Hz), 115.6 (d, J=22.0 Hz), 112.7, 97.1, 92.7, 87.7, 84.1, 69.6, 0.8; HRMS (EI): calcd for C$_{24}$H$_{15}$F$_2$OI [M]+ 484.0136, found 484.0133.

Example 23

2,2'-((3-(2-bromoethoxy)-1,2-phenylene)bis(ethyne-2,1-diyl))bis((p-tolylethynyl)benzene) (11a)

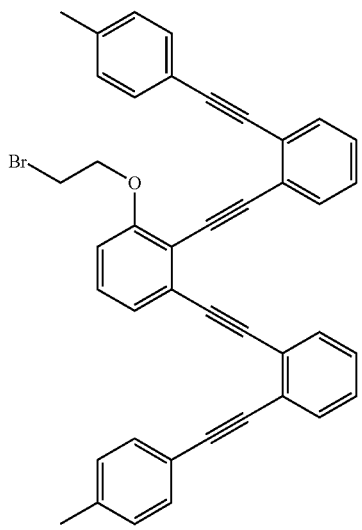 [SMILES: Cc1ccc(C#Cc2ccccc2C#Cc2cccc(OCCBr)c2C#Cc2ccccc2C#Cc2ccc(C)cc2)cc1]

Chromatographic purification (20% ethyl acetate in hexanes) afforded compound 11a (84%) as an oil. $R_f$=0.2 (15% ethyl acetate in hexanes); $^1$H NMR (600 MHz, CD$_3$CN): δ 7.56 (d, J=0.8 Hz, 1H), 7.54 (d, J=1.4 Hz, 1H), 7.46 (m, 2H), 7.36 (dd, J=8.0, 4.7 Hz, 2H), 7.33 (td, J=15.3, 9.5 Hz, 2H), 7.30 (m, 1H), 7.29 (m, 2H), 7.28 (m, 1H), 7.25 (m, 1H), 7.21 (td, J=15.3, 7.6 Hz, 1H), 7.12 (d, J=7.9 Hz, 2H), 7.05 (d, J=7.9 Hz, 2H), 7.02 (dd, J=8.4, 0.9 Hz, 1H), 4.32 (t, J=5.9 Hz, 2H), 3.53 (t, J=5.9 Hz, 2H), 2.29 (s, 3H), 2.25 (s, 3H); $^{13}$C NMR (150 MHz, CD$_3$CN): δ 160.2, 140.2, 140.0, 133.4, 133.2, 132.8, 132.6, 132.5, 132.4, 130.9, 130.3, 130.2, 129.7, 129.6, 129.2, 129.16, 128.0, 126.6, 126.57, 126.3, 126.1, 126.05, 120.8, 120.76, 116.2, 114.7, 97.8, 94.8, 94.7, 93.5, 92.8, 89.3, 88.5, 88.4, 70.2, 30.6, 21.64, 21.6; HRMS (EI): calcd for C$_{42}$H$_{29}$BrO [M]+ 628.14018, found 628.14014.

Example 24

2,2'-((3-(2-iodoethoxy)-1,2-phenylene)bis(ethyne-2,1-diyl))bis((p-tolylethynyl)benzene) (12a)

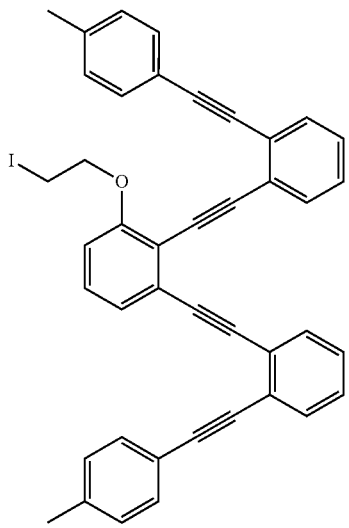 [SMILES: Cc1ccc(C#Cc2ccccc2C#Cc2cccc(OCCI)c2C#Cc2ccccc2C#Cc2ccc(C)cc2)cc1]

Chromatographic purification (15% ethyl acetate in hexanes) afforded compound 12a (99%) as a oil. $R_f$=0.3 (15% ethyl acetate in hexanes); $^1$H NMR (600 MHz, CDCl$_3$): δ 7.63 (d, J=7.5 Hz, 1H), 7.55 (d, J=7.6 Hz, 1H), 7.52 (d, J=7.6 Hz, 1H), 7.50 (d, J=7.7 Hz, 1H), 7.43 (d, J=7.9 Hz, 2H), 7.40 (d, J=7.9 Hz, 2H), 7.28 (t, J=7.3 Hz, 2H), 7.24 (m, 3H), 7.19 (t, J=7.5 Hz, 1H), 7.12 (d, J=7.9 Hz, 2H), 7.08 (d, J=7.9 Hz, 2H), 6.89 (d, J=8.2 Hz, 1H), 4.22 (t, J=7.5 Hz, 2H), 3.18 (t, J=7.5 Hz, 2H), 2.35 (s, 3H), 2.33 (s, 3H); $^{13}$C NMR (150 MHz, CDCl$_3$): δ 158.7, 138.4, 132.5, 132.3, 131.7, 131.6, 131.5, 129.0, 128.95, 128.9, 128.0, 127.9, 127.6, 126.1, 126.0, 125.6, 125.59, 125.5, 120.2, 116.3, 113.5, 97.2, 93.9, 93.7, 92.9, 92.0, 88.2, 87.8, 87.7, 70.2, 21.5, 21.49, 0.6; HRMS (EI): calcd for C$_{42}$H$_{29}$IO [M]+ 676.12631, found 676.12625.

Example 25

2,2'-((3-(2-bromoethoxy)-1,2-phenylene)bis(ethyne-2,1-diyl))bis((phenylethynyl)benzene) (11b)

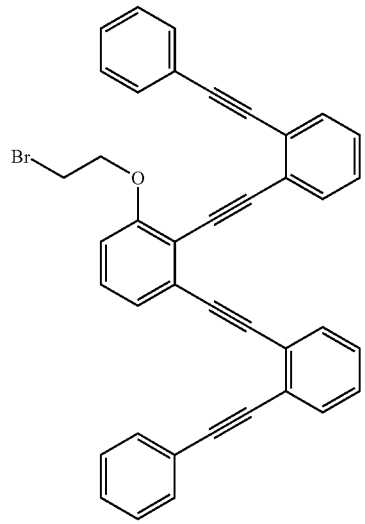 [SMILES: BrCCOc1cccc(C#Cc2ccccc2C#Cc2ccccc2)c1C#Cc1ccccc1C#Cc1ccccc1]

Chromatographic purification (20% ethyl acetate in hexanes) afforded compound 11b (84%) as a orange oil. $R_f$=0.2 (15% ethyl acetate in hexanes); $^1$H NMR (700 MHz, CDCl$_3$): δ 7.62 (d, J=7.6 Hz, 1H), 7.54 (m, 4H), 7.50 (m, 3H), 7.31 (m, 3H), 7.29 (m, 2H), 7.25 (m, 6H), 7.19 (t, J=7.6 Hz, 1H), 6.91 (d, J=8.2 Hz, 1H), 4.28 (t, J=6.8 Hz, 2H), 3.41 (t, J=6.9 Hz, 2H); $^{13}$C NMR (100 MHz, CDCl$_3$): δ 158.9, 132.5, 132.3, 131.8, 131.75, 131.64, 131.6, 129.0, 128.3, 128.2, 128.1, 128.0, 127.9, 127.8, 127.75, 126.1, 125.7, 125.6, 125.4, 123.23, 123.2, 113.7, 97.1, 93.6, 93.4, 92.8, 92.0, 88.4, 88.3, 88.2, 69.3, 28.4; HRMS (EI): calcd for C$_{40}$H$_{25}$OBr [M]+ 600.1089, found 600.1088.

Example 26

2,2'-((3-(2-iodoethoxy)-1,2-phenylene)bis(ethyne-2,1-diyl))bis((phenylethynyl)benzene) (12b)

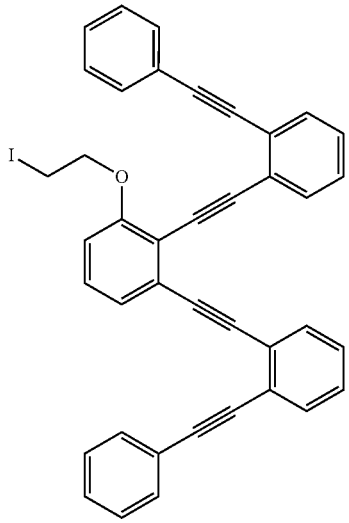 [SMILES: ICCOc1cccc(C#Cc2ccccc2C#Cc2ccccc2)c1C#Cc1ccccc1C#Cc1ccccc1]

Chromatographic purification (20% ethyl acetate in hexanes) afforded compound 12b (99%) as a orange oil. $R_f$=0.2 (15% ethyl acetate in hexanes); $^1$H NMR (400 MHz, CDCl$_3$): δ 7.62 (d, J=7.4 Hz, 1H), 7.53 (m, 5H), 7.50 (m, 2H), 7.27 (m, 11H), 7.19 (t, J=6.7 Hz, 1H), 6.89 (d, J=8.1 Hz, 1H), 4.23 (t, J=7.4 Hz, 2H), 3.20 (t, J=7.4 Hz, 2H); $^{13}$C NMR (100 MHz, CDCl$_3$): δ 158.6, 132.5, 132.3, 131.8, 131.64, 131.6, 129.0, 128.3, 128.2, 128.1, 128.0, 127.9, 127.8, 126.1, 125.7, 125.6, 125.5, 125.4, 123.2, 116.2, 113.4, 97.0, 93.6, 93.4, 92.8, 92.0, 90.8, 88.4, 88.3, 70.1, 0.6; HRMS (EI): calcd for C$_{40}$H$_{25}$IO [M]+ 648.53037, found 648.5357.

Example 27

2,2'-((3-(2-bromoethoxy)-1,2-phenylene)bis(ethyne-2,1-diyl))bis(((4-methoxyphenyl)ethynyl)benzene) (11c)

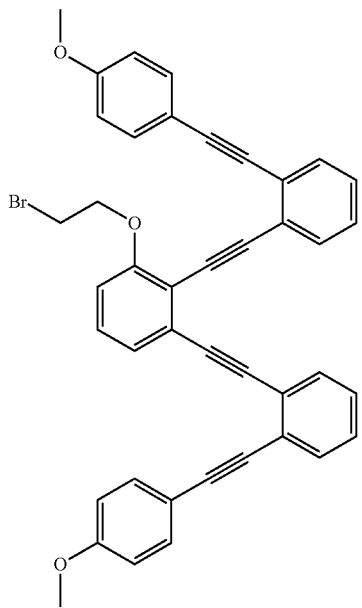 [SMILES: COc1ccc(C#Cc2ccccc2C#Cc2cccc(OCCBr)c2C#Cc2ccccc2C#Cc2ccc(OC)cc2)cc1]

Chromatographic purification (25% ethyl acetate in hexanes) afforded compound 11c (82%) as an orange-red oil. $R_f$=0.1 (15% ethyl acetate in hexanes); $^1$H NMR (600 MHz, CDCl$_3$): δ 7.64 (d, J=7.5 Hz, 1H), 7.56 (d, J=7.7 Hz, 1H), 7.53 (d, J=7.7 Hz, 1H), 7.49 (d, J=8.5 Hz, 3H), 7.46 (d, J=8.6 Hz, 2H), 7.31 (d, J=7.7 Hz, 1H), 7.25 (m, 4H), 7.18 (t, J=7.6 Hz, 1H), 6.91 (d, J=8.2 Hz, 1H), 6.83 (d, J=8.6 Hz, 2H), 6.79 (d, J=8.6 Hz, 2H), 4.29 (t, J=6.8 Hz, 2H), 3.78 (s, 3H), 3.76 (s, 3H), 3.44 (t, J=6.8 Hz, 2H); $^{13}$C NMR (150 MHz, CDCl$_3$): δ 159.6, 159.5, 158.8, 133.3, 133.2, 133.1, 132.5, 132.2, 131.5, 131.3, 128.9, 128.0, 127.9, 127.7, 127.4, 126.0, 125.8, 125.6, 125.5, 125.3, 116.3, 115.3, 113.9, 113.8, 113.76, 113.7, 97.2, 93.8, 93.5, 92.9, 91.9, 88.0, 87.2, 87.1, 69.3, 55.15, 55.1, 28.5; HRMS (ESI): calcd for C$_{42}$H$_{29}$BrO$_3$ [M]+ 683.11978, found 683.12098.

Example 29

2,2'-((3-(2-iodoethoxy)-1,2-phenylene)bis(ethyne-2,1-diyl))bis(((4-methoxyphenyl)ethynyl)benzene) (12c)

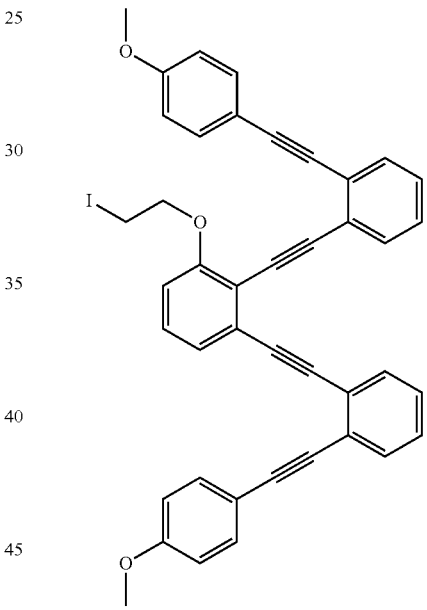

Chromatographic purification (25% ethyl acetate in hexanes) afforded compound 12c (99%) as an orange-red oil. $R_f$=0.1 (15% ethyl acetate in hexanes); $^1$H NMR (600 MHz, CDCl$_3$): δ 7.63 (d, J=7.6 Hz, 1H), 7.55 (d, J=7.7 Hz, 1H), 7.51 (d, J=7.7 Hz, 1H), 7.48 (m, 3H), 7.45 (d, J=8.8 Hz, 2H), 7.29 (t, J=7.6 Hz, 1H), 7.24 (m, 4H), 7.18 (t, J=3.2 Hz, 1H), 6.89 (d, J=8.2 Hz, 1H), 6.83 (d, J=8.7 Hz, 2H), 6.80 (d, J=8.6 Hz, 2H), 4.24 (t, J=7.4 Hz, 2H), 3.79 (s, 3H), 3.78 (s, 3H), 3.22 (t, J=7.4 Hz, 2H); $^{13}$C NMR (150 MHz, CDCl$_3$): δ 159.6, 159.55, 158.6, 133.2, 133.1, 132.5, 132.3, 131.5, 131.4, 128.9, 128.0, 127.9, 127.8, 127.4, 126.1, 125.8, 125.7, 125.5, 125.4, 116.2, 115.4, 115.36, 113.9, 113.83, 113.8, 113.5, 97.2, 93.8, 93.5, 92.9, 91.9, 88.1, 87.2, 87.1, 70.2, 55.2, 0.6; HRMS (ESI): calcd for C$_{42}$H$_{29}$IO$_3$ [M]+ 709.12396, found 709.12371.

Example 30

(E)-5-benzylidene-4-phenyl-3,5-dihydro-2H-cyclopenta[de]chromene (2a)

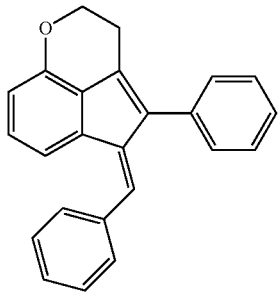 [SMILES: C(=C1\C(c2ccccc2)=C2CCOc3cccc1c32)/c1ccccc1]

Chromatographic purification (15% ethyl acetate in hexanes) afforded compound 2a (63%) as a yellow oil. $R_f$=0.3 (15% ethyl acetate in hexanes); $^1$H NMR (700 MHz, CDCl$_3$): δ 7.54 (d, J=3.9 Hz, 2H), 7.46 (m, 5H), 7.40 (m, 1H), 7.36 (tt, J=9.9, 1.5 Hz, 1H), 7.28 (s, 1H), 7.02 (m, 1H), 7.00 (d, J=7.5 Hz, 1H), 6.88 (t, J=7.8 Hz, 1H), 6.72 (d, J=8.0 Hz, 1H), 4.24 (t, J=5.7 Hz, 2H), 2.92 (t, J=5.7 Hz, 2H); $^{13}$C NMR (150 MHz, CDCl$_3$): δ 151.0, 141.7, 137.0, 134.8, 134.1, 134.0, 133.0, 131.6, 130.4, 130.2, 129.9, 129.4, 128.4, 128.3, 128.2, 126.9, 116.6, 114.6, 67.1, 25.3; UV/Vis (MeOH): $\lambda_{max}$=273 nm; HRMS (EI): calcd for C$_{24}$H$_{18}$O [M]+ 322.1358, found 322.1349.

Example 31

(E)-5-(4-methylbenzylidene)-4-(p-tolyl)-3,5-dihydro-2H-cyclopenta[de]chromene (2b)

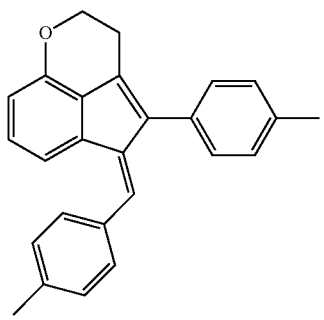 [SMILES: Cc1ccc(/C=C2/C(c3ccc(C)cc3)=C3CCOc4cccc2c43)cc1]

Chromatographic purification (15% ethyl acetate in hexanes) afforded compound 2b (70%) as a yellow oil. $R_f$=0.3 (15% ethyl acetate in hexanes); $^1$H NMR (600 MHz, CD$_3$CN): δ 7.46 (d, J=7.6 Hz, 2H), 7.34 (d, J=7.6 Hz, 2H), 7.30 (d, J=7.6 Hz, 2H), 7.27 (d, J=7.6 Hz, 2H), 7.24 (s, 1H), 7.08 (d, J=7.6 Hz, 1H), 6.90 (t, J=7.7 Hz, 1H), 6.72 (d, J=8.0 Hz, 1H), 4.26 (t, J=5.6 Hz, 2H), 2.93 (t, J=5.7 Hz, 2H), 2.40 (s, 6H); $^{13}$C NMR (150 MHz, CD$_3$CN): δ 152.5, 142.4, 140.0, 138.2, 135.7, 135.4, 135.3, 134.2, 133.0, 132.7, 131.4, 130.8, 130.49, 130.47, 128.1, 117.6, 115.6, 68.4, 26.3, 21.8, 21.7; UV/Vis (MeOH): $\lambda_{max}$=274 nm; HRMS (EI): calcd for C$_{26}$H$_{22}$O [M]+ 350.16707, found 350.16618.

Example 32

(E)-5-(4-fluorobenzylidene)-4-(4-fluorophenyl)-3,5-dihydro-2H-cyclopenta[de]chromene (2c)

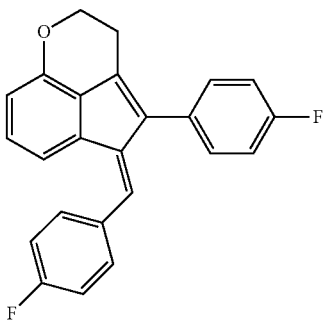 [SMILES: Fc1ccc(/C=C2/C(c3ccc(F)cc3)=C3CCOc4cccc2c43)cc1]

Chromatographic purification (15% ethyl acetate in hexanes) afforded compound 2c (87%) as a red oil. $R_f$=0.4 (15% ethyl acetate in hexanes); $^1$H NMR (600 MHz, CD$_3$CN): δ 7.55 (dd, J=8.5, 5.6 Hz, 2H), 7.43 (dd, J=8.5, 5.7 Hz, 2H), 7.20 (q, J=8.9 Hz, 3H), 7.17 (d, J=4.8 Hz, 1H), 6.99 (d, J=7.5 Hz, 1H), 6.90 (t, J=7.8 Hz, 1H), 6.73 (d, J=8.1 Hz, 1H), 4.24 (t, J=5.8 Hz, 2H), 2.89 (t, J=5.8 Hz, 2H); $^{13}$C NMR (150 MHz, CD$_3$CN): δ 164.1 (d, J=107.5 Hz), 162.5 (d, J=105.6 Hz), 152.3, 142.7, 134.9, 134.1 (d, J=3.27 Hz), 133.9, 133.4, 132.9 (d, J=72.6 Hz), 132.7 (d, J=72.6 Hz), 132.6, 131.8 (d, J=3.3 Hz), 130.8, 128.2, 117.23, 116.5, 116.4 (d, J=4.2 Hz), 116.2, 115.7, 68.0, 25.8; UV/Vis (MeOH): λmax=301 nm; HRMS (EI): calcd for C$_{24}$H$_{16}$OF$_2$ [M]+ 358.11693, found 358.11632.

Example 33

(E)-5-(4-methoxybenzylidene)-4-(4-methoxyphenyl)-3,5-dihydro-2H-cyclopenta[de]chromene (2d)

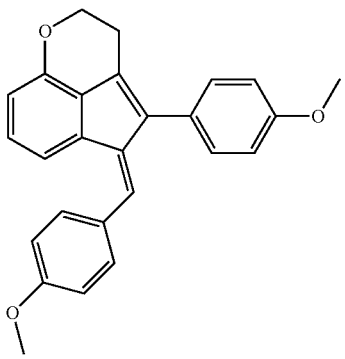 [SMILES: COc1ccc(/C=C2/C(c3ccc(OC)cc3)=C3CCOc4cccc2c43)cc1]

Chromatographic purification (15% ethyl acetate in hexanes) afforded compound 2d (74%) as a red oil. $R_f$=0.4 (20% ethyl acetate in hexanes); $^1$H NMR (600 MHz, CDCl$_3$): δ 7.53 (d, J=8.0 Hz, 2H), 7.34 (d, J=4.1 Hz, 2H), 7.25 (t, J=5.3 Hz, 1H), 7.19 (s, 1H), 7.00 (d, J=4.1 Hz, 2H), 6.96 (d, J=4.1 Hz, 2H), 6.92 (t, J=5.7 Hz, 1H), 6.76 (d, J=8.0 Hz, 1H), 4.30 (t, J=5.6 Hz, 2H), 3.88 (s, 3H), 3.87 (s, 3H), 2.96 (t, J=5.6 Hz, 2H); $^{13}$C NMR (150 MHz, CDCl$_3$): δ 159.7, 158.6, 150.8, 140.7, 134.1, 132.9, 131.3, 131.1, 130.3, 130.2, 130.1, 126.5, 116.3, 114.2, 113.8, 113.79, 113.3, 67.2, 55.3, 25.3; UV/Vis (MeOH): λmax=275 nm; HRMS (EI): calcd for $C_{26}H_{22}O_3$ [M]+ 382.15690, found 382.15644.

Example 34

(E)-trimethyl((4-(trimethylsilyl)-2H-cyclopenta[de]chromen-5(3H)-ylidene)methyl)silane (2e)

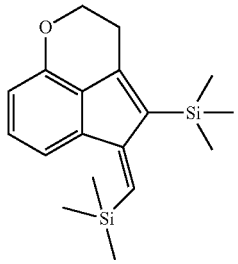 [SMILES: C[Si](C)(C)/C=C1/C([Si](C)(C)C)=C2CCOc3cccc1c32]

Chromatographic purification (15% ethyl acetate in hexanes) afforded compound 2e (74%) as a yellow oil. $R_f$=0.4 (20% ethyl acetate in hexanes); $^1$H NMR (600 MHz, CDCl$_3$): δ 7.22 (d, J=7.5 Hz, 1H), 7.07 (t, J=7.7 Hz, 1H), 6.73 (d, J=8.0 Hz, 1H), 6.54 (s, 1H), 4.28 (t, J=5.9 Hz, 2H), 2.99 (t, J=5.8 Hz, 2H), 0.34 (s, 9H), 0.30 (s, 9H); $^{13}$C NMR (150 MHz, CDCl$_3$): δ 159.7, 150.9, 146.0, 138.2, 136.7, 131.5, 127.3, 116.5, 114.2, 67.2, 27.7, 1.3, 0.2; UV/Vis (MeOH): $\lambda_{max}$=224 nm; HRMS (EI): calcd for $C_{18}H_{26}OSi_2$ [M]+ 314.1522, found 314.1522.

Example 35

(E)-4-(naphthalen-1-yl)-5-(naphthalen-1-ylmethylene)-3,5-dihydro-2H-cyclopenta[de]chromene (2f)

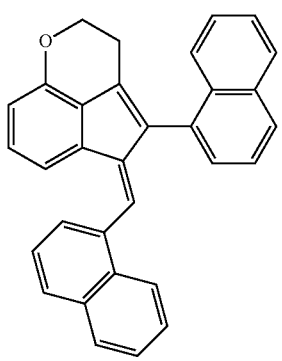 [SMILES: C(=C1\C(c2cccc3ccccc23)=C2CCOc3cccc1c32)/c1cccc2ccccc12]

Chromatographic purification (15% ethyl acetate in hexanes) afforded compound 2f (80%) as a yellow oil. $R_f$=0.5 (15% ethyl acetate in hexanes); $^1$H NMR (600 MHz, CDCl$_3$): δ 8.08 (m, 1H), 7.96 (m, 1H), 7.92 (dd, J=6.8, 2.7 Hz, 1H), 7.87 (d, J=7.8 Hz, 2H), 7.79 (d, J=8.6 Hz, 1H), 7.77 (d, J=7.0 Hz, 1H), 7.61 (m, 2H), 7.55 (m, 2H), 7.51 (m, 1H), 7.47 (m, 1H), 7.39 (m, 1H), 7.33 (s, 1H), 6.83 (t, J=7.8 Hz, 1H), 6.77 (d, J=4.1 Hz, 1H), 6.71 (d, J=7.4 Hz, 1H), 4.33 (t, J=5.8 Hz, 2H), 2.80 (t, J=5.7 Hz, 2H); $^{13}$C NMR (150 MHz, CDCl$_3$): δ 150.9, 144.3, 134.4, 134.2, 133.8, 133.5, 133.0, 132.5, 132.4, 131.6, 131.5, 130.1, 128.7, 128.65, 128.4, 128.36, 128.0, 127.4, 126.9, 126.7, 126.2, 126.1, 126.0, 125.9, 125.3, 125.2, 125.1, 120.1, 116.9, 114.9, 67.2, 25.4; UV/Vis (MeOH): $\lambda_{max}$=320 nm; HRMS (EI): calcd for $C_{32}H_{22}O$ [M]+ 422.1671, found 422.1664.

Example 36

2-(4-fluorophenyl)-4-((4-fluorophenyl)ethynyl)benzofuran (4)

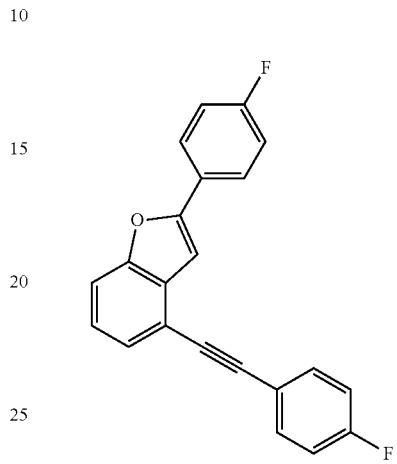

Chromatographic purification (10% ethyl acetate in hexanes) afforded compound 4 (38%) as a red brown solid. $R_f$=0.8 (10% ethyl acetate in hexanes); $^1$H NMR (600 MHz, CDCl$_3$): δ 7.88 (m, 2H), 7.60 (m, 2H), 7.50 (d, J=8.2 Hz, 1H), 7.41 (dd, J=2.7, 0.6 Hz, 1H), 7.26 (t, J=5.2 Hz, 1H), 7.16 (m, 3H), 7.09 (tt, J=8.7, 1.9 Hz, 2H); $^{13}$C NMR (150 MHz, CDCl$_3$): δ 163.9, 163.5, 155.7, 154.4, 133.6, 133.5, 131.3, 127.0, 126.97, 126.5, 124.1, 116.0 (d, J=22.0 Hz), 115.7 (d, J=22.2 Hz), 115.4, 111.5, 100.7, 91.5, 86.8; HRMS (EI): calcd for $C_{22}H_{12}OF_2$ [M]+ 330.08563, found 330.08580.

Example 37

2,3-bis((4-fluorophenyl)ethynyl)phenol (5)

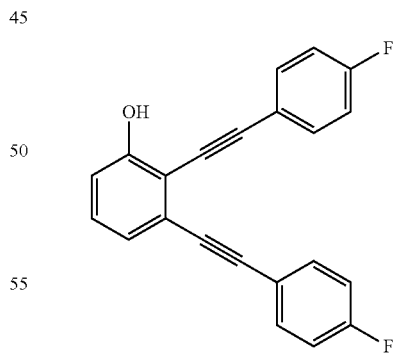

Chromatographic purification (10% ethyl acetate in hexanes) afforded compound 5 (55%) as a red orange oil. $R_f$=0.2 (10% ethyl acetate in hexanes); $^1$H NMR (600 MHz, CDCl$_3$): δ 7.55 (m, 2H), 7.51 (m, 2H), 7.23 (t, J=15.9 Hz, 1H), 7.13 (dd, J=2.9, 0.9 Hz, 1H), 7.08 (m, 2H), 7.04 (m, 2H), 6.97 (dd, J=8.3, 1.0 Hz, 1H), 5.91 (bs, 1H); $^{13}$C NMR (150 MHz, CDCl$_3$): δ 163.6 (d, J=36.2 Hz), 162.0 (d, J=35.7 Hz), 156.4, 133.6, 133.5, 129.8, 125.8, 124.1, 119.2, 118.5, 115.9 (d, J=22.7 Hz), 115.7 (d, J=22.0 Hz), 114.8, 112.0, 99.0, 92.3, 87.6, 81.8; HRMS (EI): calcd for $C_{22}H_{12}OF_2$ [M]+ 330.08563, found 330.08483.

Example 39

13-methyl-11-(p-tolyl)-1,2,11,19c-tetrahydrobenzo[6,7]benzo[1',2']fluoreno[3',4':4,5]indeno[1,2,3-de]chromene (13a)

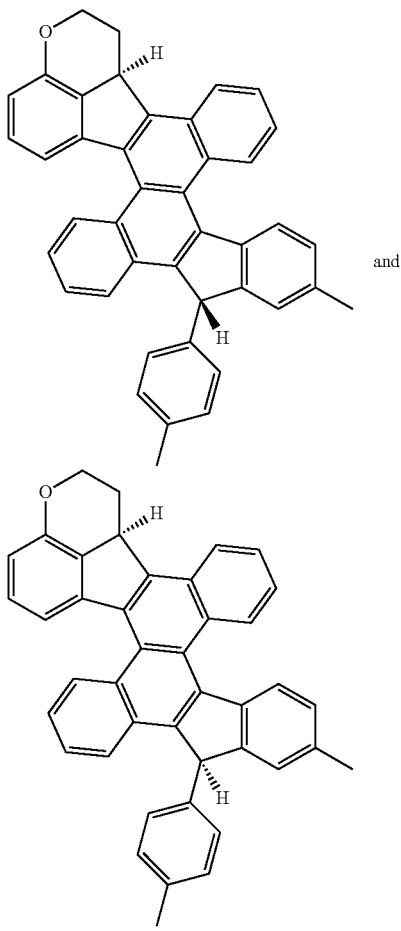

and

Chromatographic purification (20% ethyl acetate in hexanes) afforded compound 13a as a mixture of diastereomers X=Br (26%) X=I (52%) as a dark yellow oil. The oil crystallized upon slow evaporation in a 3:1 mixture of methanol:hexane to provide crystals of one of the individual diastereomers while the other diastereomer remained an oil. These diastereomers were separated by filtration. $R_f$=0.2 (15% ethyl acetate in hexanes); $^1$H NMR (600 MHz, CDCl$_3$): δ 9.08 (d, J=8.3 Hz, 1H), 9.02 (d, J=7.7 Hz, 1H), 8.50 (d, J=8.3 Hz, 1H), 7.91 (d, J=8.0 Hz, 1H), 7.86 (d, 7.4 Hz, 1H), 7.73 (t, J=7.7 Hz, 1H), 7.52 (m, 2H), 7.44 (m, 2H), 7.34 (d, J=7.8 Hz, 2H), 7.23 (s, 1H), 7.15 (d, J=7.9 Hz, 2H), 7.13 (t, J=7.9 Hz, 1H), 7.02 (d, J=8.1 Hz, 1H), 6.74 (d, J=8.0 Hz, 1H), 5.28 (s, 1H), 4.97 (td, J=12.6, 4.7 Hz, 1H), 4.69 (dd, J=11.7, 6.3 Hz, 1H), 3.53 (dd, J=14.2, 3.5 Hz, 1H), 2.35 (s, 3H), 2.34 (s, 3H), 2.28 (m, 1H), 1.98 (m, 1H); $^{13}$C NMR (150 MHz, CDCl$_3$): δ 153.7, 150.1, 147.9, 139.3, 138.3, 136.6, 136.53, 136.5, 135.8, 131.1, 130.2, 129.94, 129.9, 129.8, 129.7, 129.5, 129.48, 128.9, 128.8, 128.7, 128.2, 127.9, 127.7, 127.4, 127.2, 127.1, 125.4, 125.1, 124.8, 124.5, 124.3, 123.4, 116.2, 114.8, 65.2, 51.9, 38.7, 30.8, 21.4, 21.1; UV/Vis (MeOH): λmax=421 nm; HRMS (EI): calcd for $C_{42}H_{30}O$ [M]+ 550.2297, found 550.2253. The $2^{nd}$ diastereomer was also a yellow oil. $R_f$=0.2 (15% ethyl acetate in hexanes); $^1$H NMR (600 MHz, CDCl$_3$): δ 8.98 (d, J=8.2 Hz, 2H), 8.50 (d, J=8.3 Hz, 1H), 7.96 (d, J=8.0 Hz, 1H), 7.80 (d, J=7.1 Hz, 1H), 7.72 (t, J=7.4 Hz, 1H), 7.54 (d, J=7.6 Hz, 1H), 7.49 (t, J=7.6 Hz, 1H), 7.43 (m, 2H), 7.13 (m, 2H), 7.04 (m, 3H), 6.89 (m, 2H), 6.76 (d, J=7.9 Hz, 1H), 5.61 (s, 1H), 5.30 (s, 1H), 4.97 (td, J=12.4, 4.4 Hz, 1H), 4.69 (dd, J=11.4, 7.2 Hz, 1H), 3.53 (dd, J=14.0, 4.0 Hz, 1H), 2.33 (s, 3H), 2.29 (s, 3H), 1.97 (m, 1H); $^{13}$C NMR (150 MHz, CDCl$_3$): δ 154.7, 150.1, 145.4, 139.2, 138.3, 138.0, 137.0, 136.5, 134.9, 133.6, 132.5, 130.3, 130.1, 129.9, 129.8, 129.4, 129.3, 129.2, 129.1, 128.9, 128.7, 128.6, 127.7, 127.1, 125.2, 124.9, 124.5, 124.3, 123.3, 123.1, 121.7, 118.4, 115.0, 113.3, 65.2, 51.8, 30.8, 29.7, 21.7, 21.6; UV/Vis (MeOH): $\lambda_{max}$=498 nm; HRMS (EI): calcd for $C_{42}H_{30}O$ [M]+ 550.2297, found 550.2290.

Example 40

11-phenyl-1,2,11,19c-tetrahydrobenzo[6,7]benzo[1',2']fluoreno[3',4':4,5]indeno[1,2,3-de]chromene (13b)

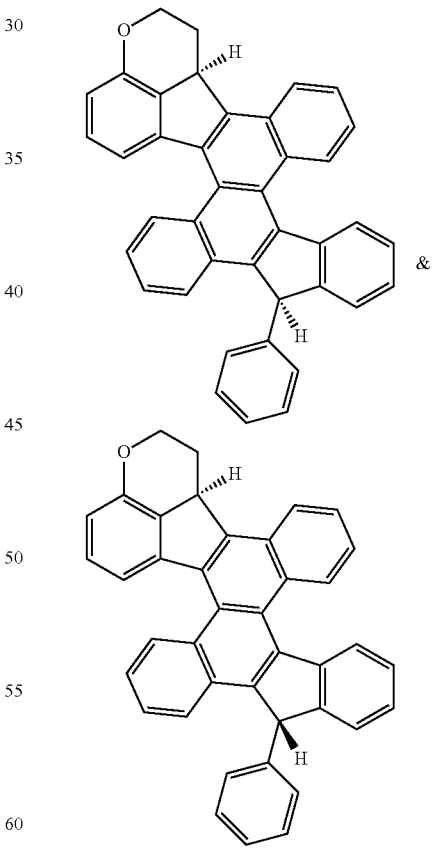

Chromatographic purification (20% ethyl acetate in hexanes) afforded compound 13b as a mixture of diastereomers, 1:1.1, X=Br (35%) X=I (55%) as a orange oil. $R_f$=0.3 (10% ethyl acetate in hexanes); $^1$H NMR (700 MHz, CDCl$_3$): δ 9.07 (d, J=7.9 Hz, 1H), 9.02 (t, J=8.9 Hz, 2H), 8.92 (d, J=8.5 Hz, 2H), 8.50 (d, J=7.6 Hz, 2H), 8.47 (d, J=8.2 Hz, 1H), 8.12 (d, J=7.9 Hz, 1H), 8.08 (d, J=7.28 Hz, 2H), 7.84 (d, J=7.8 Hz, 2H), 7.79 (d, J=8.5 Hz, 2H), 7.69 (q, J=7.0 Hz, 2H), 7.56 (d, J=7.6 Hz, 3H), 7.53 (q, J=7.1 Hz, 2H), 7.50 (s, 2H), 7.44 (m, 7H), 7.39 (s, 2H), 7.35 (t, J=7.4 Hz, 3H), 7.30 (m, 5H), 7.23 (m, 7H), 7.17 (m, 4H), 7.06 (d, J=7.6 Hz, 1H), 7.01 (t, J=8.1 Hz, 2H), 6.76 (t, J=7.7 Hz, 2H), 5.68 (s, 1H), 5.35 (s, 1H), 5.06 (t, J=6.1 Hz, 2H), 4.70 (m, 2H), 3.02 (d, J=13.7 Hz, 2H), 2.67 (m, 2H), 1.83 (m, 2H); $^{13}$C NMR (150 MHz, CDCl$_3$): δ 153.9, 149.6, 144.1, 142.2, 140.7, 136.4, 134.2, 132.6, 131.1, 130.1, 129.2, 129.1, 128.9, 128.8, 128.6, 128.4, 127.8, 127.2, 127.17, 127.1, 126.8, 126.7, 126.6, 126.1, 124.5, 124.3, 124.2, 124.0, 123.7, 123.5, 121.0, 116.0, 115.4, 112.9, 111.2, 64.1, 54.9, 54.4, 43.1, 31.4, 29.7; UV/Vis (MeOH): $\lambda_{max}$=465 nm; HRMS (EI): calcd for C$_{40}$H$_{26}$O [M]+ 522.19837, found 522.19865.

Example 41

13-methoxy-11-(4-methoxyphenyl)-1,2,11,19c-tetrahydrobenzo[6,7]benzo[1',2']fluoreno[3',4':4,5]indeno[1, 2,3-de]chromene (13c)

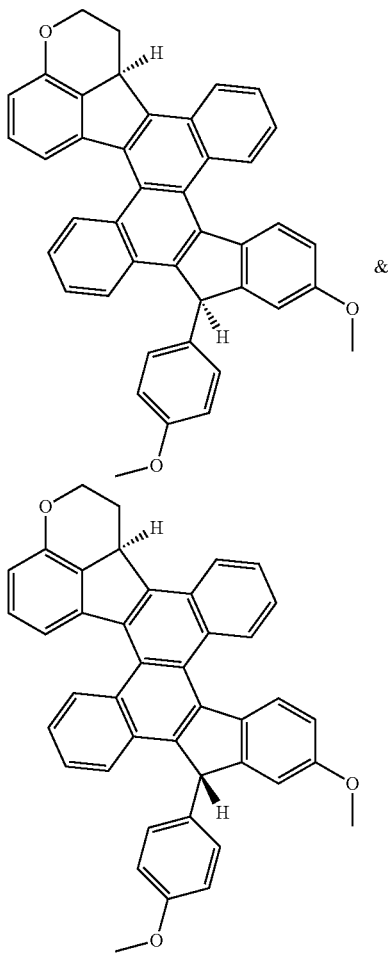

Chromatographic purification (20% ethyl acetate in hexanes) afforded compound 13c as a mixture of diastereomers, 1:1.3, X=Br (32%) X=I (55%) as a yellow-orange oil. R$_f$=0.2 (10% ethyl acetate in hexanes); $^1$H NMR (700 MHz, CDCl$_3$): δ 9.08 (d, J=8.3 Hz, 1H), 9.03 (m, 2H), 8.98 (t, J=7.7 Hz, 2H), 8.50 (d, J=8.5 Hz, 2H), 8.18 (m, 1H), 8.03 (d, J=8.6 Hz, 0.5H), 7.99 (d, J=8.3 Hz, 1.5H), 7.94 (d, J=8.7 Hz, 1H), 7.84 (m, 2H), 7.78 (m, 1H), 7.72 (q, J=3.2 Hz, 2H), 7.66 (m, 1H), 7.63 (d, J=7.7 Hz, 1H), 7.54 (t, J=8.5 Hz, 2H), 7.50 (q, J=3.9 Hz, 3H), 7.42 (m, 5H), 7.36 (d, J=8.3 Hz, 3H), 7.17 (m, 1H), 7.13 (q, J=7.8 Hz, 2H), 6.96 (m, 2H), 6.84 (m, 1H), 6.76 (m, 8H), 5.58 (s, 1H), 5.26 (s, 1H), 4.97 (m, 2H), 4.76 (m, 1H), 4.70 (m, 3H), 4.62 (dd, J=12.0, 4.4 Hz, 1H), 3.80 (s, 3H), 3.79 (s, 3H), 3.78 (s, 2H), 3.75 (s, 2H), 3.53 (d, J=11.0 Hz, 2H), 3.04 (d, J=12.5 Hz, 1H), 1.96 (m, 2H); $^{13}$C NMR (150 MHz, CDCl$_3$): δ 159.0, 158.9, 158.8, 158.7, 158.6, 158.4, 153.6, 153.58, 152.5, 152.0, 151.9, 144.1, 142.0, 136.5, 136.4, 135.5, 135.4, 134.8, 134.7, 134.0, 133.4, 133.1, 130.9, 129.8, 129.3, 129.2, 129.1, 129.0, 128.9, 128.8, 128.75, 128.7, 128.65, 126.6, 128.1, 127.9, 127.4, 127.3, 127.2, 126.9, 125.4, 125.2, 124.7, 124.5, 124.3, 124.2, 124.1, 124.07, 124.0, 123.95, 123.9, 116.1, 116.0, 114.9, 114.6, 114.59, 114.4, 114.3, 111.9, 111.8, 111.7, 110.9, 110.2, 68.2, 65.1, 55.5, 55.4, 55.2, 55.16, 54.1, 53.5, 42.2, 42.1, 30.9, 30.8, 29.7, 29.6; UV/Vis (MeOH): $\lambda_{max}$=428 nm; HRMS (EI): calcd for C$_{42}$H$_{30}$O$_3$ [M]+ 582.2195, found 582.2196.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:
1. A compound comprising repeat units having the structure (I):

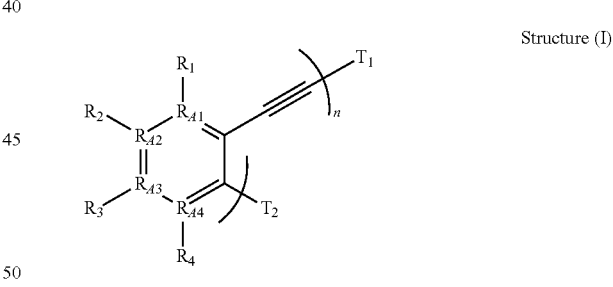

Structure (I)

wherein:
n is an integer having a value of at least three and less than 25;
R$_{A1}$, R$_{A2}$, R$_{A3}$, and R$_{A4}$ are each carbon; and R$_1$, R$_2$, R$_3$, and R$_4$ are each independently selected from the group consisting of hydrogen and a substituted or unsubstituted aliphatic moiety; wherein the substituents of the substituted aliphatic moiety are selected from the group consisting of chlorine, bromine, amino, and cyano;
or, alternatively, R$_1$, R$_{A2}$, R$_{A3}$, and R$_{A4}$ are each carbon; R$_1$, R$_2$, R$_3$, and R$_4$ are each independently selected from the group consisting of hydrogen and a substituted or unsubstituted aliphatic moiety; wherein the substituents of the substituted aliphatic moiety are selected from the group consisting of chlorine, bromine, amino, and cyano any two adjacent R$_{A1}$, R$_{A2}$, R$_{A3}$, and R$_{A4}$ and the R$_1$, R$_2$, R$_3$, and $R_4$, respectively bonded thereto together with the atoms to which they are bonded complete naphthalene or anthracene;

$T_1$ and $T_2$ are each independently selected from the group consisting of hydrogen, an aliphatic moiety having from 1 to 18 carbon atoms; an aromatic moiety having from three to 18 carbon atoms; an alkoxy moiety having from 1 to 6 carbon atoms; and a cyano moiety; and further wherein at least one of the repeat units comprises an $R_1$ moiety having the structure (II):

Structure (II)

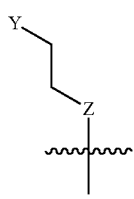

wherein:
Y comprises a reactive moiety selected from the group consisting of bromine and iodine; and
Z is O.

2. The compound of claim 1 wherein n has a value of at least four and less than 25.

3. The compound of claim 1 wherein n has a value between four and 25.

4. The compound of claim 1 having the structure (III):

Structure (III)

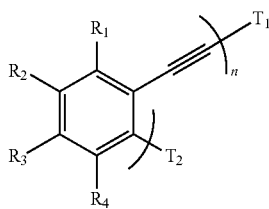

wherein n has a value of at least four and less than 25;
$R_1$, $R_2$, $R_3$, $R_4$, $T_1$, and $T_2$ are as defined in claim 1; and
further wherein at least one of the repeat units comprises an $R_1$ moiety having the structure (II):

Structure (II)

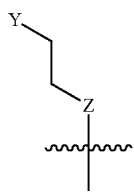

wherein Y and Z are as defined in claim 1.

5. The compound of claim 1 having the structure (VIII):

Structure (VIII)

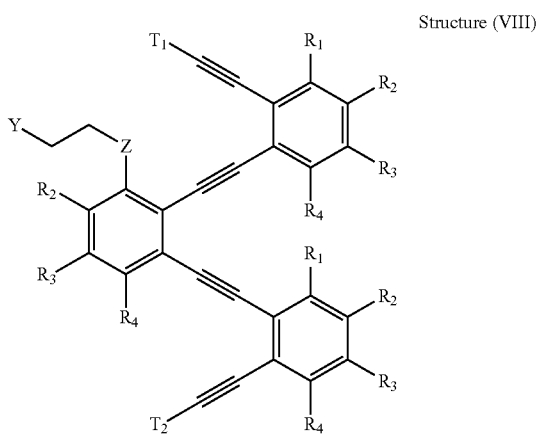

wherein $R_1$, $R_2$, $R_3$, $R_4$, $T_1$, $T_2$, Y, and Z are as defined in claim 1.

6. The compound of claim 5 wherein Z is an oxygen atom and Y is an iodine atom.

7. The compound of claim 1 having the structure:

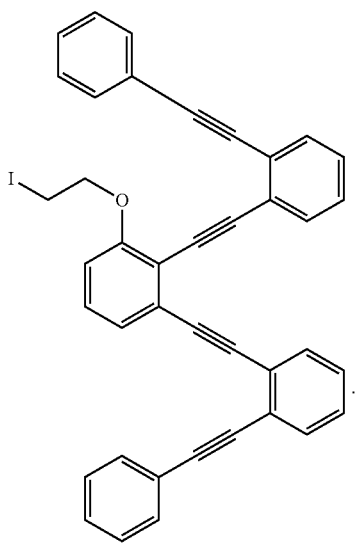 [SMILES: ICCOc1cccc(C#Cc2ccccc2C#Cc2ccccc2)c1C#Cc1ccccc1C#Cc1ccccc1]

* * * * *